(12) United States Patent
Hasegawa et al.

(10) Patent No.: US 8,835,094 B2
(45) Date of Patent: Sep. 16, 2014

(54) FLUOROALCOHOL, FLUORINATED MONOMER, POLYMER, RESIST COMPOSITION AND PATTERNING PROCESS

(75) Inventors: Koji Hasegawa, Joetsu (JP); Takeru Watanabe, Joetsu (JP); Tomohiro Kobayashi, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 127 days.

(21) Appl. No.: 13/235,719

(22) Filed: Sep. 19, 2011

(65) Prior Publication Data

US 2012/0077121 A1 Mar. 29, 2012

(30) Foreign Application Priority Data

Sep. 29, 2010 (JP) ................. 2010-218249

(51) Int. Cl.
| | |
|---|---|
| G03F 7/004 | (2006.01) |
| G03F 7/039 | (2006.01) |
| C08F 18/20 | (2006.01) |
| C08F 22/18 | (2006.01) |
| C08F 220/22 | (2006.01) |
| G03F 7/20 | (2006.01) |
| C07C 69/675 | (2006.01) |
| C08F 220/30 | (2006.01) |
| C07C 69/67 | (2006.01) |
| C07C 69/708 | (2006.01) |
| C08F 220/18 | (2006.01) |
| C08F 220/24 | (2006.01) |

(52) U.S. Cl.
CPC ............ *C07C 69/675* (2013.01); *G03F 7/0045* (2013.01); *C08F 220/18* (2013.01); *G03F 7/2041* (2013.01); *G03F 7/0046* (2013.01); *C08F 220/24* (2013.01); *G03F 7/0397* (2013.01); *C08F 220/30* (2013.01); *C07C 69/67* (2013.01); *C07C 69/708* (2013.01)
USPC ......... 430/270.1; 526/245; 526/247; 526/253

(58) Field of Classification Search
None
See application file for complete search history.

(56) References Cited

U.S. PATENT DOCUMENTS

| | | | |
|---|---|---|---|
| 6,312,867 | B1 | 11/2001 | Kinsho et al. |
| 6,784,312 | B2 | 8/2004 | Miyazawa et al. |
| 6,800,414 | B2 | 10/2004 | Nishimura et al. |
| 6,800,418 | B2 | 10/2004 | Yoon et al. |
| 6,830,866 | B2 | 12/2004 | Kobayashi et al. |
| 7,868,199 | B2 | 1/2011 | Hasegawa et al. |
| 7,981,589 | B2 | 7/2011 | Hasegawa et al. |
| 2004/0005512 | A1* | 1/2004 | Mizutani et al. ........... 430/270.1 |
| 2007/0275326 | A1* | 11/2007 | Hatakeyama et al. ..... 430/270.1 |
| 2009/0269696 | A1* | 10/2009 | Ohsawa et al. ............ 430/270.1 |
| 2009/0274978 | A1 | 11/2009 | Ohashi et al. |

FOREIGN PATENT DOCUMENTS

| | | |
|---|---|---|
| JP | 2000-336121 A | 12/2000 |
| JP | 2002-72484 A | 3/2002 |
| JP | 2003-40840 A | 2/2003 |
| JP | 2003-66612 A | 3/2003 |
| JP | 2003-192729 A | 7/2003 |
| JP | 2007-204385 A | 8/2007 |
| JP | 2009-269953 A | 11/2009 |
| JP | 4475435 B2 | 6/2010 |

OTHER PUBLICATIONS

Arimitsu et al., "Effect of Phenolic Hydroxyl Residues on the Improvement of Acid-Proliferation-Type Photoimaging Materials," Journal of Photopolymer Science and Technology, vol. 9, No. 1, 1996, pp. 29-30.

Arimitsu et al., "Sensitivity Enhancement of Chemical-Amplification-Type Photoimaging Materials by Acetoacetic Acid Derivatives," Journal of Photopolymer Science and Technology, vol. 8, No. 1, 1995, pp. 43-44.

Hirayama, "Resist and Cover Material Investigation for Immersion Lithography," 2nd Immersion Workshop, Jul. 11, 2003, pp. 1-16.

Kanna et al., "Study and Control of the Interfacial Mass Transfer of Resist Components in 193nm Immersion Lithography," Journal of Photopolymer Sciecne and Technology, vol. 18, No. 5, 2005, pp. 603-613.

(Continued)

*Primary Examiner* — Cynthia H Kelly
*Assistant Examiner* — Anna Malloy
(74) *Attorney, Agent, or Firm* — Birch, Stewart, Kolasch & Birch, LLP

(57) ABSTRACT

Fluoroalcohol compounds of formula (1) are useful in producing polymers which are used as the base resin to formulate radiation-sensitive resist compositions having transparency to radiation having a wavelength of up to 500 nm and improved development characteristics. $R^1$ is hydrogen or a monovalent $C_1$-$C_{20}$ hydrocarbon group in which any constituent —$CH_2$— moiety may be replaced by —O— or —C(=O)—, Aa is a ($k^1$+1)-valent $C_1$-$C_{20}$ hydrocarbon or fluorinated hydrocarbon group, and $k^1$ is 1, 2 or 3.

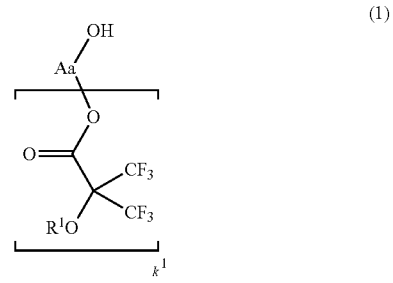

(1)

15 Claims, No Drawings

(56) References Cited

OTHER PUBLICATIONS

Kudo et al., "Enhancement of the Sensetivity of Chemical-Amplification-Type Photoimaging Materials by β-Tosyloxyketone Acetals." Journal of Photopolymer Science and Technology, vol. 8, No. 1, 1995, pp. 45-46.

Lin, "Semiconductor Foundry, Lithography, and Partners," Proceedings of SPIE, vol. 4690, 2002, pp. xxix-xlii.

Owa et al., "Immersion lithography; its potential performance and issues," Proceedings of SPIE, vol. 5040, 2003, pp. 724-733.

Wallraff et al., "Active Fluororesists for 157nm Lithography: IMB's Favorite Platforms," 2nd International Symposium on 157nm Lithography, May 14-17, 2001, pp. 1-10.

* cited by examiner

FLUOROALCOHOL, FLUORINATED MONOMER, POLYMER, RESIST COMPOSITION AND PATTERNING PROCESS

CROSS-REFERENCE TO RELATED APPLICATION

This non-provisional application claims priority under 35 U.S.C. §119(a) on Patent Application No. 2010-218249 filed in Japan on Sep. 29, 2010, the entire contents of which are hereby incorporated by reference.

TECHNICAL FIELD

This invention relates to fluoroalcohol compounds which are useful as raw materials for the synthesis of functional materials, pharmaceutical and agricultural chemicals, and fluorinated monomers (or polymerizable fluorinated compounds) derived therefrom. The fluorinated monomers are useful in producing polymers for use in the manufacture of radiation-sensitive resist compositions which are fully transparent to radiation having a wavelength of up to 500 nm, especially up to 300 nm, typically KrF, ArF or $F_2$ laser, and have good development characteristics.

The invention also relates to polymers comprising recurring units derived from the fluorinated monomers, photoresist compositions comprising the polymers, and a patterning process using the photoresist compositions.

BACKGROUND ART

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF, ArF or $F_2$ laser as the light source is strongly desired to reach the practical level as the micropatterning technique capable of achieving a feature size of 0.3 μm or less. Various alkali-soluble resins are used as the base resin in such resist compositions.

For KrF laser resists, a polyhydroxystyrene resin having phenolic hydroxyl groups as the alkali-soluble functional group is, in fact, a standard base resin. For ArF laser resists, poly(meth)acrylate resins using carboxyl groups as the alkali-soluble group and resins comprising polymerized units of cycloaliphatic olefin such as norbornene are under investigation. Of these, the poly(meth)acrylate resins are regarded, due to ease of polymerization, as a promising candidate that will find practical use. For these resist resins using as the alkali-soluble functional group carboxyl groups having a higher acidity than phenolic hydroxyl groups, however, an outstanding issue is difficulty of dissolution control, often leading to pattern collapse caused by swelling or the like.

Functional groups having an acidity comparable to phenolic hydroxyl groups are desired. It was proposed to use an alcohol having a plurality of fluorine atoms substituted at α- and α'-positions (e.g., having a partial structure: —$C(CF_3)_2$ OH) as the alkali-soluble functional group, as described in G. Wallraff et al., Active Fluororesists for 157 nm lithography in 2nd International Symposium on 157 nm Lithography. Styrene and norbornene derivatives having fluoroalcohol —$C(CF_3)_2OH$ incorporated therein are proposed as monomers used in the manufacture of base resins. Similar examples of fluoroalcohol-substituted norbornene are found in JP-A 2003-192729 and JP-A 2002-72484. For the polymerization of norbornene monomers, however, radical polymerization of monomers of the same type is difficult, and instead, special polymerization techniques such as coordinate polymerization using unique transition metal catalysts and ring-opening metathesis polymerization are necessary. Although alternating copolymerization between a norbornene monomer and a comonomer such as maleic anhydride or maleimide can be implemented by radical polymerization, the presence of comonomer imposes a substantial limit on the freedom of resin design.

JP-A 2003-040840 describes fluoroalcohol-substituted acrylate monomers. Although the method of preparing these monomers is not definite, the starting reactant used is hexafluoroacetone (boiling point −27° C.) which is awkward to handle because it is gaseous at room temperature. The synthesis of polymerizable compound must follow many steps, leaving the problems of an increased cost and difficult commercial implementation.

There is a strong demand to develop a polymerizable compound (or monomer) having both a polymerizable unsaturated group such as a (meth)acrylate structure and a functional group having an acidity comparable to phenolic hydroxyl, which compound can be prepared and polymerized both in an industrially acceptable and economic manner.

Over a decade, photolithography using ArF excimer laser light (193 nm) has been under active investigation. It was expected at the initial that the ArF lithography would be applied to the fabrication of 180-nm node devices. However, the KrF excimer lithography survived to the mass-scale fabrication of 130-nm node devices. So, the full application of ArF lithography started from the 90-nm node. The ArF lithography combined with a lens having an increased numerical aperture (NA) of 0.9 is considered to comply with 65-nm node devices. For the next 45-nm node devices which required an advancement to reduce the wavelength of exposure light, the $F_2$ lithography of 157 nm wavelength became a candidate. However, for the reasons that the projection lens uses a large amount of expensive $CaF_2$ single crystal, the scanner thus becomes expensive, hard pellicles are introduced due to the extremely low durability of soft pellicles, the optical system must be accordingly altered, and the etch resistance of resist is low; the postponement of $F_2$ lithography and the early introduction of ArF immersion lithography were advocated (see Proc. SPIE Vol. 4690 xxix).

In the ArF immersion lithography, the space between the projection lens and the wafer is filled with water. Since water has a refractive index of 1.44 at 193 nm, pattern formation is possible even using a lens with NA of 1.0 or greater. Theoretically, it is possible to increase the NA to 1.44. The resolution is improved by an increment of NA. A combination of a lens having NA of at least 1.2 with strong super-resolution technology suggests a way to the 45-nm node (see Proc. SPIE Vol. 5040, p 724).

Several problems associated with the presence of water on resist were pointed out. For example, projection lens contamination and pattern profile changes occur because the acid once generated from a photoacid generator and the amine compound added to the resist as a quencher can be dissolved in water. Inversely, swelling and circular defects known as water marks occur because water can penetrate into the resist film. For overcoming these problems, it was proposed to provide a protective coating between the resist and water (see 2nd Immersion Workshop, Jul. 11, 2003, Resist and Cover Material Investigation for Immersion Lithography); and to prevent resist materials from dissolution in water or water penetration by controlling the water repellency of resist materials, typically photoacid generators (PAG) or base resins (see J. Photopolymer Sci. and Technol., Vol. 18, No. 5, p 603 (2005)).

CITATION LIST

Patent Document 1: JP-A 2003-192729
Patent Document 2: JP-A 2002-072484
Patent Document 3: JP-A 2003-040840
Non-Patent Document 1: G. Wallraff et al., Active Fluororesists for 157 nm lithography in 2nd International Symposium on 157 nm Lithography
Non-Patent Document 2: Proc. SPIE Vol. 4690 xxix
Non-Patent Document 3: Proc. SPIE Vol. 5040, p 724
Non-Patent Document 4: 2nd Immersion Workshop, Jul. 11, 2003, Resist and Cover Material Investigation for Immersion Lithography
Non-Patent Document 5: J. Photopolymer Sci. and Technol., Vol. 18, No. 5, p 603 (2005)

DISCLOSURE OF THE INVENTION

An object of the present invention is to provide fluorinated monomers which are useful for the preparation of polymers to be formulated in resist compositions, the resist compositions exhibiting a high resolution and preventing dissolution in immersion media and penetration of immersion media when processed by photolithography using high-energy radiation such as ArF excimer laser radiation as a light source, especially immersion lithography; fluoroalcohols useful in preparing the fluorinated monomers; polymers obtained from the fluorinated monomers; resist compositions comprising the polymers as a base resin; and a patterning process using the resist compositions.

The inventors have found that a fluoroalcohol of the general formula (1) shown below and a fluorinated monomer of the general formula (2) shown below can be readily prepared, and that a resist composition comprising a polymer derived from the fluorinated monomer as a base resin exhibits a high resolution and an anti-swelling effect, and prevents dissolution in water as an immersion medium and penetration of water when processed by photolithography, especially immersion lithography so that the polymer is advantageously used in resist compositions, especially chemically amplified positive resist compositions for precise micropatterning.

Accordingly, the present invention provides a fluoroalcohol, fluorinated monomer, polymer, resist composition, and patterning process, as defined below.

In a first aspect, the invention provides a fluoroalcohol compound having the general formula (1):

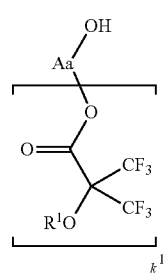

wherein $R^1$ is hydrogen or a straight, branched or cyclic monovalent $C_1$-$C_{20}$ hydrocarbon group in which any constituent —$CH_2$— moiety may be replaced by —O— or —C(=O)—, Aa is a straight, branched or cyclic ($k^1$+1)-valent $C_1$-$C_{20}$ hydrocarbon or fluorinated hydrocarbon group, and $k^1$ is an integer of 1 to 3.

In a second aspect, the invention provides a fluorinated monomer having the general formula (2), obtained by esterification of a fluoroalcohol compound having formula (1) as set forth in claim 1,

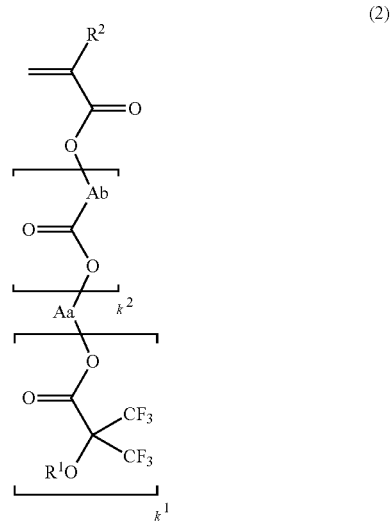

wherein $R^1$ is hydrogen or a straight, branched or cyclic monovalent $C_1$-$C_{20}$ hydrocarbon group in which any constituent —$CH_2$— moiety may be replaced by —O— or —C(=O)—, $R^2$ is hydrogen, fluorine, methyl or trifluoromethyl, Aa is a straight, branched or cyclic ($k^1$+1)-valent $C_1$-$C_{20}$ hydrocarbon or fluorinated hydrocarbon group, Ab is a straight, branched or cyclic divalent $C_1$-$C_6$ hydrocarbon group, $k^1$ is an integer of 1 to 3, and $k^2$ is 0 or 1.

In a third aspect, the invention provides a polymer comprising recurring units having the general formula (2a):

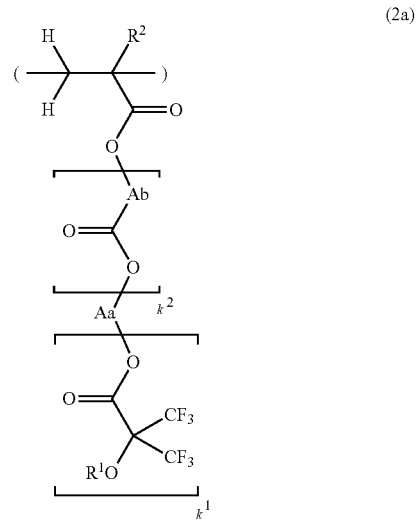

wherein $R^1$, $R^2$, Aa, Ab, $k^1$, and $k^2$ are as defined above.

In a preferred embodiment, the polymer may further comprise recurring units of at least one type selected from the general formulas (2A) to (2D):

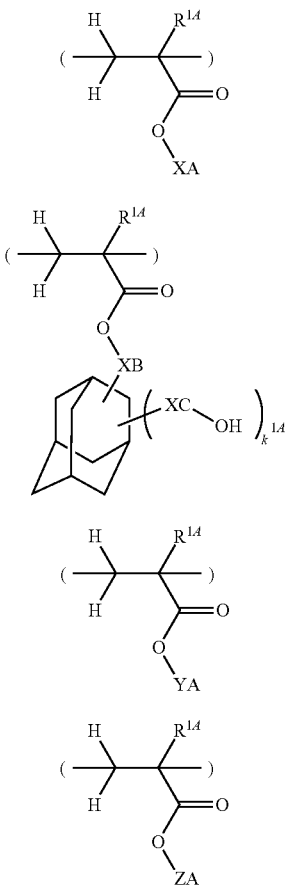

(2A)
(2B)
(2C)
(2D)

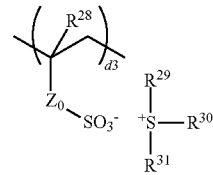

(d3)

wherein $R^{14}$ is hydrogen, fluorine, methyl or trifluoromethyl, XA is an acid labile group, XB and XC are each independently a single bond or a straight or branched divalent $C_1$-$C_4$ hydrocarbon group, YA is a substituent group having lactone structure, ZA is hydrogen, a $C_1$-$C_{15}$ fluoroalkyl group or a $C_1$-$C_{15}$ fluoroalcohol-containing substituent group, and $k^{1A}$ is an integer of 1 to 3.

In another preferred embodiment, the polymer may further comprise recurring units of at least one type selected from the general formulas (d1) to (d3):

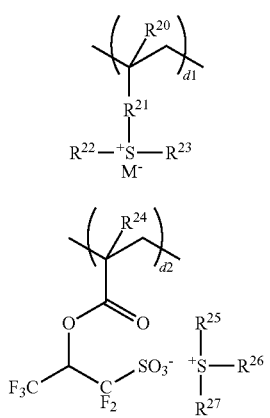

(d1)
(d2)

wherein $R^{20}$, $R^{24}$ and $R^{28}$ are hydrogen or methyl, $R^{21}$ is a single bond, phenylene, —O—$R^{33}$—, or —C(=O)—Y—$R^{33}$—, Y is oxygen or NH, $R^{33}$ is a straight, branched or cyclic $C_1$-$C_6$ alkylene group, alkenylene group or phenylene group, which may contain a carbonyl (—CO—), ester (—COO—), ether (—O—), or hydroxyl radical, $R^{22}$, $R^{23}$, $R^{25}$, $R^{26}$, $R^{27}$, $R^{29}$, $R^{30}$, and $R^{31}$ are each independently a straight, branched or cyclic $C_1$-$C_{12}$ alkyl group which may contain a carbonyl, ester or ether radical, or $C_6$-$C_{12}$ aryl group, $C_7$-$C_{20}$ aralkyl group or thiophenyl group, $Z_0$ is a single bond, methylene, ethylene, phenylene, fluorinated phenylene, —O—$R^{32}$—, or —C(=O)—$Z_1$—$R^{32}$—, $Z_1$ is oxygen or NH, $R^{32}$ is a straight, branched or cyclic $C_1$-$C_6$ alkylene group, alkenylene group or phenylene group, which may contain a carbonyl, ester, ether, or hydroxyl radical, and $M^-$ is a non-nucleophilic counter ion.

In a fourth aspect, the invention provides a resist composition comprising the polymer defined above as a base resin, an acid generator, and an organic solvent; or a resist composition comprising the polymer further comprising units of formula (d1), (d2) or (d3) as a base resin and an organic solvent.

In a fifth aspect, the invention provides a pattern forming process comprising the steps of applying the resist composition defined above onto a substrate to form a resist coating; heat treating the coating and exposing it to high-energy radiation or electron beam through a photomask; optionally heat treating the exposed coating, and developing it with a developer.

In a preferred embodiment, the exposing step is immersion lithography with a liquid having a high refractive index of at least 1.0 interposed between the resist coating and a projection lens.

In another preferred embodiment, the process further comprises the step of applying a protective coating on the resist coating, and the exposing step is immersion lithography with a liquid having a high refractive index of at least 1.0 interposed between the protective coating and a projection lens.

Advantageous Effects of Invention

The fluoroalcohols and fluorinated monomers of the invention are useful as raw materials for the synthesis of polymers, functional materials, pharmaceutical and agricultural chemicals. They are most useful as monomers to produce polymers for the manufacture of radiation-sensitive resist compositions which have high transparency to radiation having a wavelength of up to 500 nm, especially up to 300 nm, and exhibit good development characteristics. Radiation-sensitive resist compositions comprising the polymers as base resin exhibit high resolution and an anti-swelling effect, and prevent dissolution in water as an immersion medium and penetration of water when processed by photolithography, especially immersion lithography. The polymers are advantageously used in resist compositions, especially chemically amplified positive resist compositions for precise micropatterning.

DESCRIPTION OF THE PREFERRED EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. As used herein, the terminology "($C_x$-$C_y$)", as applied to a particular unit, such as, for example, a chemical compound or a chemical substituent group, means having a carbon atom content of from "x" carbon atoms to "y" carbon atoms per such unit.

The abbreviations and acronyms have the following meaning.

Mw: weight average molecular weight

Mn: number average molecular weight

Mw/Mn: molecular weight distribution or dispersity

GPC: gel permeation chromatography

PEB: post-exposure baking

PAG: photoacid generator

PGMEA: propylene glycol monomethyl ether acetate

While a certain compound is herein represented by a chemical formula, many compounds have a chemical structure for which there can exist enantiomers or diastereomers. Unless otherwise stated, each chemical formula collectively represents all such stereoisomers. Such stereoisomers may be used alone or in admixture.

Fluoroalcohol

In a first embodiment of the invention, the fluoroalcohol compound has the general formula (1).

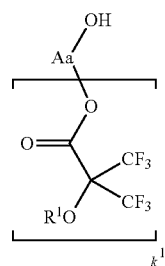

(1)

Herein $R^1$ is hydrogen or a straight, branched or cyclic monovalent $C_1$-$C_{20}$ hydrocarbon group in which any constituent —$CH_2$— moiety may be replaced by —O— or —C(=O)—, Aa is a straight, branched or cyclic ($k^1$+1)-valent $C_1$-$C_{20}$ hydrocarbon or fluorinated hydrocarbon group, and $k^1$ is an integer of 1 to 3.

The monovalent hydrocarbon groups represented by $R^1$ include a variety of protective groups for alcoholic hydroxyl groups. Suitable hydrocarbon groups include groups of the following general formulae (R1-1) and (R1-2), tertiary alkyl groups of 4 to 20 carbon atoms, preferably 4 to 15 carbon atoms, trialkylsilyl groups in which each alkyl moiety has 1 to 5 carbon atoms, oxoalkyl groups of 4 to 15 carbon atoms, and acyl groups of 1 to 10 carbon atoms.

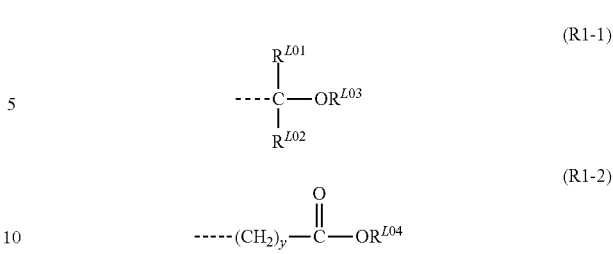

In these formulae and throughout the specification, the broken line denotes a valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of such alkyl groups in which some hydrogen atoms are replaced by hydroxyl, alkoxy, oxo, amino, alkylamino or the like. Illustrative examples are the substituted alkyl groups shown below.

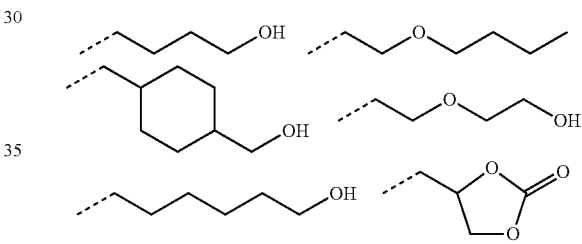

A pair of $R^{L01}$ and $R^{L02}$, $L^{L01}$ and $R^{L03}$, or $R^{L02}$ and $R^{L03}$ may bond together to form a ring with carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (R1-1).

Examples of suitable tertiary alkyl groups represented by $R^1$ or $R^{L04}$ include tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Exemplary acyl groups include formyl, acetyl, ethylcarbonyl, pivaloyl, methoxycarbonyl, ethoxycarbonyl, tert-butoxycarbonyl, trifluoroacetyl, and trichloroacetyl. Letter y is an integer of 0 to 6.

Of the protective groups of formula (R1-1), the straight and branched ones are exemplified by the following groups.

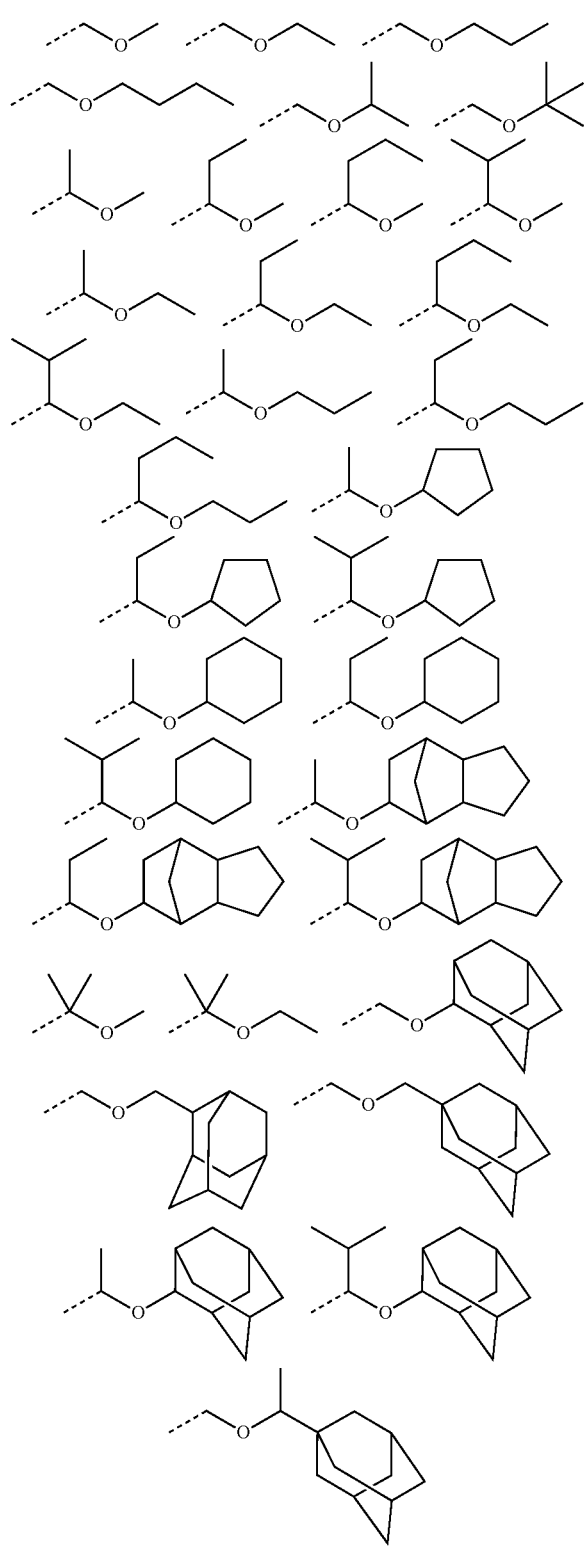

Of the protective groups of formula (R1-1), the cyclic ones are, for example, tetrahydrofuran-2-yl, 2-methyltetrahydrofuran-2-yl, tetrahydropyran-2-yl, and 2-methyltetrahydropyran-2-yl.

Examples of the protective groups of formula (R1-2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

In formula (1), Aa is a straight, branched or cyclic ($k^1+1$)-valent $C_1$-$C_{20}$ hydrocarbon or fluorinated hydrocarbon group. Examples of the straight, branched or cyclic ($k^1+1$)-valent $C_1$-$C_{20}$ hydrocarbon group are shown below.

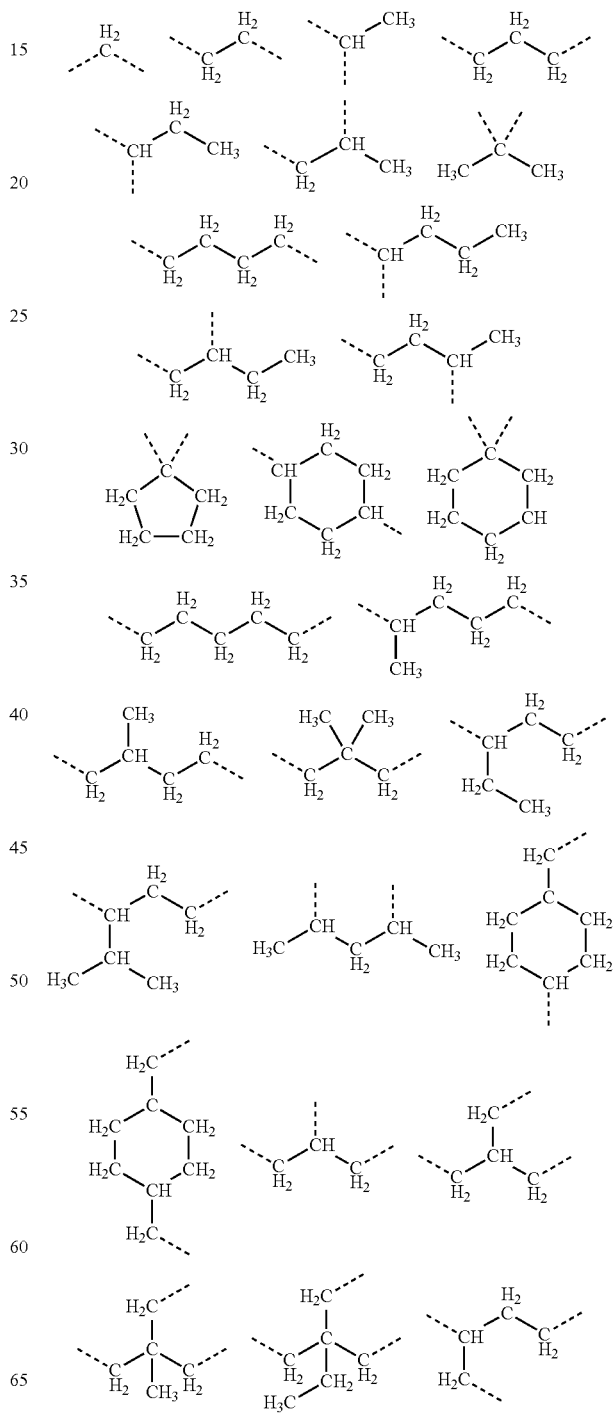

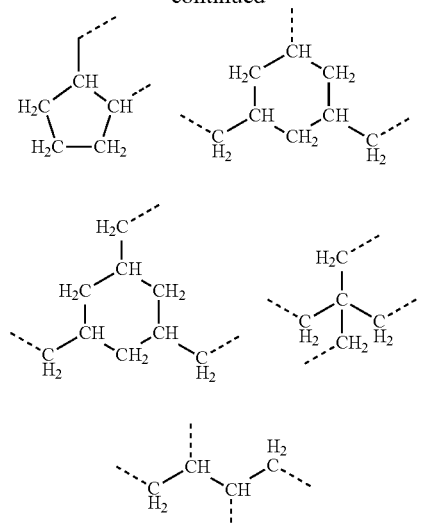

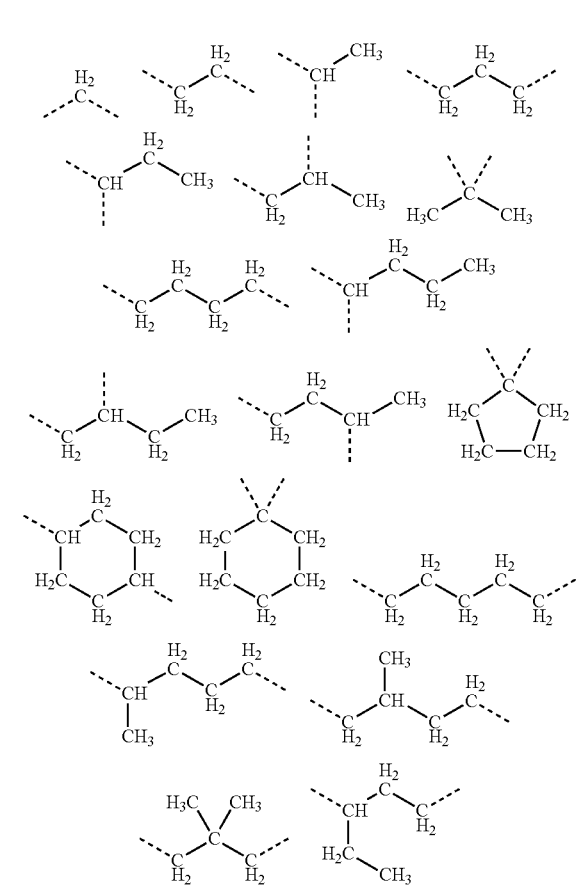

Examples of the straight, branched or cyclic ($k^1+1$)-valent $C_1$-$C_{20}$ fluorinated hydrocarbon group include substituted forms of the foregoing hydrocarbon groups in which some or all hydrogen atoms are replaced by fluorine atoms.

Fluorinated Monomer

In a second embodiment of the invention, a fluorinated monomer is obtained by esterification of the fluoroalcohol having formula (1) and has the general formula (2).

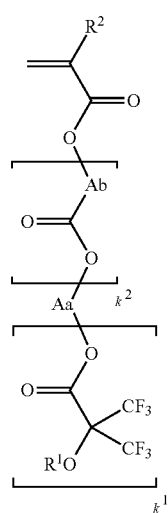

(2)

Herein $R^1$ is hydrogen or a straight, branched or cyclic monovalent $C_1$-$C_{20}$ hydrocarbon group in which any constituent —$CH_2$— moiety may be replaced by —O— or —C(=O)—, $R^2$ is hydrogen, fluorine, methyl or trifluoromethyl, Aa is a straight, branched or cyclic ($k^1+1$)-valent $C_1$-$C_{20}$ hydrocarbon or fluorinated hydrocarbon group, Ab is a straight, branched or cyclic divalent $C_1$-$C_6$ hydrocarbon group, $k^1$ is an integer of 1 to 3, and $k^2$ is 0 or 1.

The groups represented by $R^1$ and Aa are illustrated above. Ab is a straight, branched or cyclic divalent $C_1$-$C_6$ hydrocarbon group, examples of which are shown below.

Illustrative, non-limiting examples of the compound having formula (2) are given below.

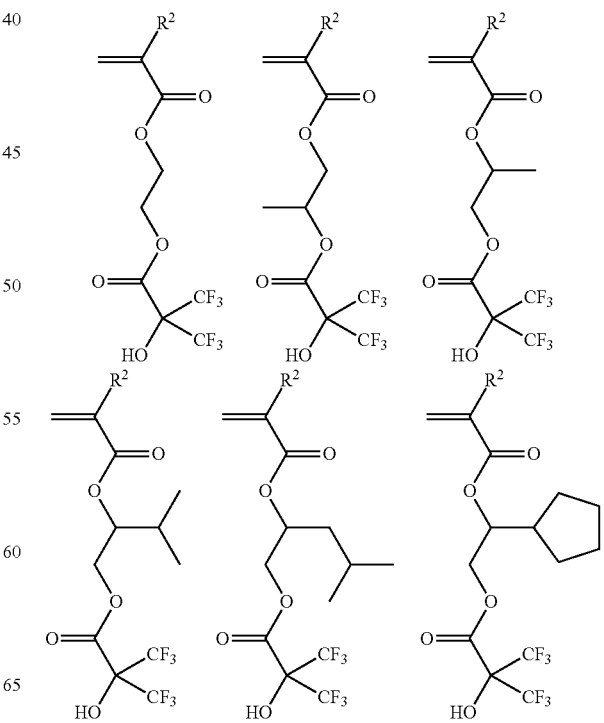

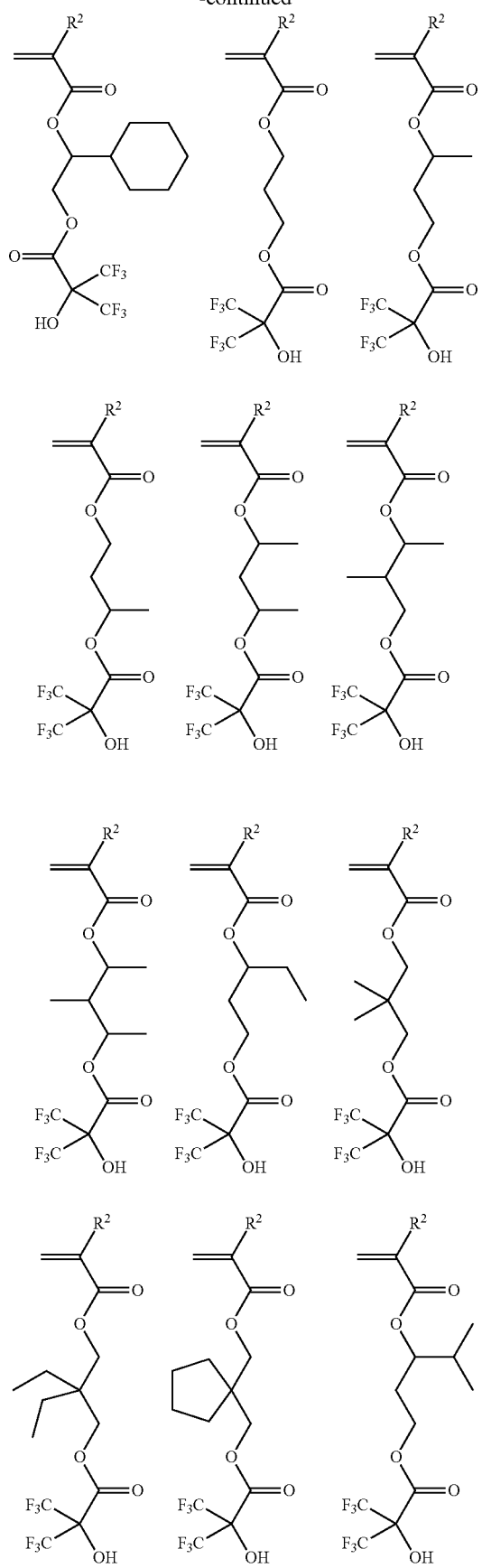
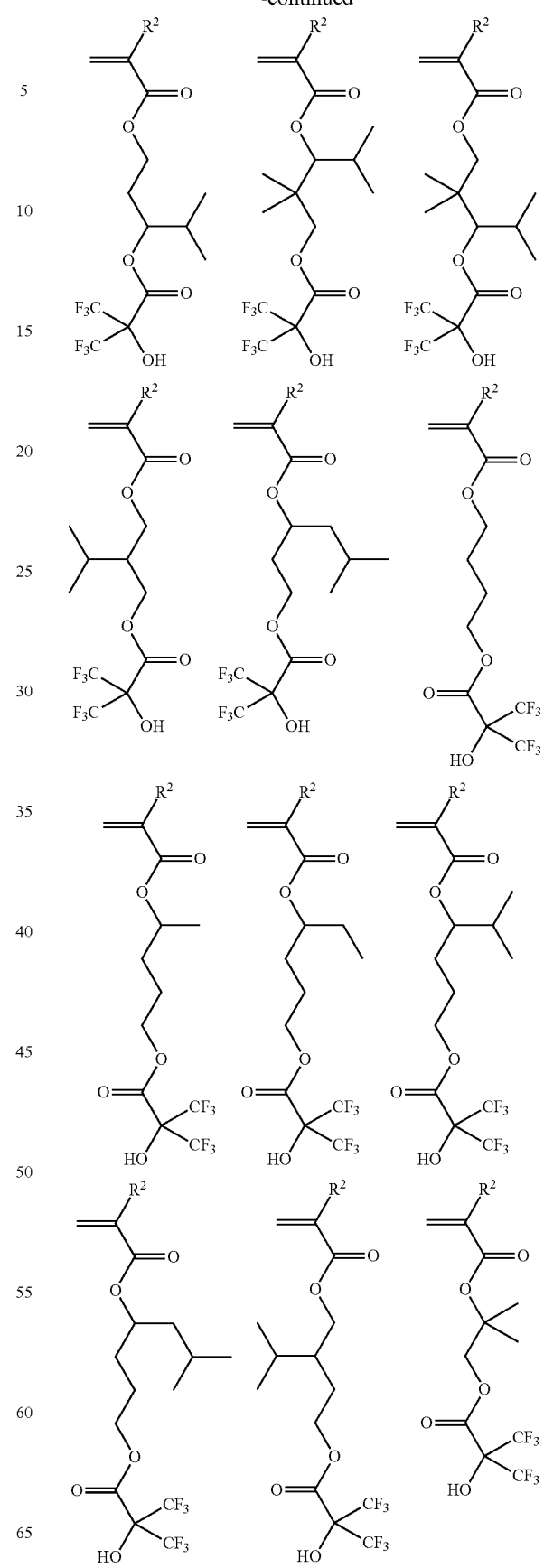

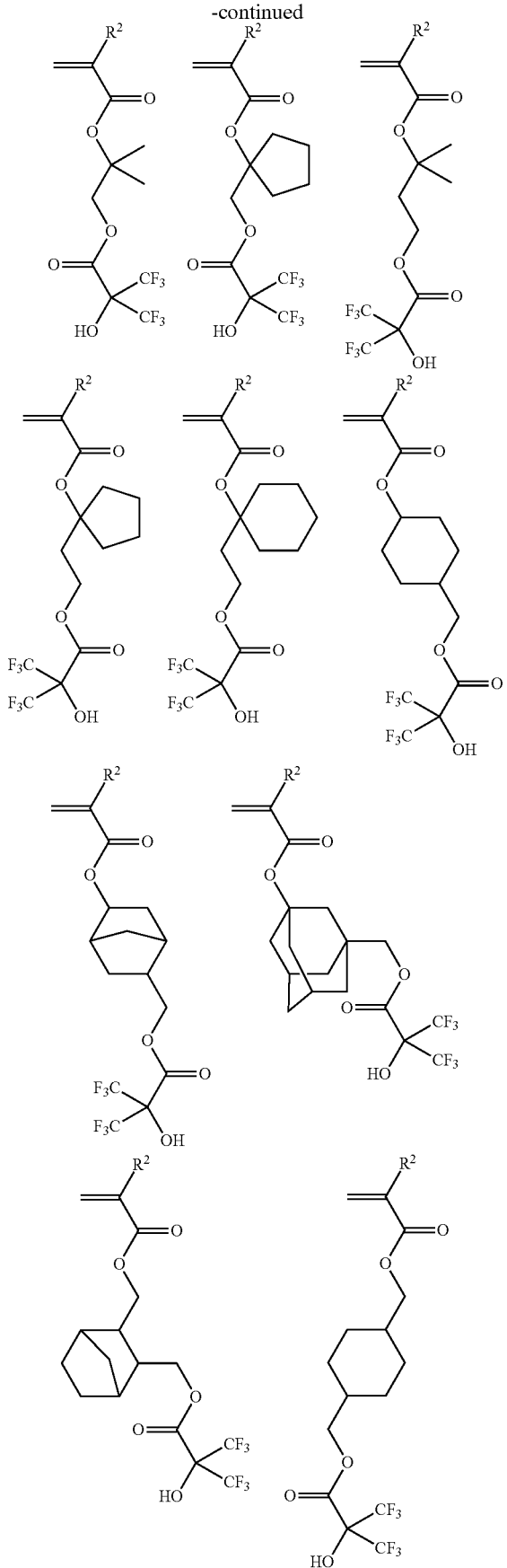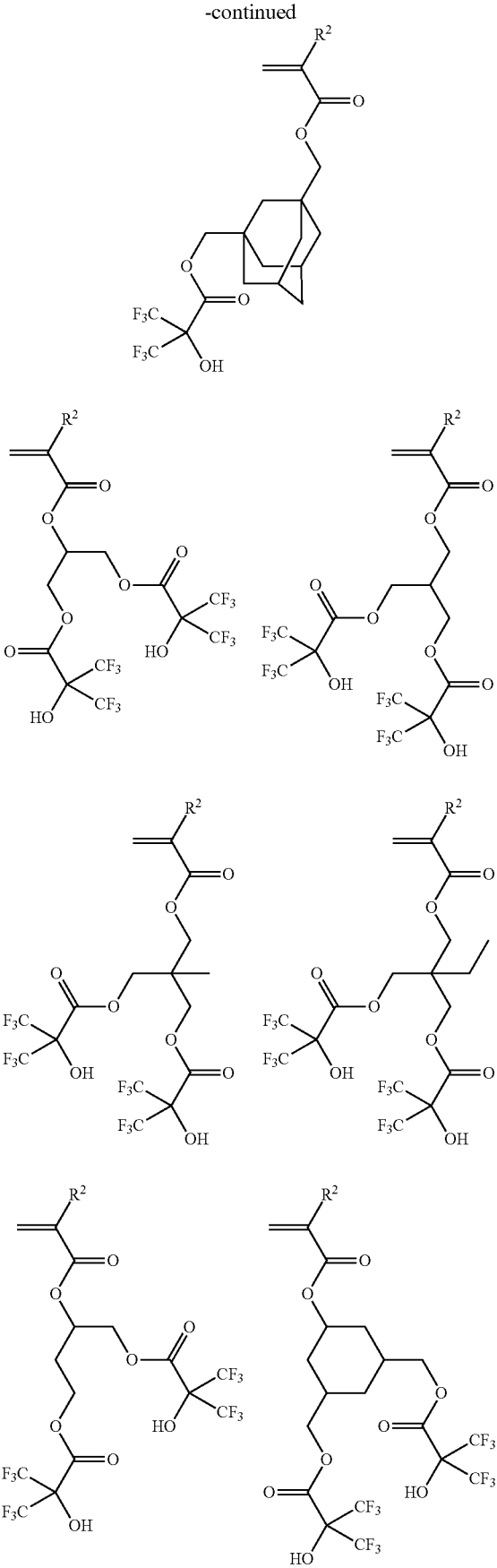

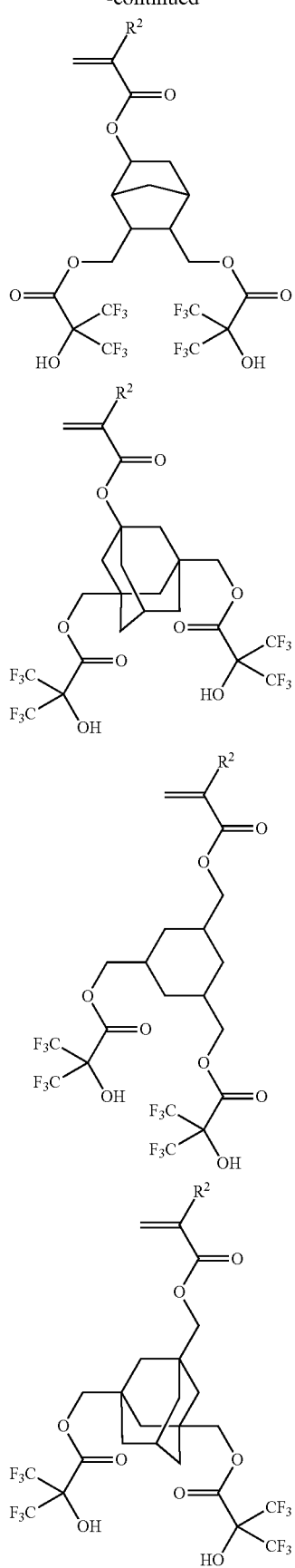
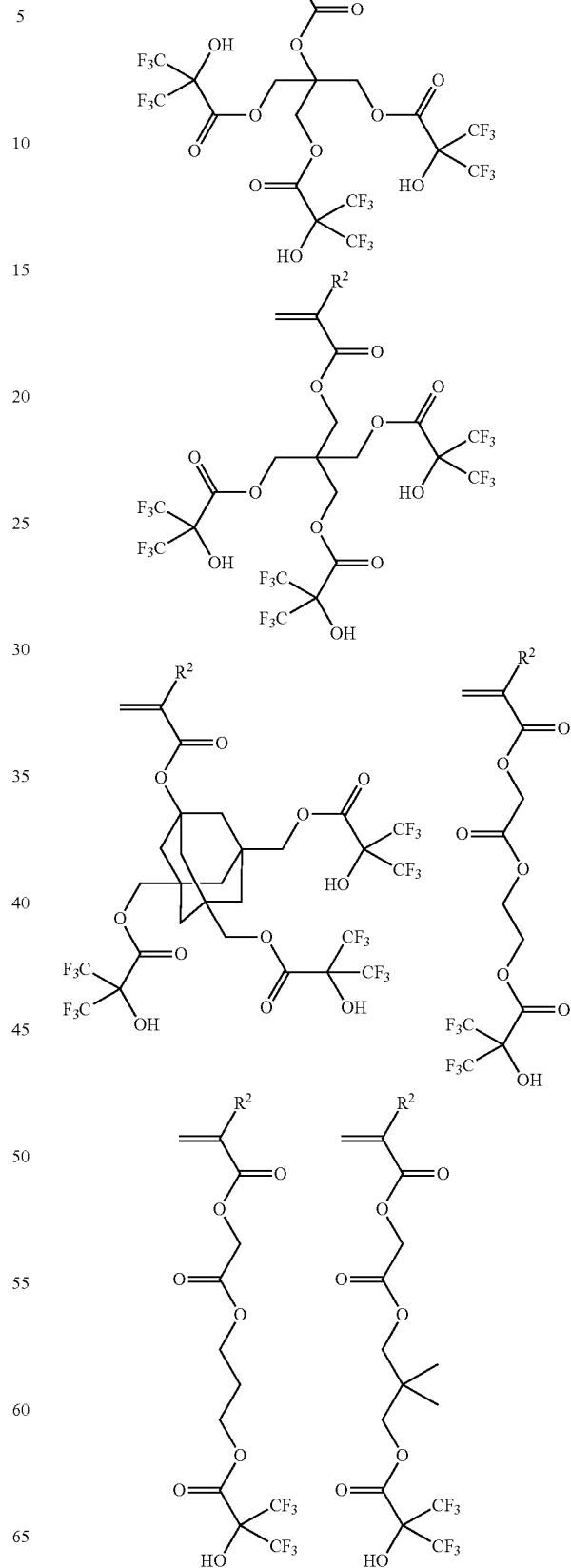

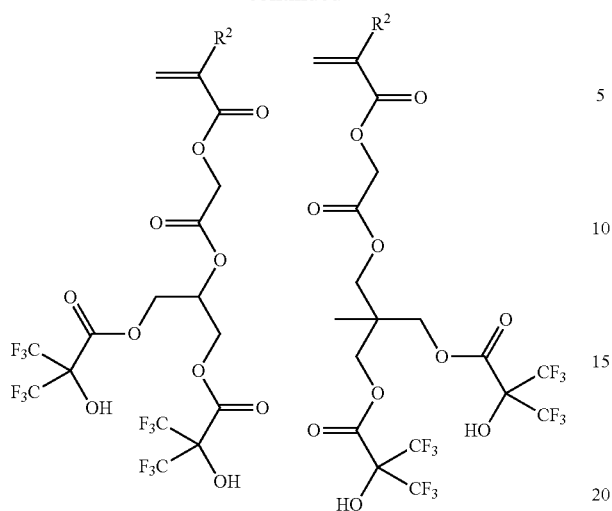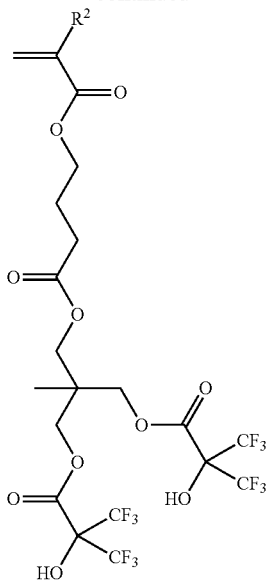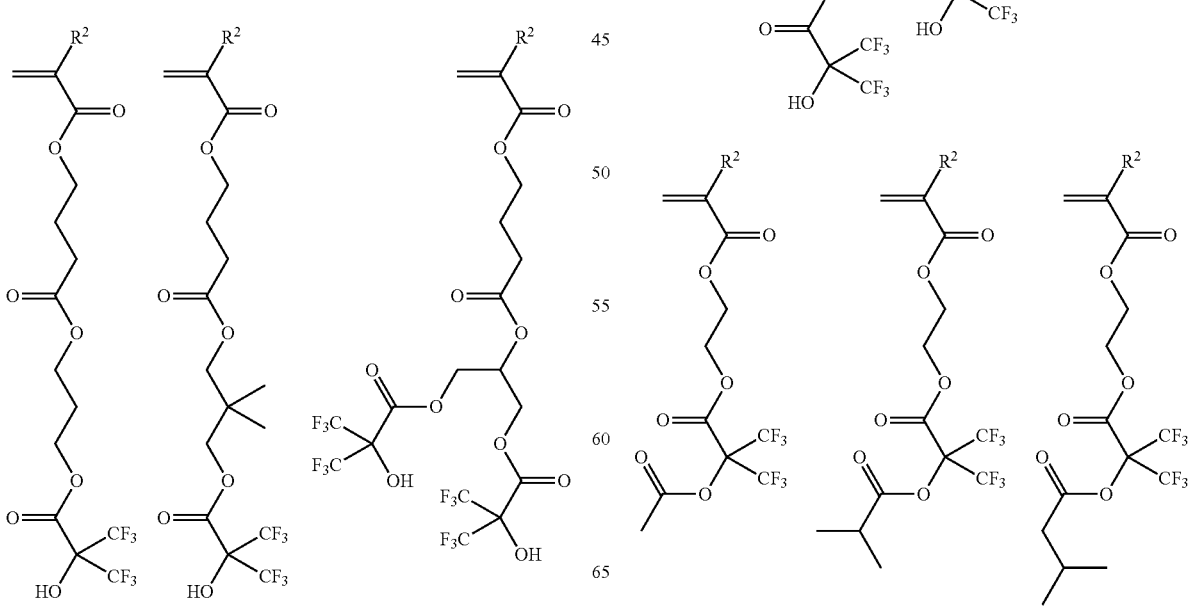

-continued
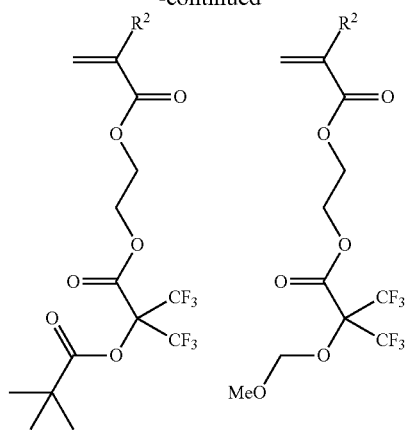
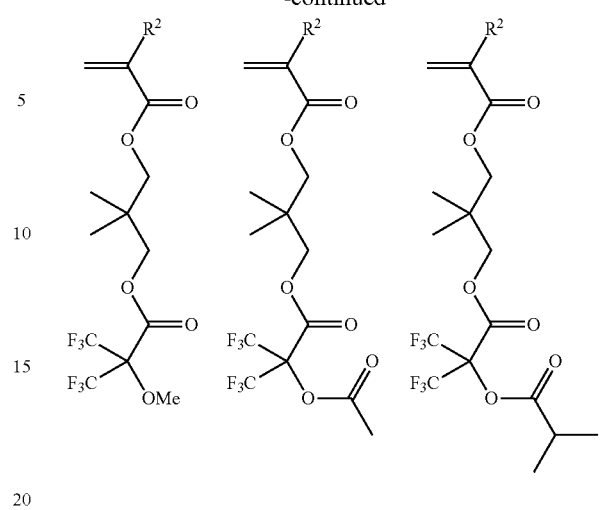
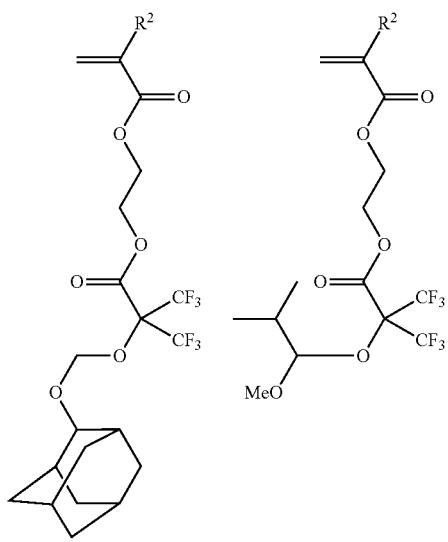
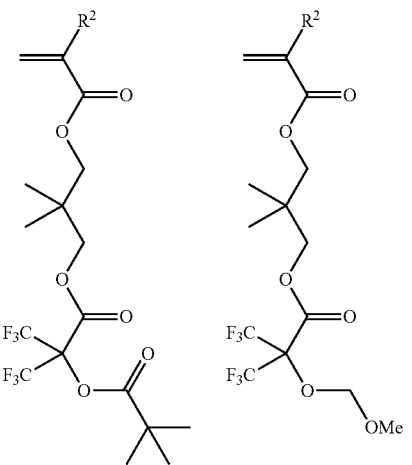
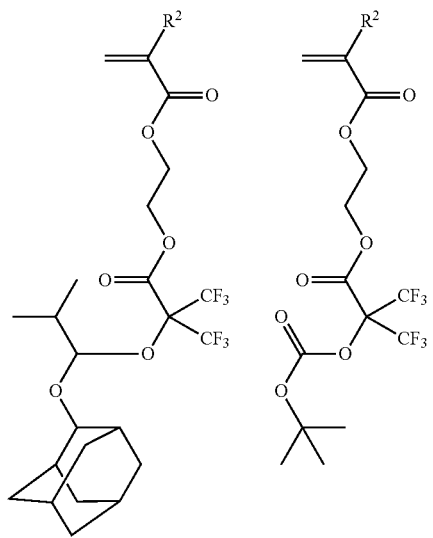
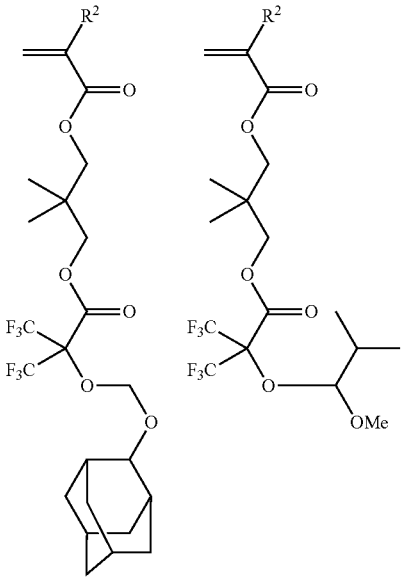

-continued
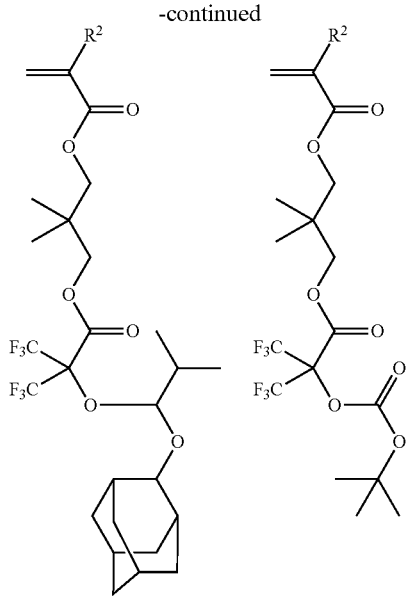
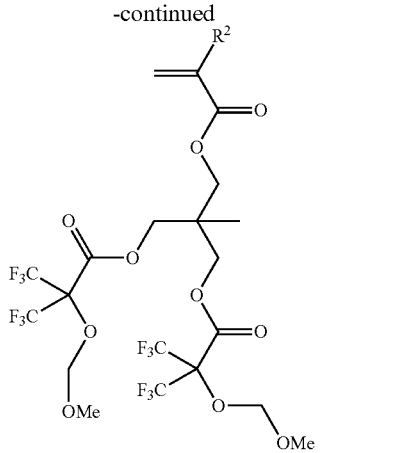
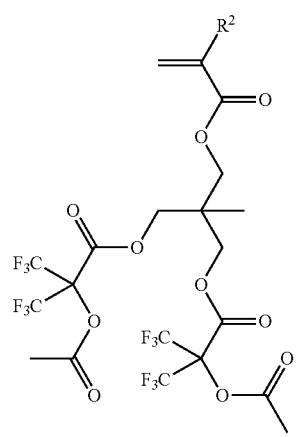
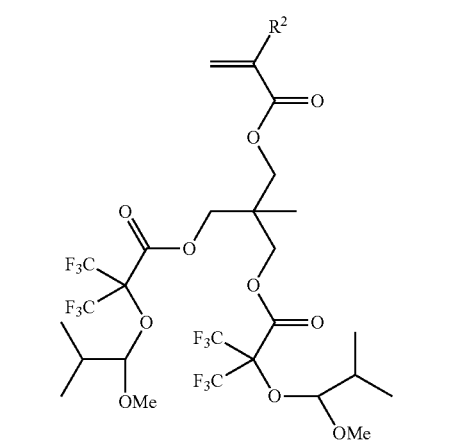
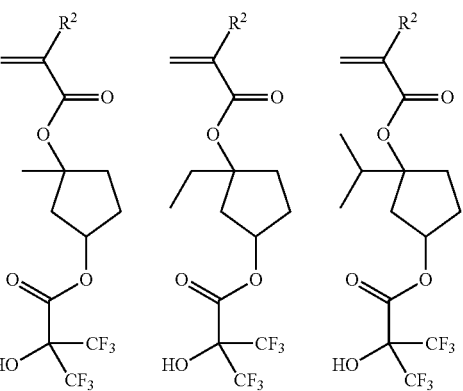
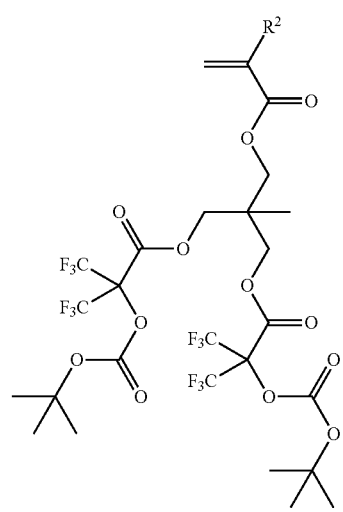
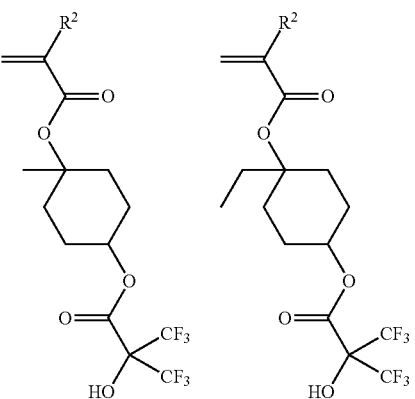

-continued
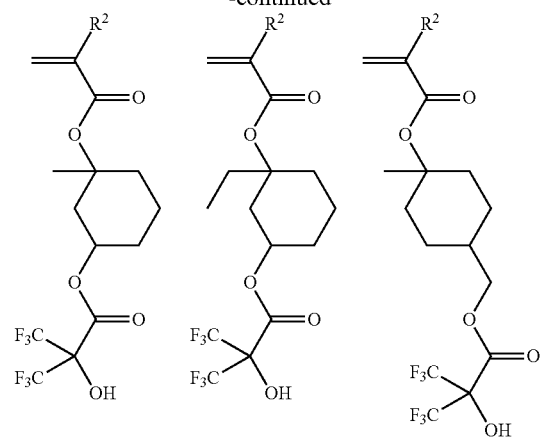
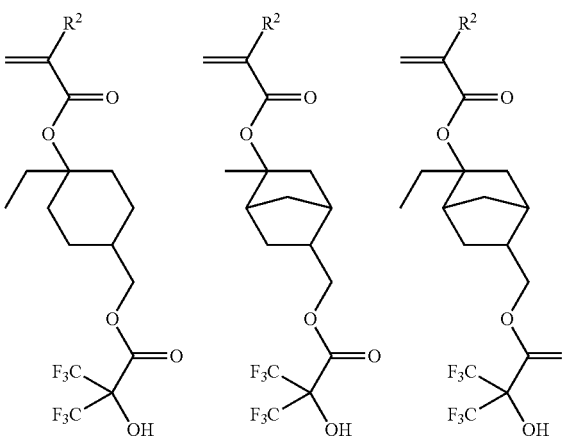
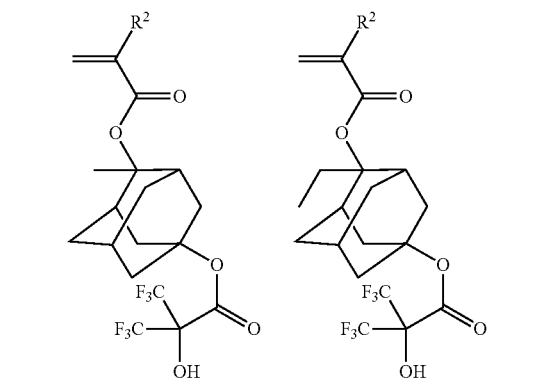
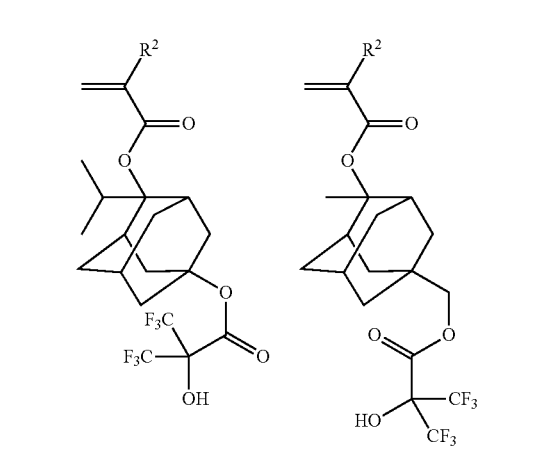
-continued
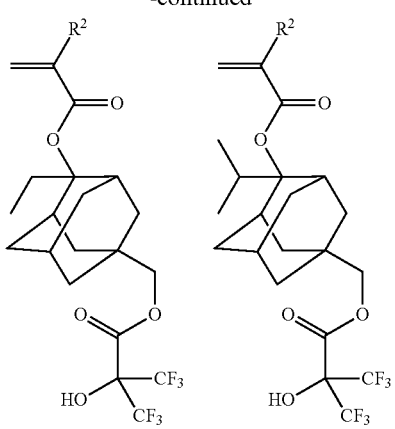
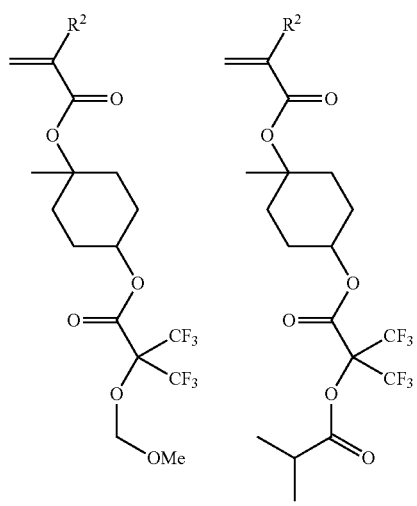
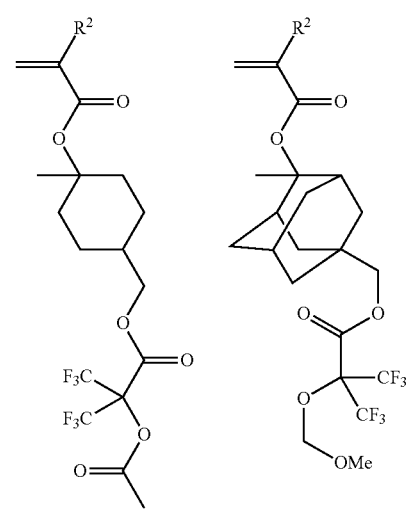

-continued

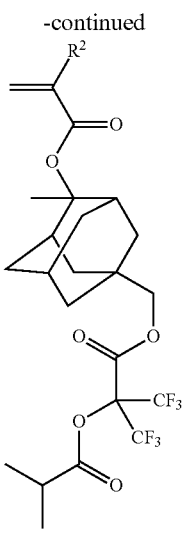

Note that $R^2$ is as defined above and Me stands for methyl.

The fluoroalcohol of formula (1) can be prepared according to the following reaction scheme, for example, although its preparation is not limited thereto.

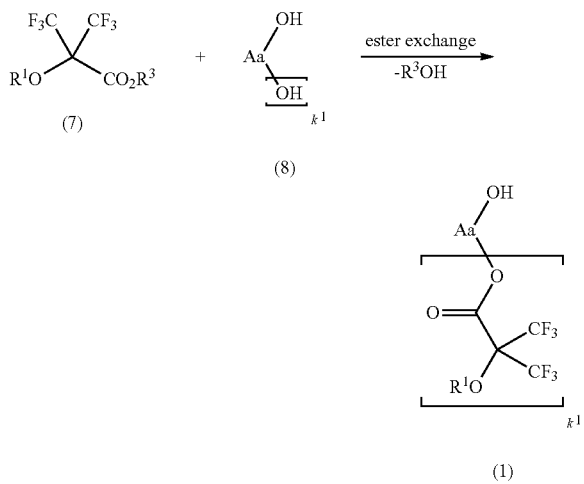

Herein $R^1$, Aa and $k^1$ are as defined above, $R^3$ is hydrogen or a straight, branched or cyclic, monovalent $C_1$-$C_6$ hydrocarbon group.

Specifically, fluoroalcohol (1) can be synthesized by ester exchange reaction of a fluorinated compound (7) with a polyhydric alcohol compound (8). It is noted that a 3,3,3-trifluoro-2-hydroxy-2-(trifluoromethyl)propionic acid derivative having formula (7) may be obtained by starting with octafluoroisobutylene which is a by-product during the synthesis of hexafluoropropene, for example. Since the starting reactant is a by-product of a commercial product, the fluorinated compound (7) is available in plenty at a relatively low cost.

Although the reaction may be carried out in a solventless system, a solvent may be used in an auxiliary manner. Examples of the solvent, if used, include ethers such as tetrahydrofuran, diethyl ether, di-n-butyl ether, and 1,4-dioxane, and hydrocarbons such as n-hexane, n-heptane, benzene, toluene, xylene, and cumene, which may be used alone or in admixture. Suitable catalysts include metal alkoxides such as sodium methoxide, sodium ethoxide, potassium t-butoxide, magnesium ethoxide, titanium(IV) methoxide, titanium(IV) ethoxide, and titanium(IV) isopropoxide, organic amines such as triethylamine, N,N-dimethylaminopyridine, and 1,8-diazabicyclo[5.4.0]-7-undecene, and inorganic bases such as sodium hydroxide, potassium carbonate, and sodium carbonate, which may be used alone or in admixture. An appropriate amount of the catalyst used is 0.001 to 5.0 moles, more preferably 0.001 to 0.1 mole per mole of fluorinated compound (7). Although the reaction temperature may widely vary with other reaction conditions, it is preferably in a range of 50 to 200° C. Reaction may be effected at such a temperature while $R^3OH$ formed during the reaction may be distilled off. The reaction time is determined as appropriate by monitoring the reaction process by gas chromatography (GC) or silica gel thin-layer chromatography (TLC) because it is desirable from the yield aspect to drive the reaction to completion. Usually the reaction time is about 0.5 to about 20 hours. The desired fluoroalcohol (1) may be obtained from the reaction mixture by ordinary aqueous work-up. If necessary, the compound may be purified by standard techniques like distillation, recrystallization, and chromatography.

The fluorinated monomer of formula (2) may be prepared according to the reaction schemes shown below, through step i) when $k^2$ in formula (2) is 0, or through step ii) or steps iii) and iv) when $k^2$ in formula (2) is 1, although the preparation method is not limited thereto.

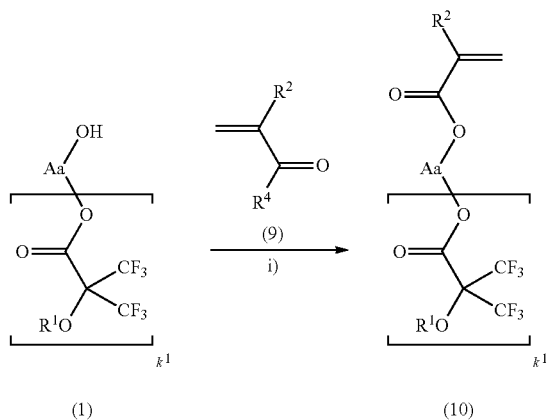

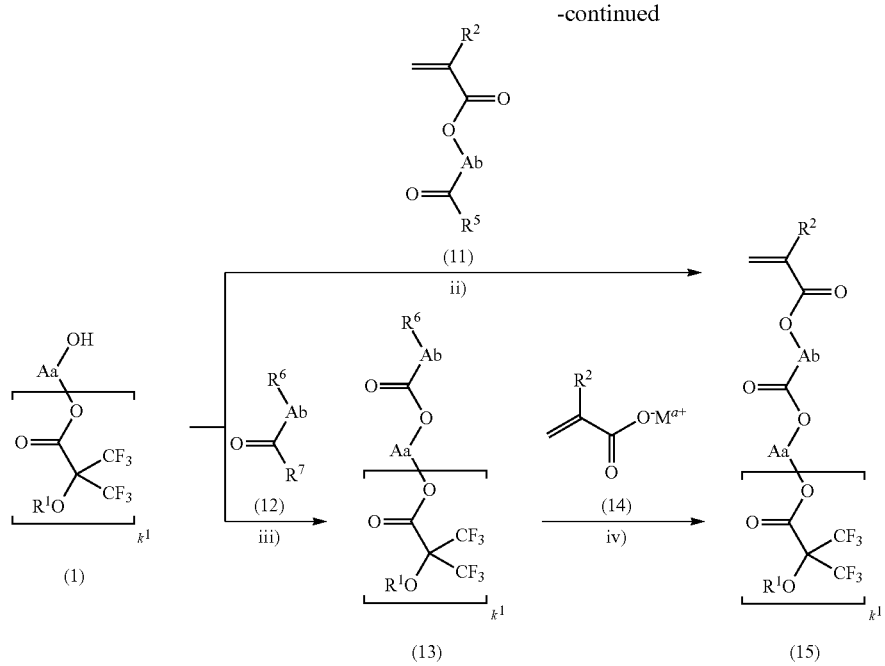

Herein $R^1$, $R^2$, Aa, Ab, $k^1$ and $k^2$ are as defined above. $R^4$ is halogen, hydroxyl or $-OR^8$ wherein $R^8$ is methyl, ethyl or a group of the formula (16) below.

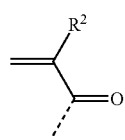

(16)

$R^5$ is halogen, hydroxyl or $-OR^9$ wherein $R^9$ is methyl, ethyl or a group of the formula (17) below.

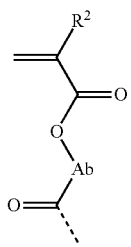

(17)

$R^6$ is halogen. $R^7$ is halogen, hydroxyl or $-OR^{10}$ wherein $R^{10}$ is methyl, ethyl or a group of the formula (18) below.

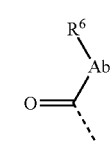

(18)

$M^a$ is Li, Na, K, $Mg_{1/2}$, $Ca_{1/2}$ or substituted or unsubstituted ammonium.

Step i) is reaction between an esterifying agent (9) and an alcohol (1) to form a monomer (10), i.e., fluorinated monomer having formula (2). The reaction may readily proceed in a well-known manner. The esterifying agent (9) is preferably an acid chloride of formula (9) wherein $R^4$ is chlorine or a carboxylic acid anhydride of formula (9) wherein $R^4$ is $OR^8$ wherein $R^8$ has the following formula (16).

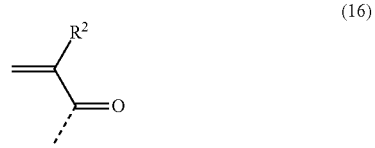

(16)

In one procedure using an acid chloride, the alcohol compound (1), the corresponding acid chloride such as methacrylic acid chloride, and a base such as triethylamine, pyridine, or 4-dimethylaminopyridine are successively or simultaneously added to a solventless system or to a solvent such as methylene chloride, acetonitrile, toluene, or hexane, while the reaction system may be cooled or heated as desired. In another procedure using a carboxylic anhydride, the alcohol compound (1) and the corresponding carboxylic anhydride such as methacrylic anhydride in a solvent such as toluene or hexane are heated in the presence of an acid catalyst while water formed during reaction may be removed out of the system if desired. Suitable acid catalysts used herein include mineral acids such as hydrochloric acid, sulfuric acid, nitric acid and perchloric acid and organic acids such as methanesulfonic acid, trifluoromethanesulfonic acid, p-toluenesulfonic acid, and benzenesulfonic acid.

Step ii) is reaction between an esterifying agent (11) and an alcohol (1) to form a monomer (15), i.e., fluorinated monomer having formula (2). The reaction may readily proceed in a well-known manner. The esterifying agent (11) is preferably an acid chloride of formula (11) wherein $R^5$ is chlorine or a carboxylic acid anhydride of formula (11) wherein $R^5$ is $OR^9$ wherein $R^9$ has the following formula (17).

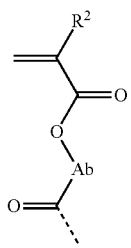

(17)

In one procedure using an acid chloride, the alcohol compound (1), the corresponding acid chloride such as methacryloyloxyacetic acid chloride, and a base such as triethylamine, pyridine, or 4-dimethylaminopyridine are successively or simultaneously added to a solventless system or to a solvent such as methylene chloride, acetonitrile, toluene, or hexane, while the reaction system may be cooled or heated as desired. In another procedure using a carboxylic anhydride, the alcohol compound (1) and the corresponding carboxylic anhydride such as methacryloyloxyacetic anhydride in a solvent such as toluene or hexane are heated in the presence of an acid catalyst while water formed during reaction may be removed out of the system if desired. Suitable acid catalysts used herein include mineral acids such as hydrochloric acid, sulfuric acid, nitric acid and perchloric acid and organic acids such as methanesulfonic acid, trifluoromethanesulfonic acid, p-toluenesulfonic acid, and benzenesulfonic acid.

Step iii) is reaction between an esterifying agent (12) and an alcohol compound (1) to form a halo ester compound (13). The reaction may readily proceed in a well-known manner. The esterifying agent (12) is preferably an acid chloride of formula (12) wherein $R^7$ is chlorine or a carboxylic acid of formula (12) wherein $R^7$ is hydroxyl. In one procedure using an acid chloride, the alcohol compound (1), the corresponding acid chloride such as 2-chloroacetic acid chloride or 4-chlorobutyric acid chloride, and a base such as triethylamine, pyridine, or 4-dimethylaminopyridine are successively or simultaneously added to a solventless system or to a solvent such as methylene chloride, toluene, hexane, diethyl ether, tetrahydrofuran or acetonitrile, while the reaction system may be cooled or heated as desired. In another procedure using a carboxylic acid, the alcohol compound (1) and the corresponding carboxylic acid such as 2-chloroacetic acid or 4-chlorobutyric acid in a solvent such as toluene or hexane are heated in the presence of an acid catalyst while water formed during reaction may be removed out of the system if desired. Suitable acid catalysts used herein include mineral acids such as hydrochloric acid, sulfuric acid, nitric acid and perchloric acid and organic acids such as p-toluenesulfonic acid and benzenesulfonic acid.

Step iv) is reaction between the halo-ester compound (13) and a carboxylic acid salt (14) to form a monomer (15), i.e., fluorinated monomer having formula (2). The reaction may be effected by a standard technique. The carboxylic acid salt (14) may be any of commercially available carboxylic acid salts such as metal salts of various carboxylic acids as purchased. Alternatively, the carboxylic acid salt may be formed within the reaction system from a corresponding carboxylic acid such as methacrylic acid or acrylic acid and a base. An appropriate amount of carboxylic acid salt (14) used is 0.5 to 10 moles, more preferably 1.0 to 3.0 moles per mole of the reactant, halo-ester compound (13). If the amount of carboxylic acid salt (14) is less than 0.5 mole, a larger fraction of the reactant may be left unreacted, leading to a substantial drop of percent yield. More than 10 moles of carboxylic acid salt (14) may be uneconomical due to increased material costs and reduced pot yields. In the other embodiment where a carboxylic acid salt is formed within the reaction system from a corresponding carboxylic acid and a base, examples of the base used herein include amines such as ammonia, triethylamine, pyridine, lutidine, collidine, and N,N-dimethylaniline; hydroxides such as sodium hydroxide, potassium hydroxide, and tetramethylammonium hydroxide; carbonates such as potassium carbonate and sodium hydrogen carbonate; metals such as sodium; metal hydrides such as sodium hydride; metal alkoxides such as sodium methoxide and potassium tert-butoxide; organometallics such as butyllithium and ethylmagnesium bromide; and metal amides such as lithium diisopropylamide. One or more bases may be selected from these examples. The amount of the base used is preferably 0.2 to 10 moles, and more preferably 0.5 to 2.0 moles per mole of the corresponding carboxylic acid. If the amount of the base is less than 0.2 mole, a large fraction of the carboxylic acid may become a waste, which is uneconomical. More than 10 moles of the base may lead to a substantial drop of yield due to increased side reactions.

Suitable solvents which can be used in step iv) include hydrocarbons such as toluene, xylene, hexane and heptane; chlorinated solvents such as methylene chloride, chloroform and dichloroethane; ethers such as diethyl ether, tetrahydrofuran, and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide, and dimethyl sulfoxide; and water, which may be used alone or in admixture. To the reaction, a phase transfer catalyst such as tetrabutylammonium hydrogensulfate may be added. The amount of phase transfer catalyst added is preferably 0.0001 to 1.0 mole, and more preferably 0.001 to 0.5 mole per mole of the reactant, halo-ester compound (13). Less than 0.0001 mole of the catalyst may fail to achieve the catalytic effect whereas more than 1.0 mole of the catalyst may be uneconomical due to increased material costs.

The temperature of esterifying reaction is preferably in the range of −70° C. to the boiling point of the solvent used. An appropriate temperature may be selected in accordance with other reaction conditions, although it is most often in the range of 0° C. to the boiling point of the solvent used. Since noticeable side reactions occur at higher temperatures, it is important for gaining higher yields that the reaction run at a temperature which is low, but enough to ensure a practically acceptable reaction rate. Also for higher yields, the reaction time is preferably determined by monitoring the reaction process by thin-layer chromatography (TLC) or gas chromatography (GC). Usually the reaction time is about 30 minutes to about 40 hours. The desired monomer (15), i.e., fluorinated monomer having formula (2) may be obtained from the reaction mixture by ordinary aqueous work-up. If necessary, the compound may be purified by standard techniques like distillation, recrystallization and chromatography.

It is noted that JP-A 2003-040840, JP-A 2007-204385 and JP 4475435 disclose a compound having a partial structure —C(CF$_3$)$_2$OH, like the fluorinated monomer of the invention. The fluorinated monomer of the invention is characterized in that the carbon atom having trifluoromethyl substituted thereon is further substituted with an electron attractive group of the following formula (19):

(19)

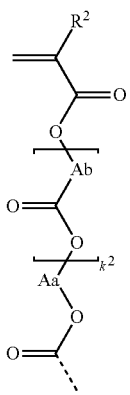

so that the hydroxyl group may exhibit a stronger acidity. In this sense, the inventive monomer fulfills the requirements of novelty and inventive step over the cited patent documents.

Polymer

The polymer or high molecular weight compound of the invention is characterized by comprising recurring units derived from the fluorinated monomer of formula (2).

The recurring units derived from the fluorinated monomers of formula (2) include those having the general formula (2a).

(2a)

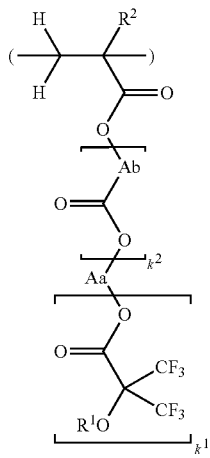

Herein $R^1$, $R^2$, Aa, Ab, $k^1$ and $k^2$ are as defined above.

In addition to the recurring units having formula (2a), the polymers of the invention may comprise recurring units of at least one type selected from the following general formulas (2A) to (2D).

(2A)

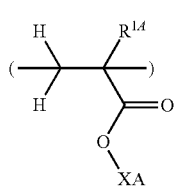

(2B)

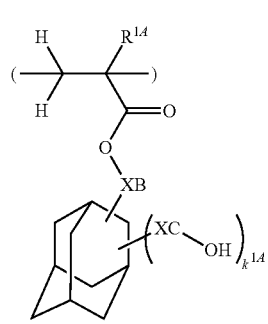

(2C)

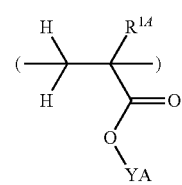

(2D)

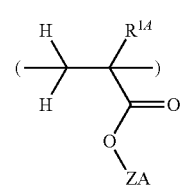

Herein $R^{14}$ is hydrogen, fluorine, methyl or trifluoromethyl, XA is an acid labile group, XB and XC are each independently a single bond or a straight or branched divalent $C_1$-$C_4$ hydrocarbon group (typically alkylene), YA is a substituent group having lactone structure, ZA is hydrogen, a $C_1$-$C_{15}$ fluoroalkyl group or a $C_1$-$C_{15}$ fluoroalcohol-containing substituent group, and $k^{14}$ is an integer of 1 to 3.

Under the action of acid, a polymer comprising recurring units of formula (2A) is decomposed to generate carboxylic acid, turning to be an alkali soluble polymer. The acid labile group represented by XA may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

(L1)

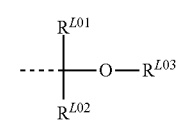

(L2)

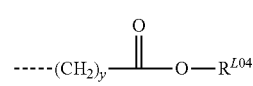

(L3)

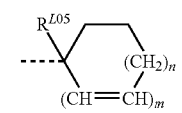

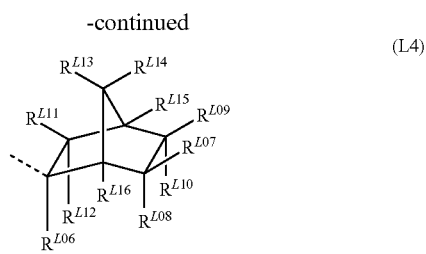
(L4)

In these formulae, the broken line denotes a valence bond. In formula (L1), $R^{L01}$ and $R^{L02}$ are hydrogen or straight, branched or cyclic alkyl groups of 1 to 18 carbon atoms, preferably 1 to 10 carbon atoms. $R^{L03}$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of such alkyl groups in which some hydrogen atoms are replaced by hydroxyl, alkoxy, oxo, amino, alkylamino or the like. $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). $R^{L05}$ is an optionally substituted, straight, branched or cyclic $C_1$-$C_{10}$ alkyl group or an optionally substituted $C_6$-$C_{20}$ aryl group. $R^{L06}$ is an optionally substituted, straight, branched or cyclic $C_1$-$C_{10}$ alkyl group or an optionally substituted $C_6$-$C_{20}$ aryl group. $R^{L07}$ to $R^{L16}$ independently represent hydrogen or optionally substituted monovalent hydrocarbon groups of 1 to 15 carbon atoms. Letter y is an integer of 0 to 6, m is equal to 0 or 1, n is equal to 0, 1, 2 or 3, and 2m+n is equal to 2 or 3.

In formula (L1), examples of the alkyl group represented by $R^{L01}$ and $R^{L02}$ include methyl, ethyl, propyl, isopropyl, n-butyl, sec-butyl, tert-butyl, cyclopentyl, cyclohexyl, 2-ethylhexyl, n-octyl, and adamantyl.

$R^{L03}$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of such alkyl groups in which some hydrogen atoms are replaced by hydroxyl, alkoxy, oxo, amino, alkylamino or the like. Suitable alkyl groups are as exemplified above for $R^{L01}$ and $R^{L02}$. Suitable substituted alkyl groups are shown below.

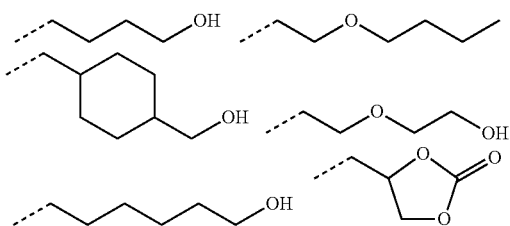

A pair of $R^{L01}$ and $R^{L02}$, $R^{L01}$ and $R^{L03}$, or $R^{L02}$ and $R^{L03}$ may form a ring with carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

In formula (L2), $R^{L04}$ is a tertiary alkyl group, trialkylsilyl group, oxoalkyl group, or group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl.

In formula (L3), $R^{L05}$ is an optionally substituted, straight, branched or cyclic $C_1$-$C_{10}$ alkyl group or optionally substituted $C_6$-$C_{20}$ aryl group. Examples of the optionally substituted alkyl group include straight, branched or cyclic alkyl groups such as methyl, ethyl, propyl, isopropyl, n-butyl, sec-butyl, tert-butyl, tert-amyl, n-pentyl, n-hexyl, cyclopentyl, cyclohexyl, and bicyclo[2.2.1]heptyl, and substituted forms of such groups in which some hydrogen atoms are substituted by hydroxyl, alkoxy, carboxy, alkoxycarbonyl, oxo, amino, alkylamino, cyano, mercapto, alkylthio, sulfo or other radicals or in which a methylene moiety is replaced by an oxygen or sulfur atom. Exemplary aryl groups are phenyl, methylphenyl, naphthyl, anthryl, phenanthryl, and pyrenyl.

In formula (L4), $R^{L06}$ is an optionally substituted, straight, branched or cyclic $C_1$-$C_{10}$ alkyl group or optionally substituted $C_6$-$C_{20}$ aryl group, examples of which are the same as exemplified for $R^{L05}$.

Examples of the monovalent $C_1$-$C_{15}$ hydrocarbon groups of $R^{L07}$ to $R^{L16}$ include straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxy, alkoxycarbonyl, oxo, amino, alkylamino, cyano, mercapto, alkylthio, sulfo or other radicals.

Alternatively, $R^{L07}$ to $R^{L16}$, taken together, form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group (typically alkylene) when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

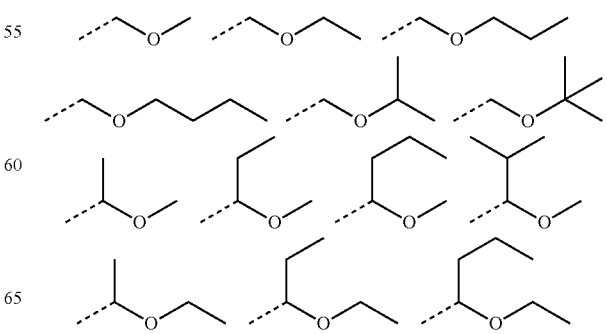

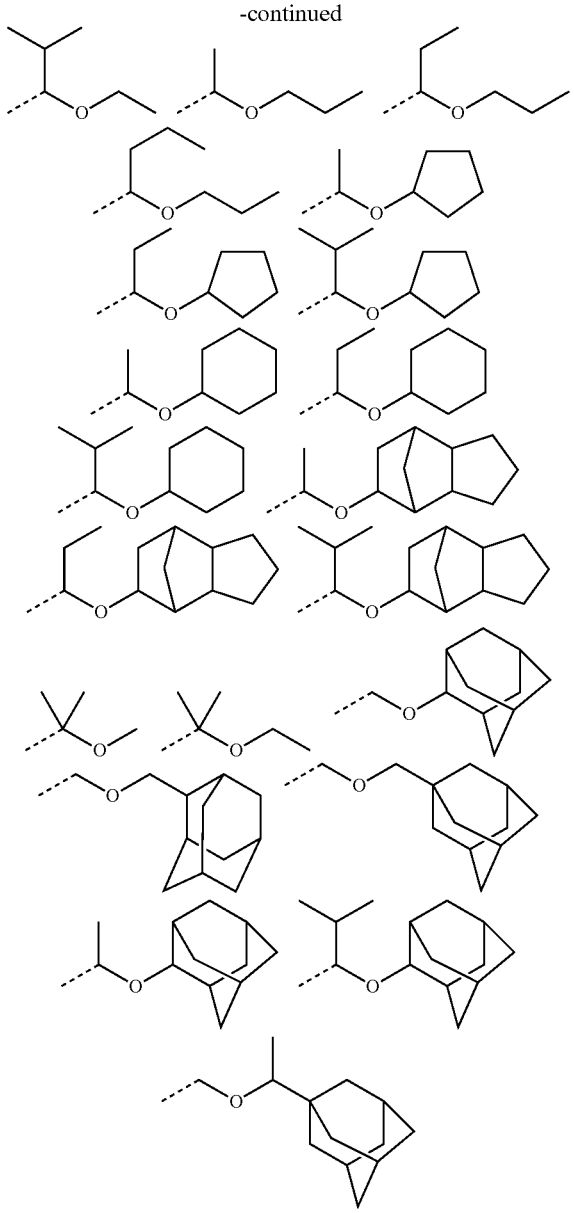

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-(bicyclo[2.2.1]heptan-2-yl)cyclopentyl, 1-(7-oxabicyclo[2.2.1]heptan-2-yl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulas (L4-1) to (L4-4) are preferred.

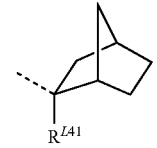
(L4-1)

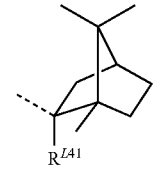
(L4-2)

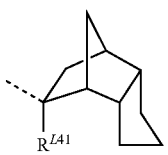
(L4-3)

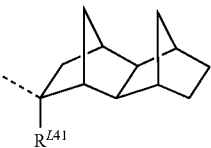
(L4-4)

In formulas (L4-1) to (L4-4), the broken line denotes a bonding site and direction. $R^{L41}$ is each independently a monovalent hydrocarbon group, typically straight, branched or cyclic $C_1$-$C_{10}$ alkyl group such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

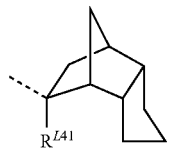
(L4-3-1)

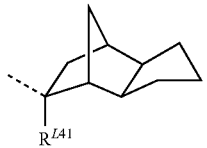
(L4-3-2)

$R^{L41}$ is as defined above.

Similarly, the general formula (L4-4) represents one or a mixture of two or more selected from groups having the following general formulas (L4-4-1) to (L4-4-4).

(L4-4-1)
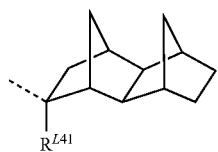

(L4-4-2)
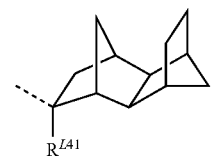

(L4-4-3)
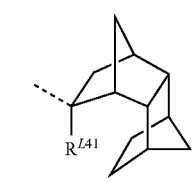

(L4-4-4)
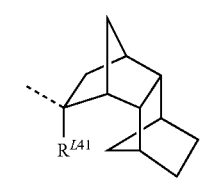

$R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

(L4-1-endo)
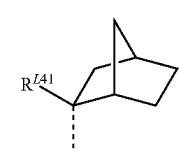

(L4-2-endo)
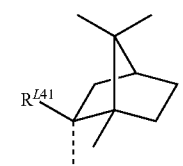

(L4-3-endo)
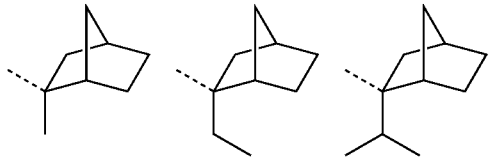

(L4-4-endo)
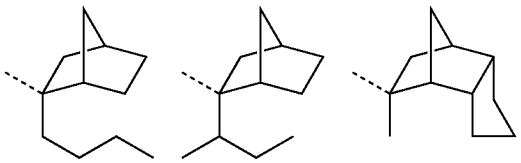

$R^{L41}$ is as defined above.

Illustrative examples of the acid labile group of formula (L4) are given below.

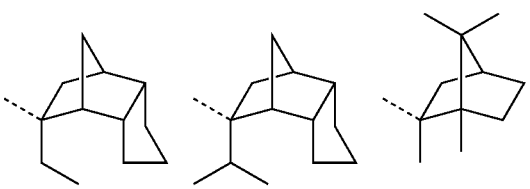

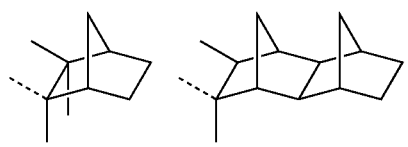

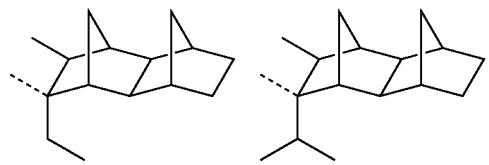

Examples of the tertiary alkyl groups of 4 to 20 carbon atoms, trialkylsilyl groups in which each alkyl moiety has 1 to 6 carbon atoms, and oxoalkyl groups of 4 to 20 carbon atoms are as exemplified for $R^{L04}$.

Illustrative, non-limiting examples of the recurring units of formula (2A) are given below.

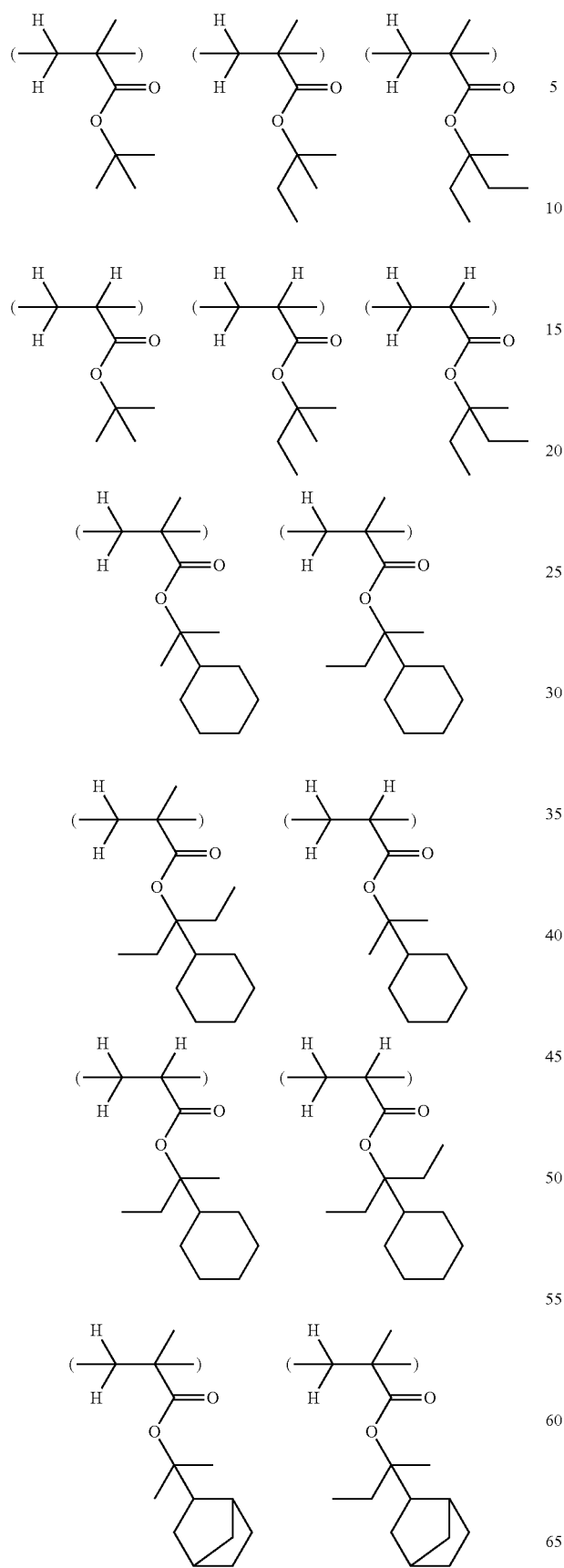
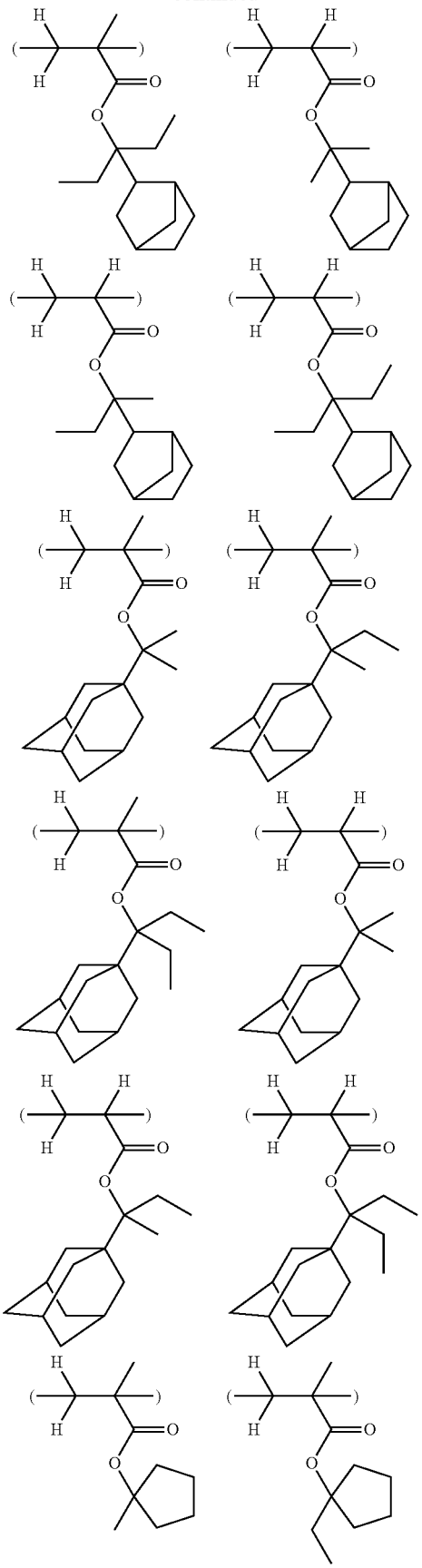

-continued
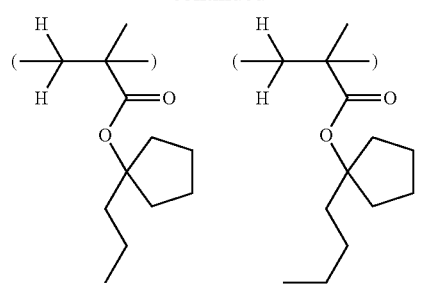
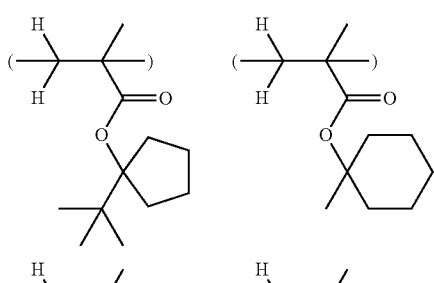
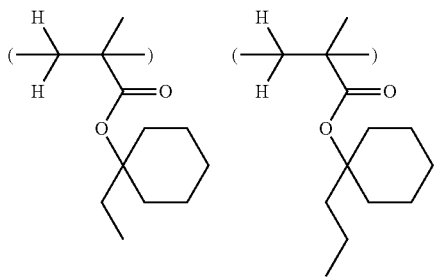
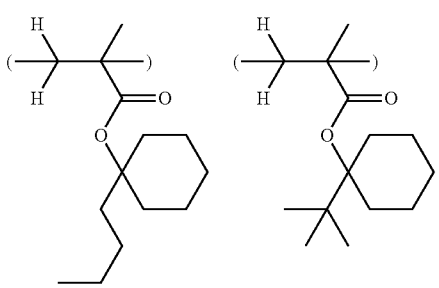
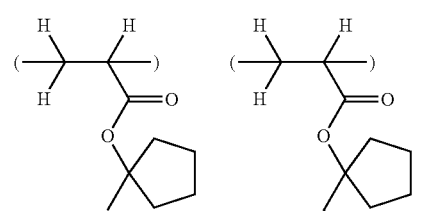
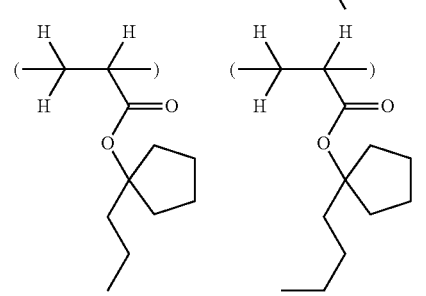
-continued
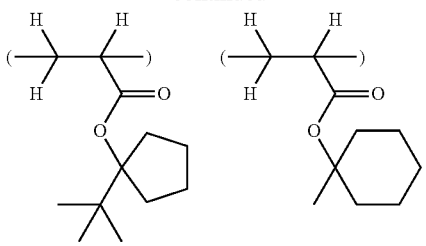
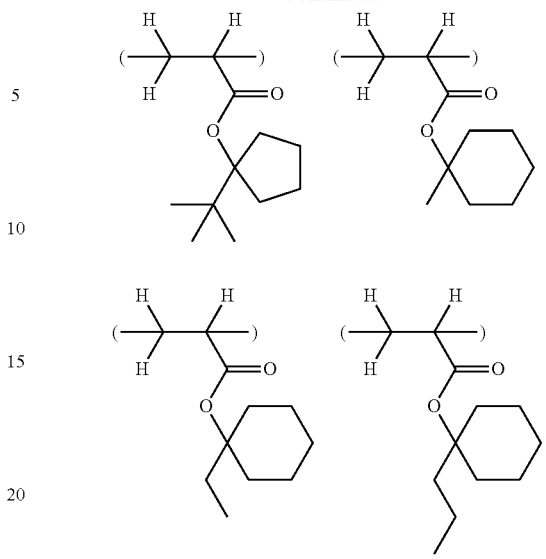
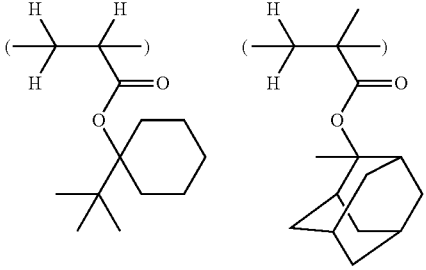
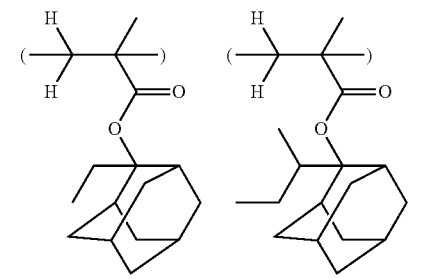
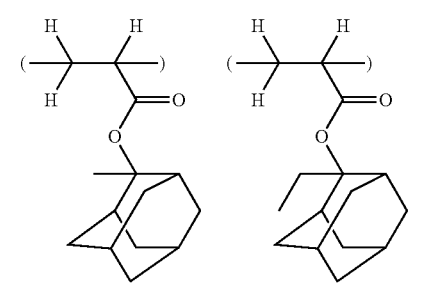
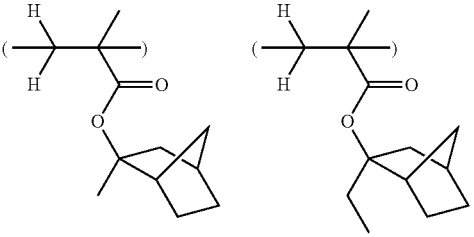

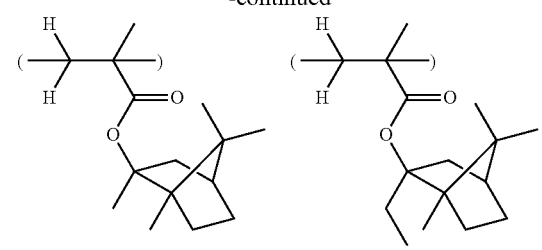
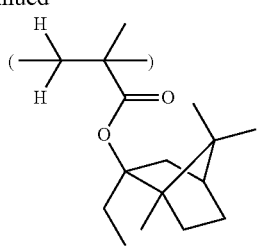
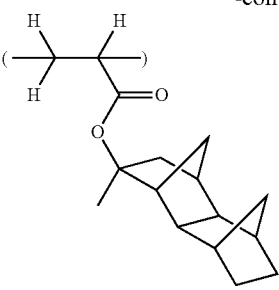
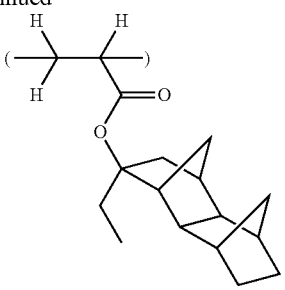
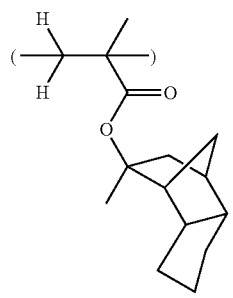
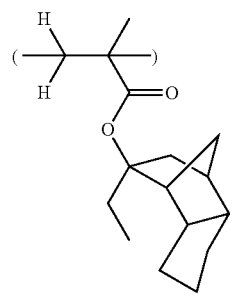
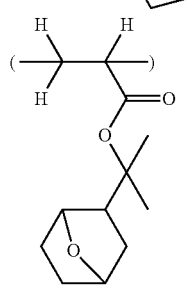
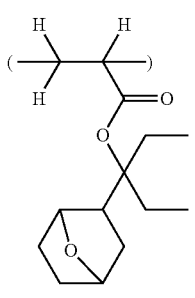
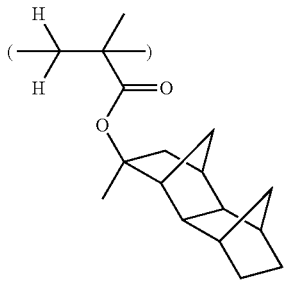
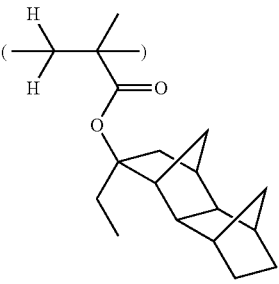
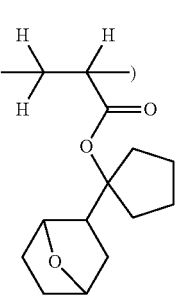
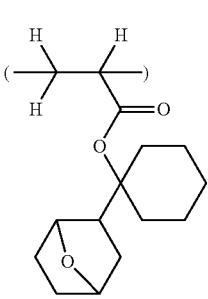
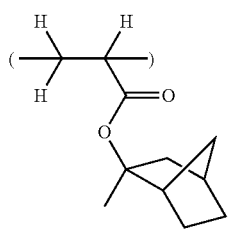
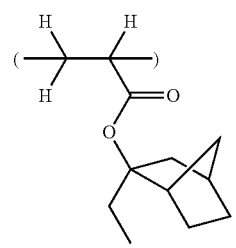
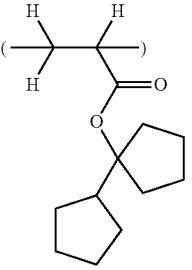
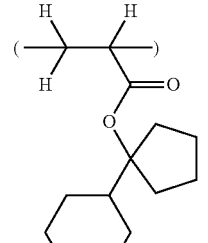
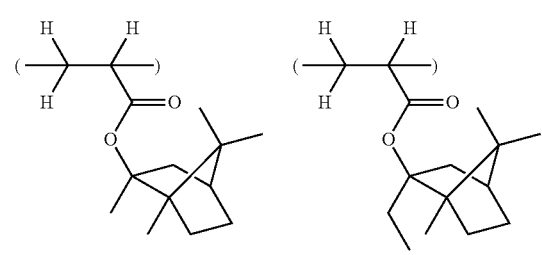
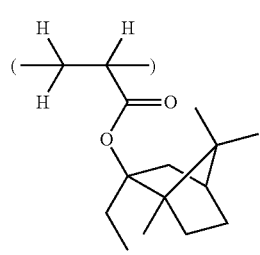
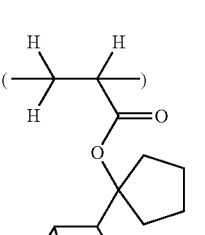
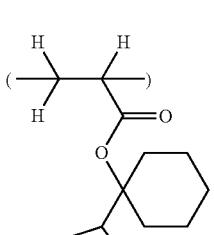
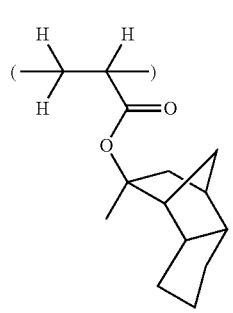
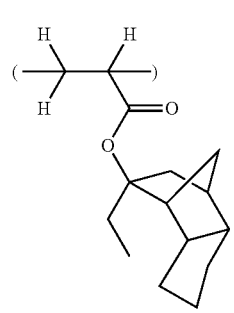
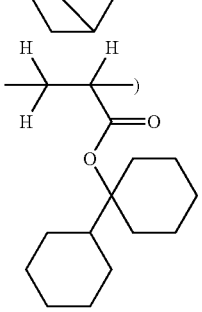
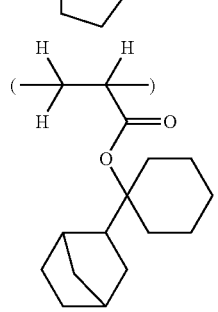

-continued
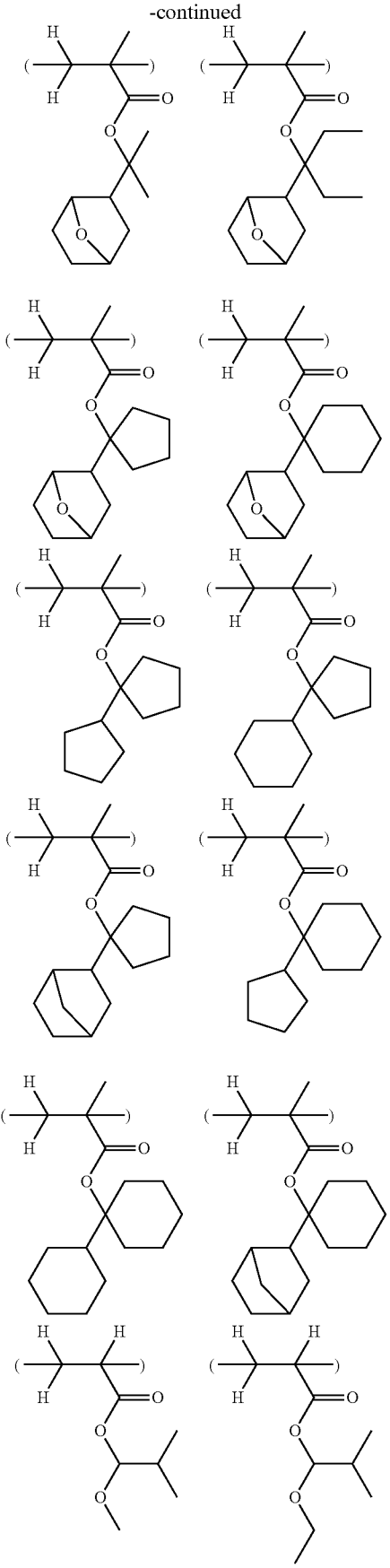
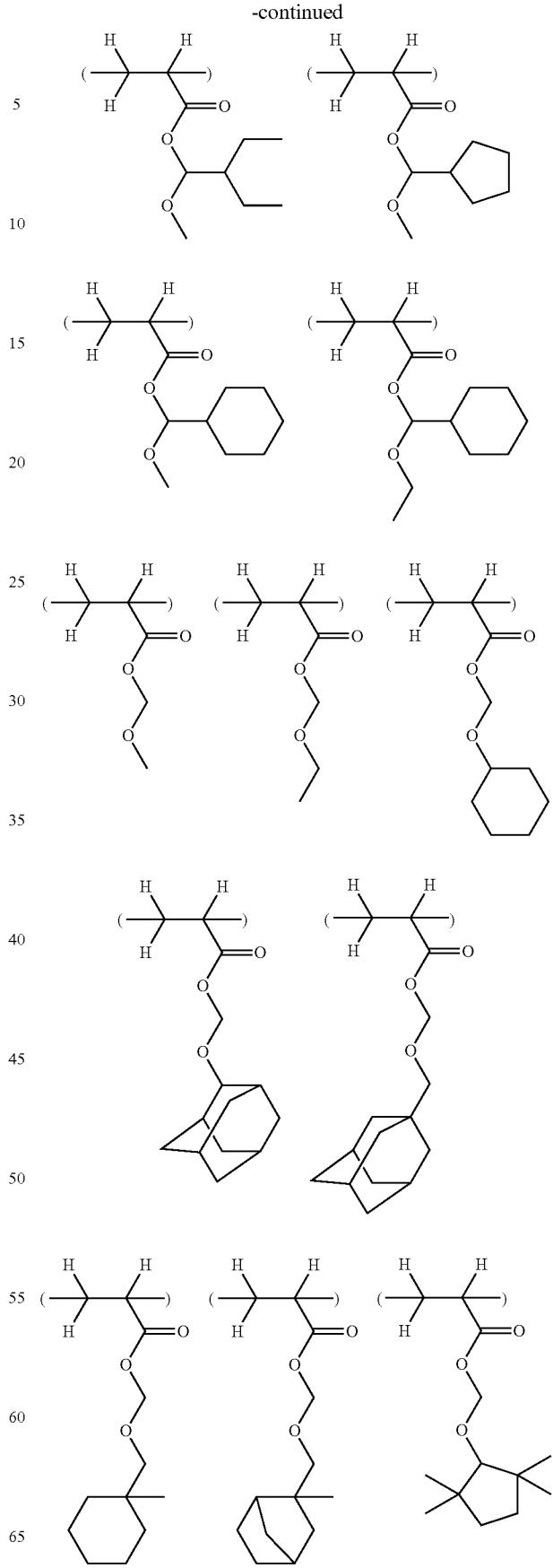

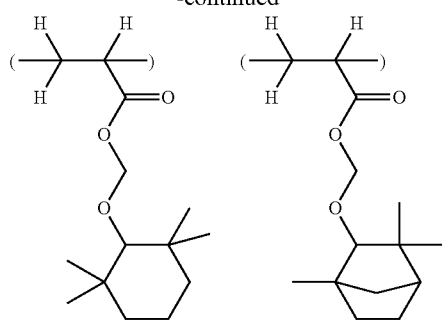
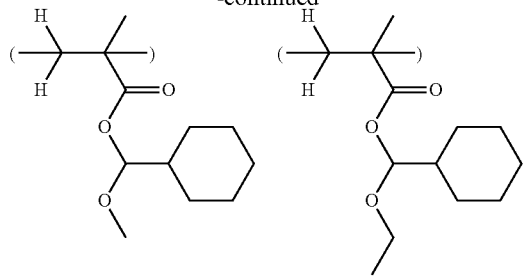
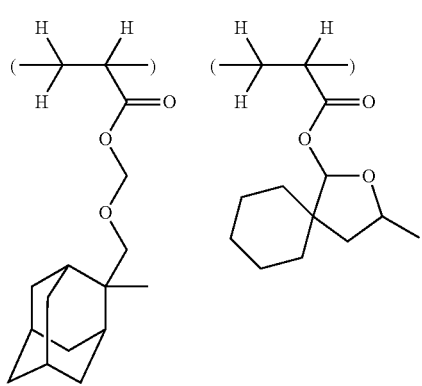
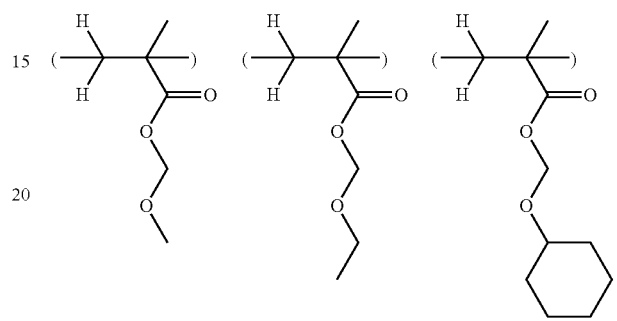
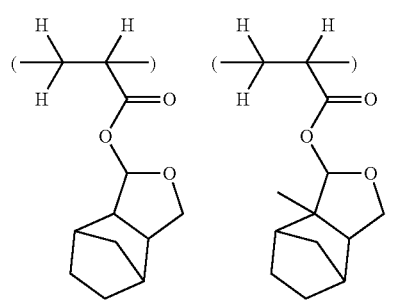
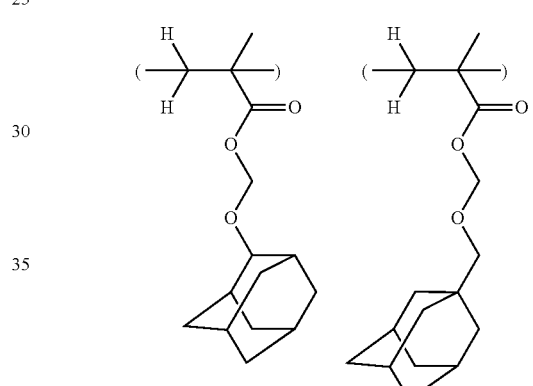
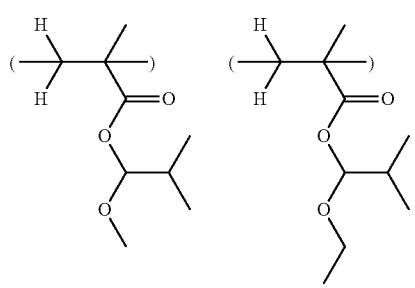
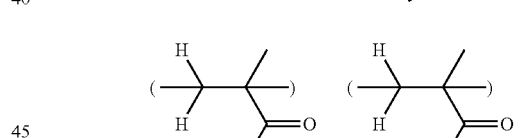
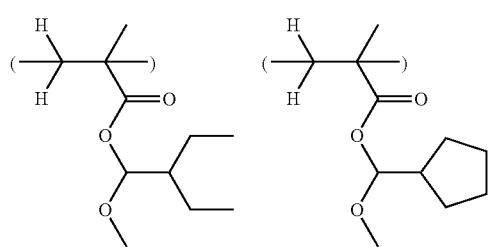
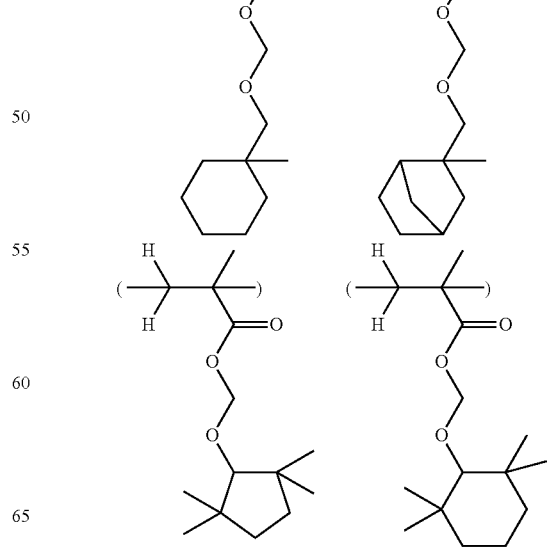

-continued
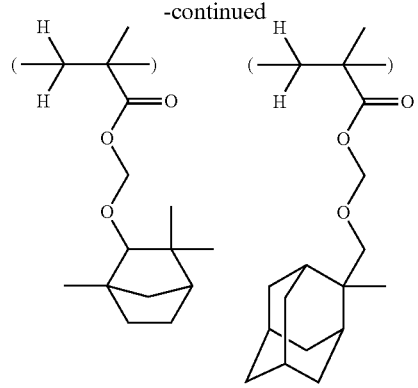
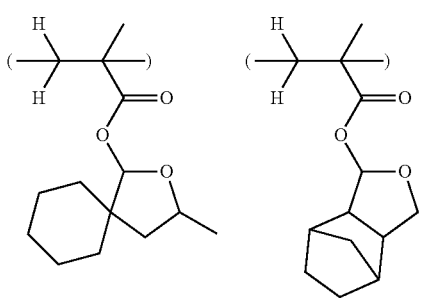
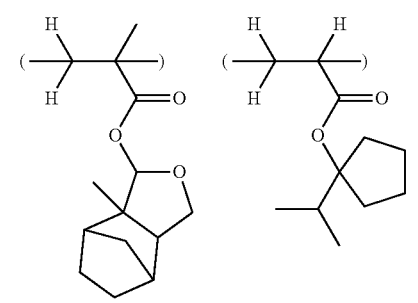
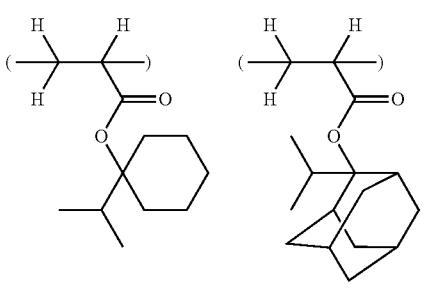
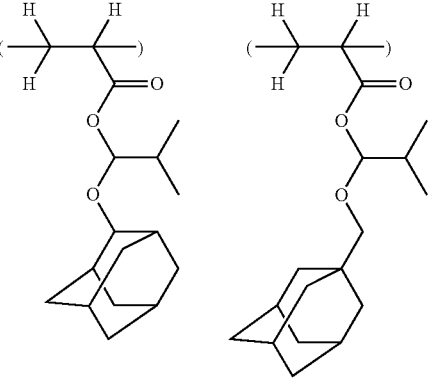
-continued
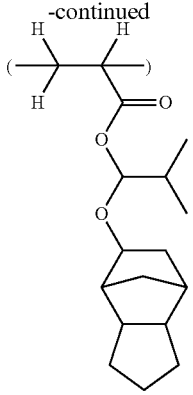
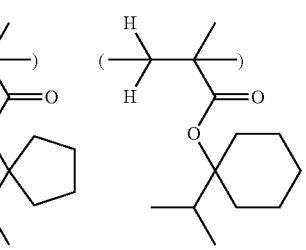
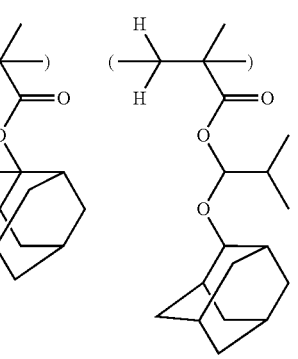
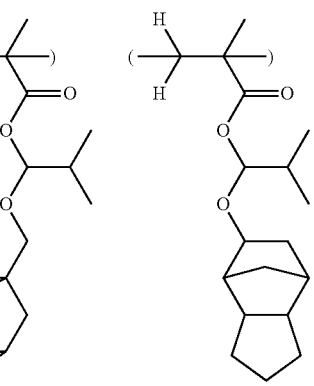
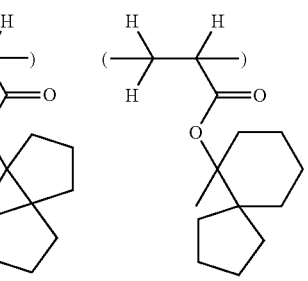

-continued
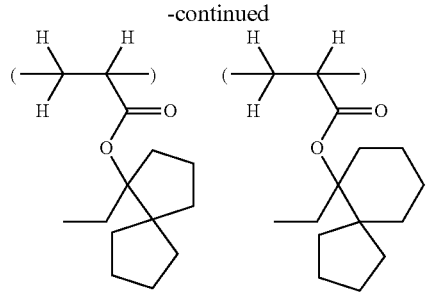 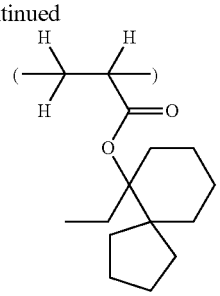
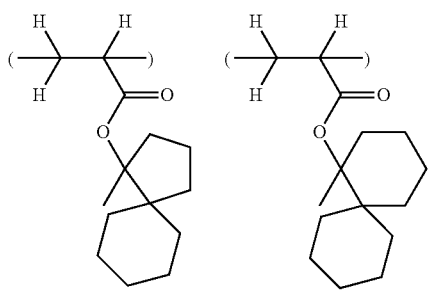 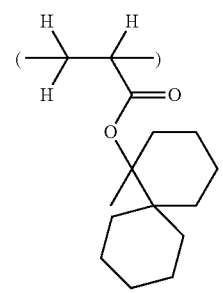
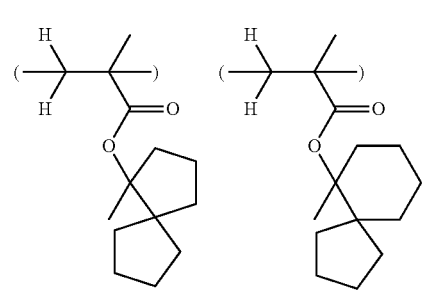 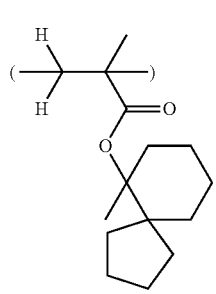
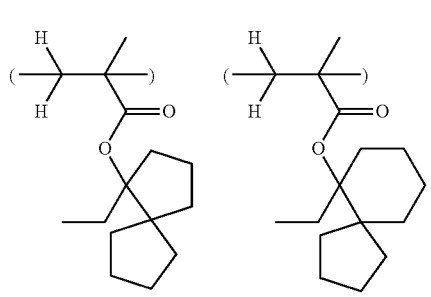 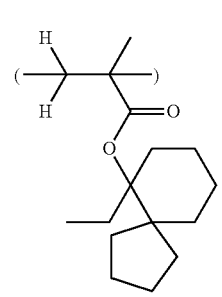
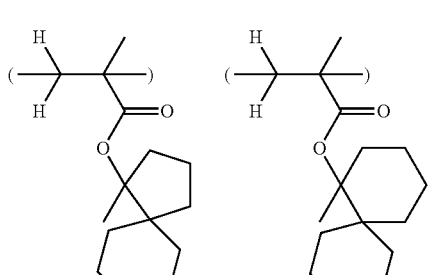 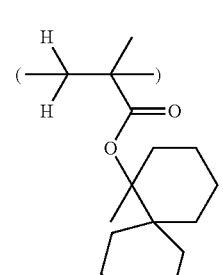
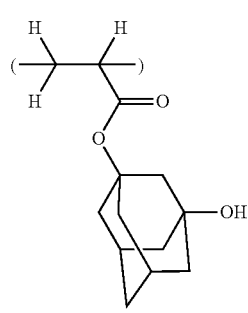 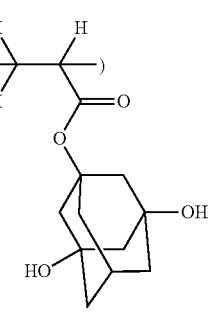
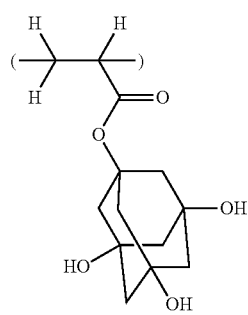 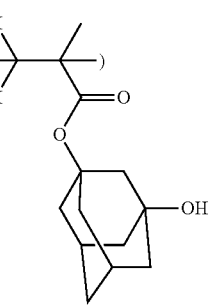
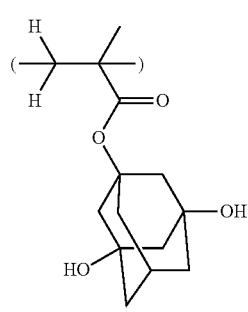 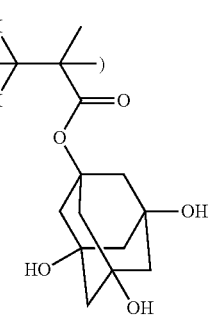
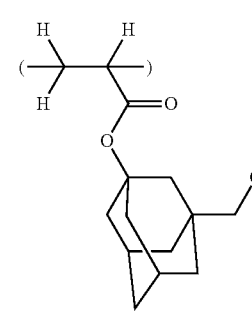 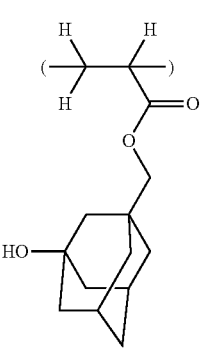
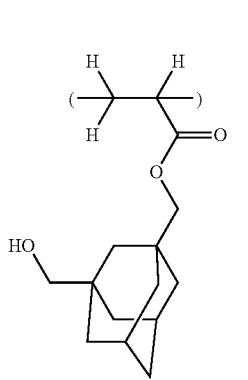 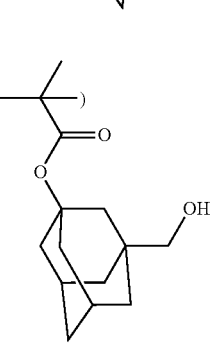
Illustrative, non-limiting examples of the recurring units of formula (2B) are given below.

-continued
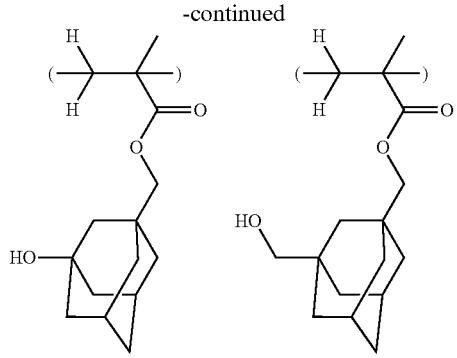
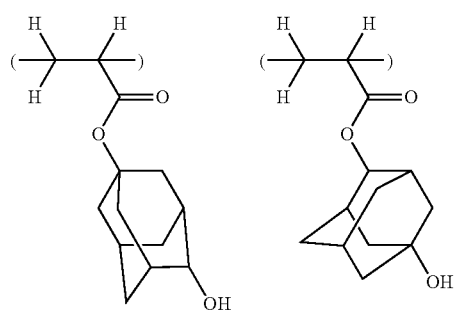
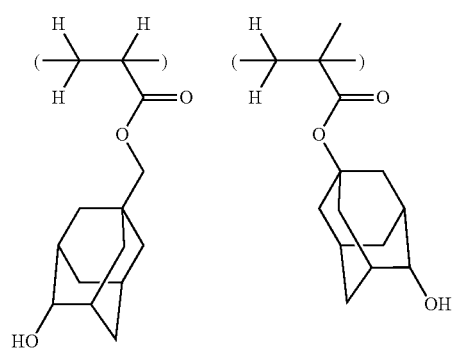
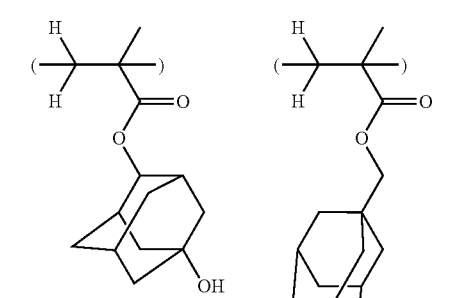
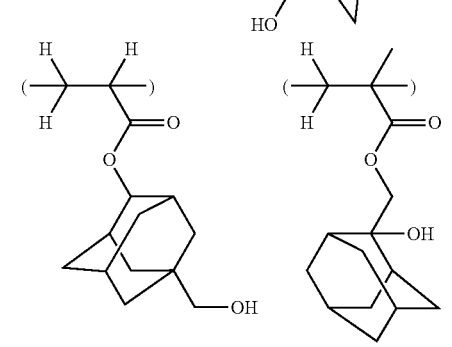
-continued
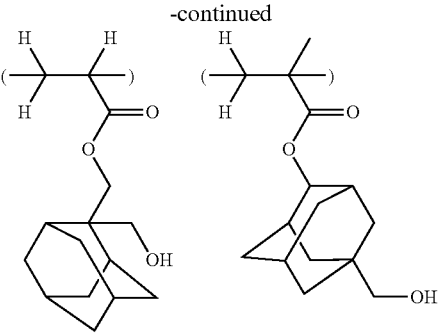
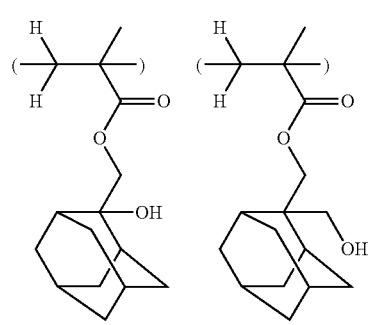
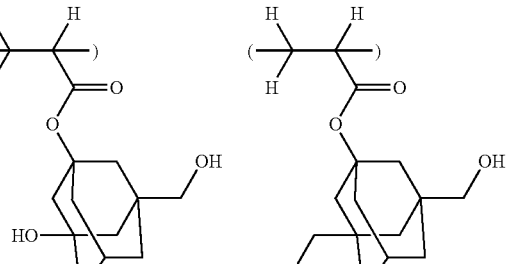
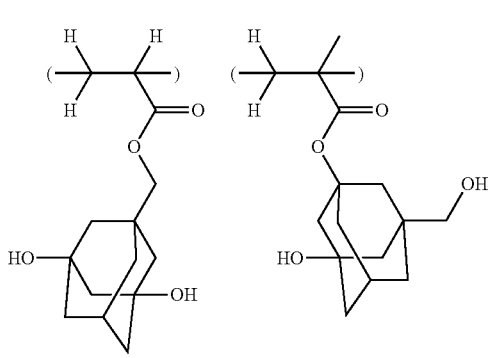
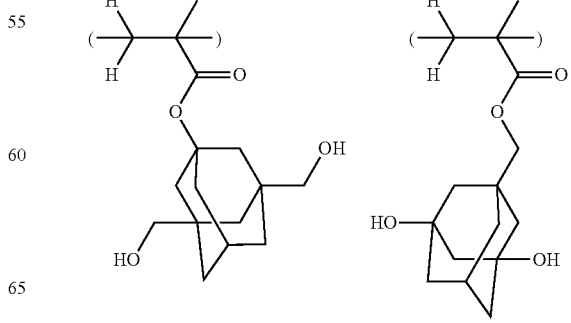

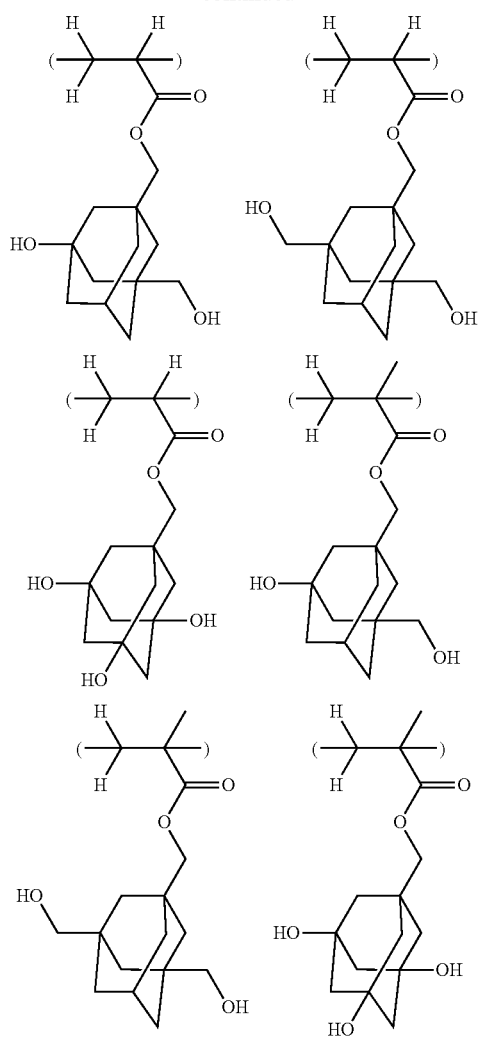
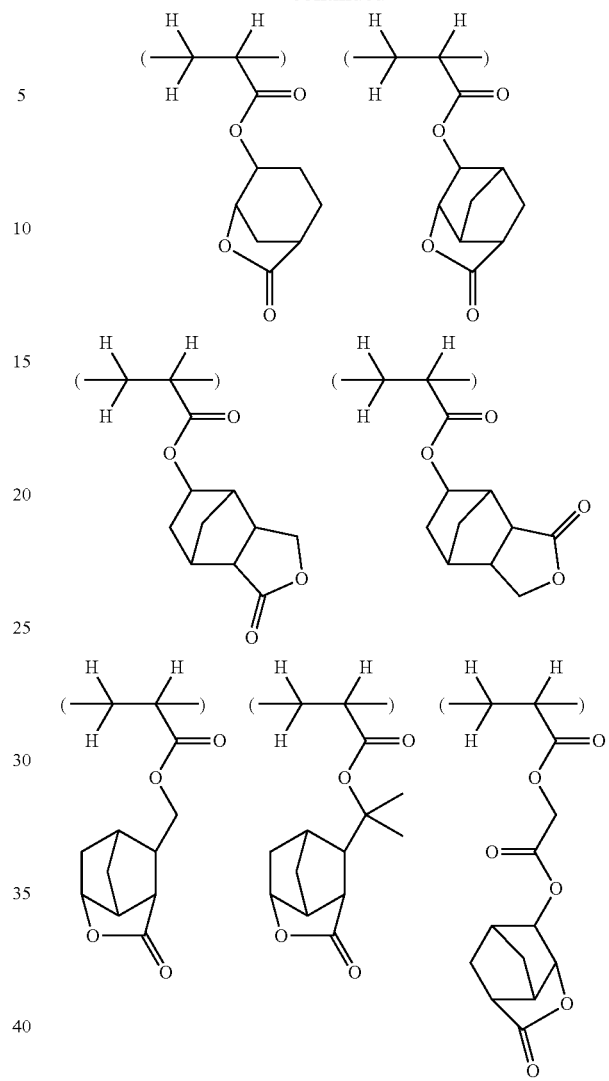
Illustrative, non-limiting examples of the recurring units of formula (2C) are given below.
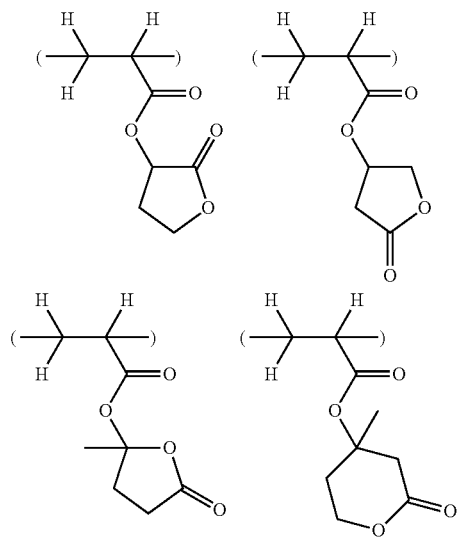
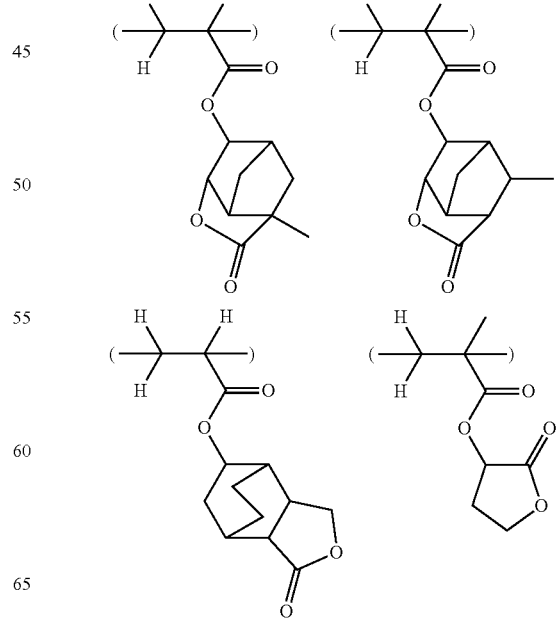

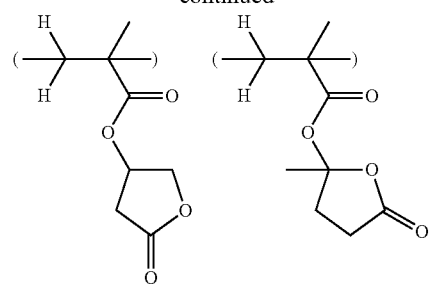
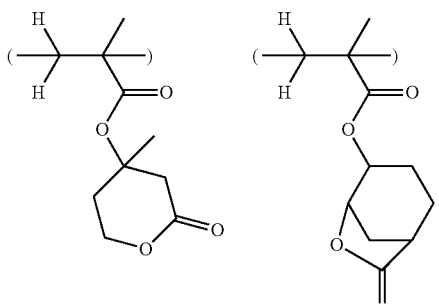
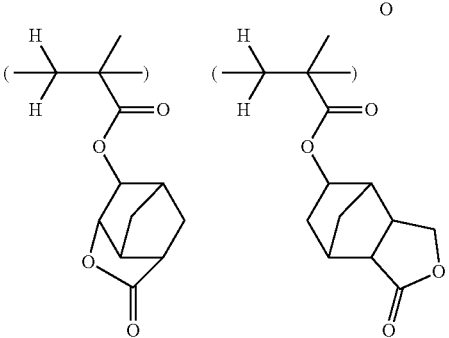
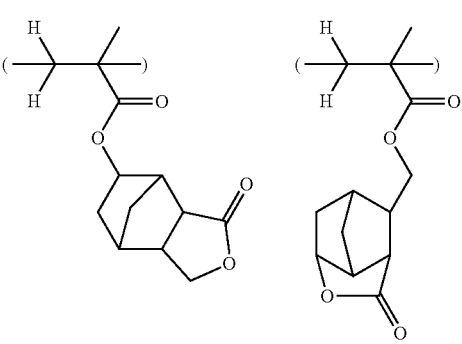
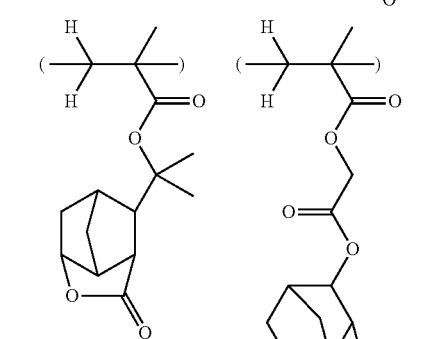

-continued
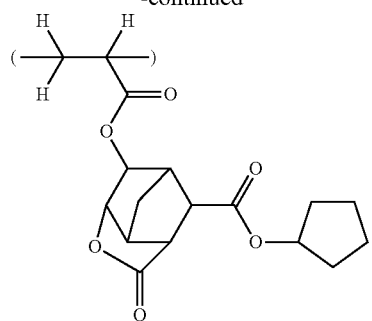
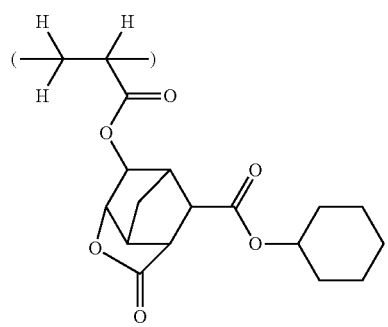
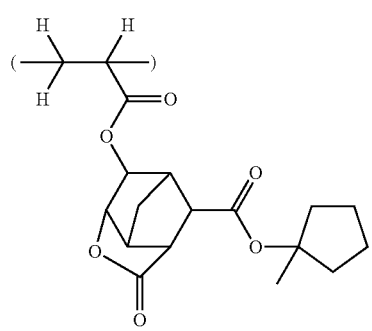
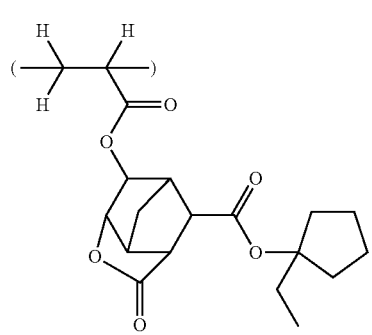
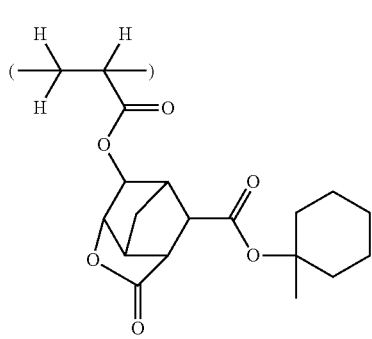
-continued
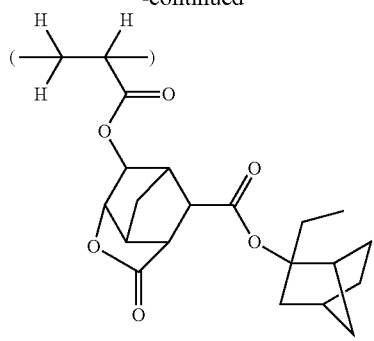
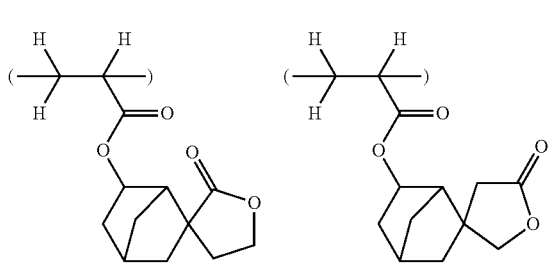
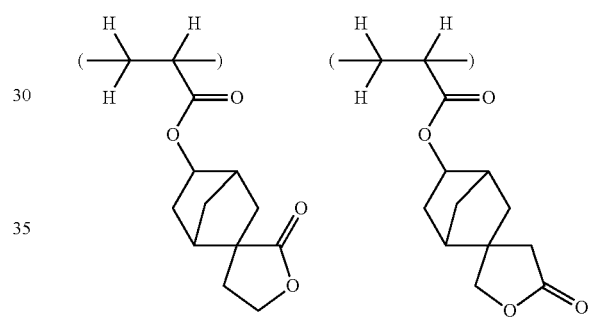
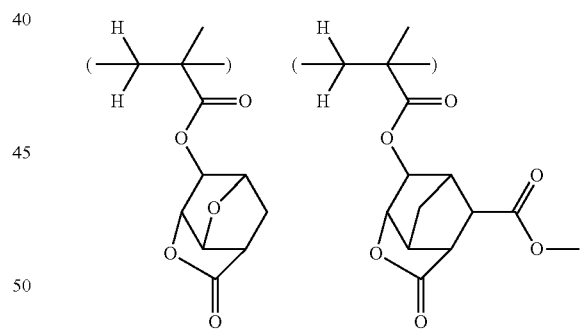
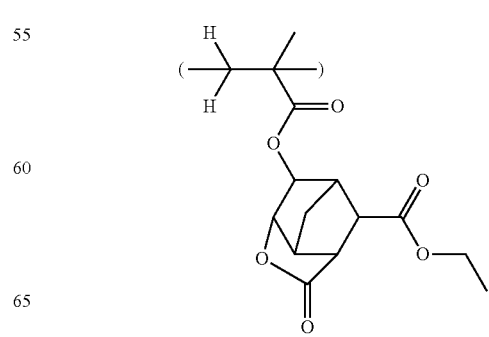

-continued
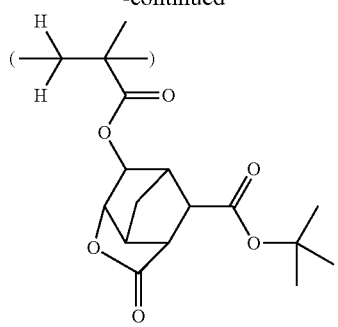
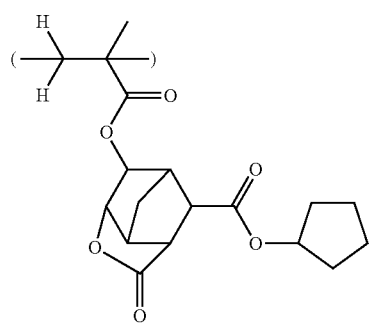
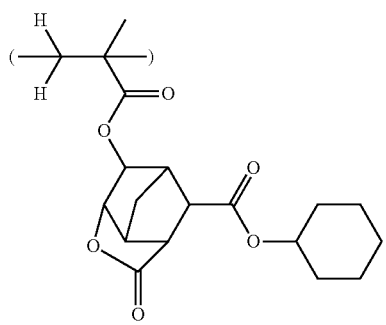
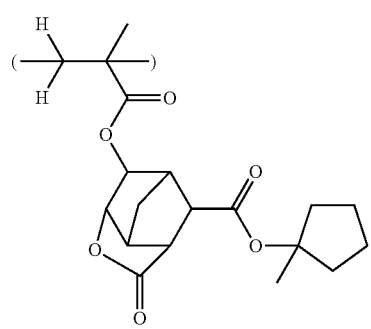
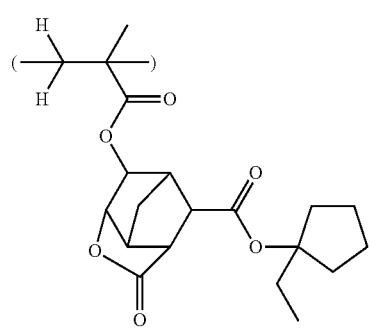
-continued
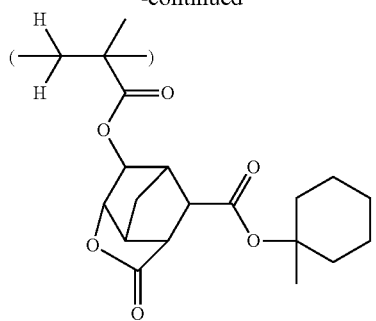
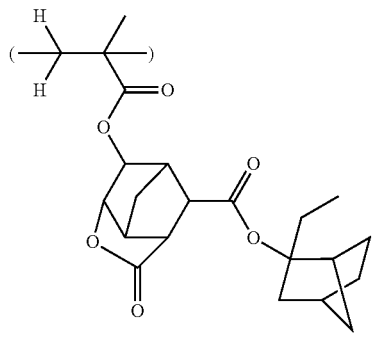
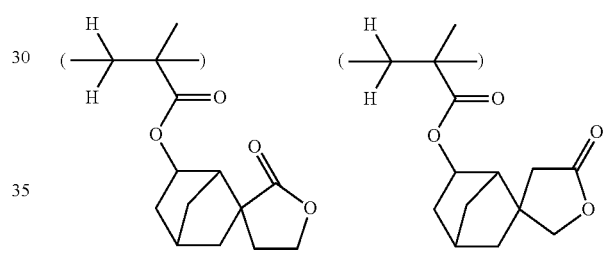
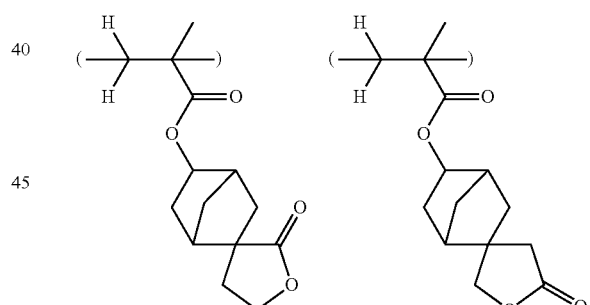
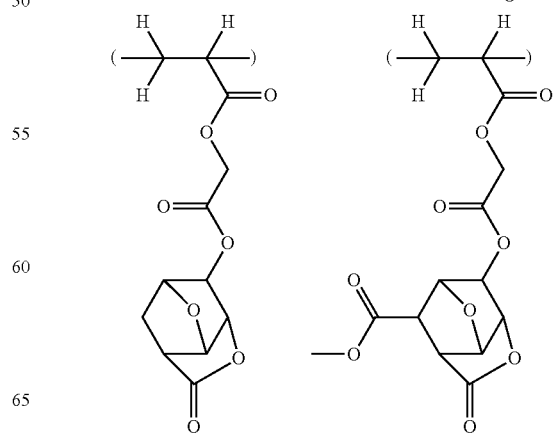

65
-continued
66
-continued
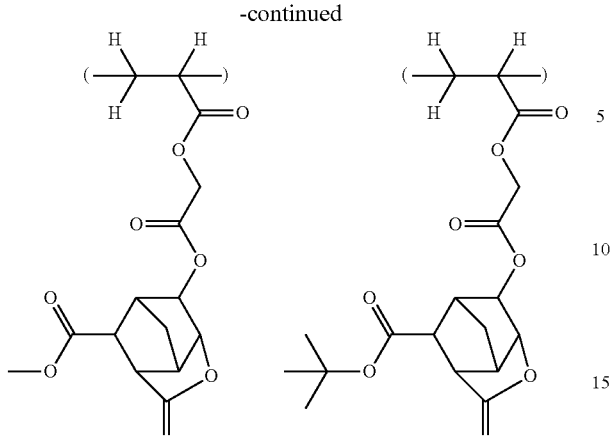
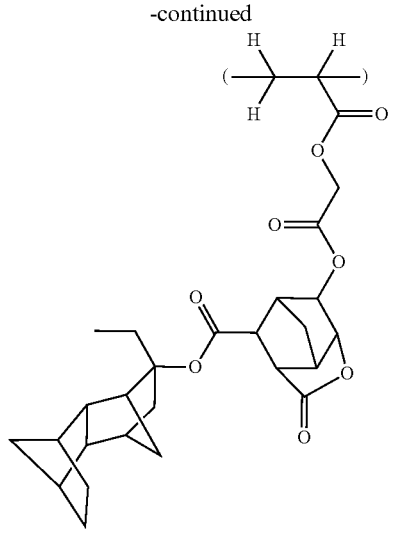
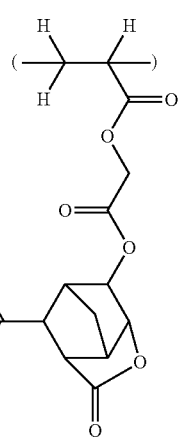
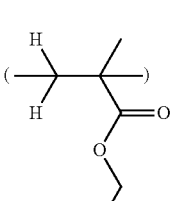 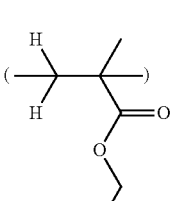
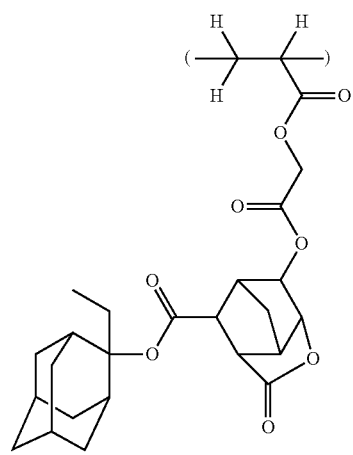
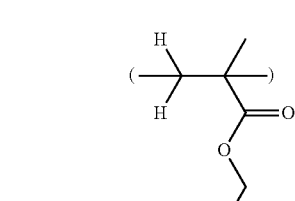 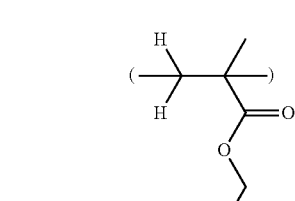

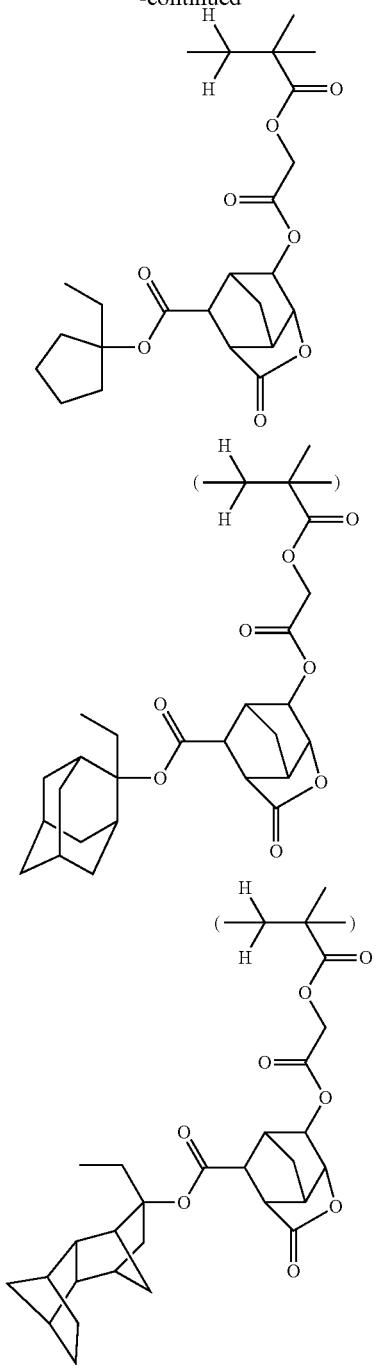
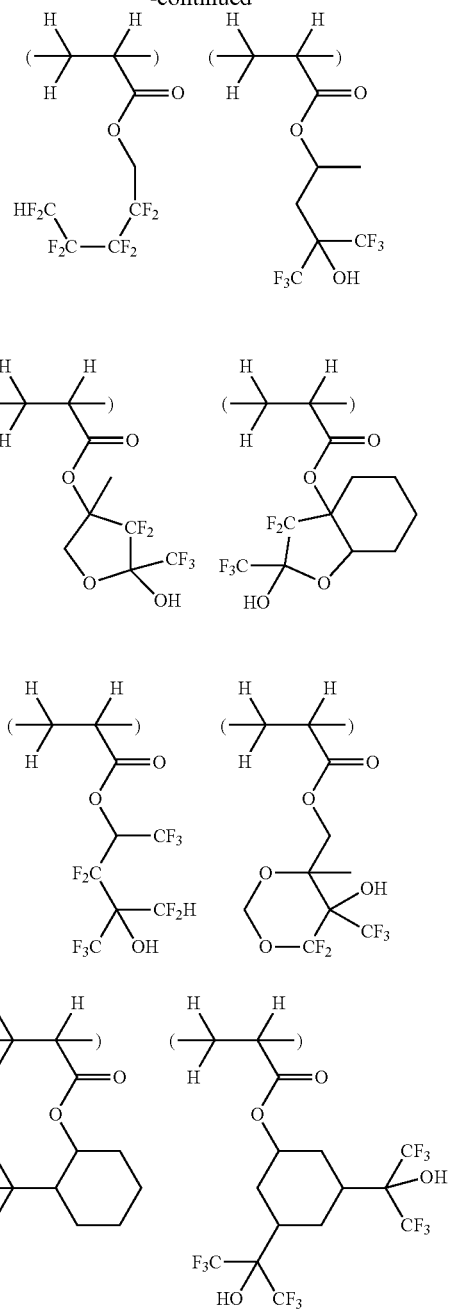
Illustrative, non-limiting examples of the recurring units of formula (2D) are given below.
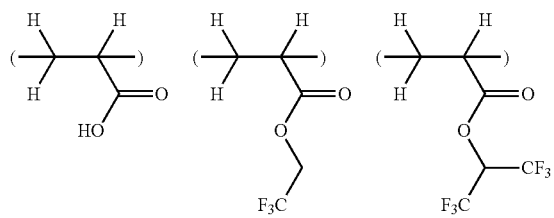
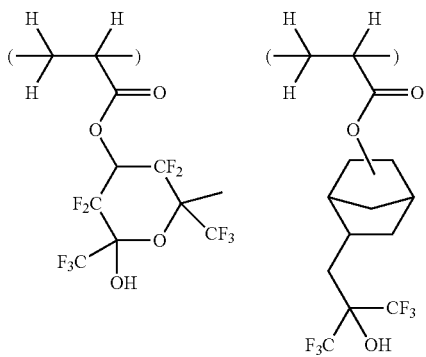

-continued
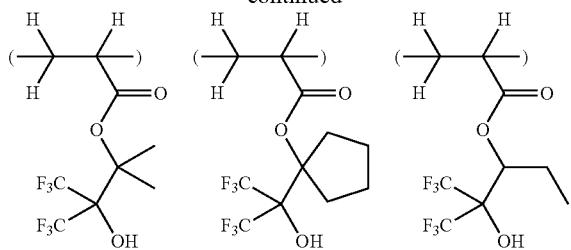
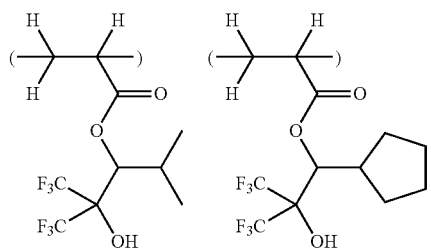
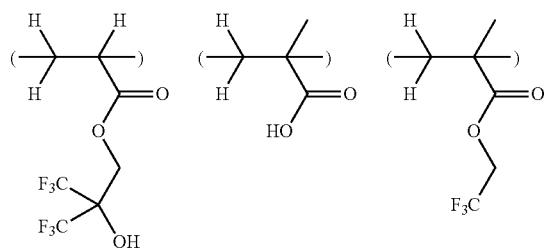
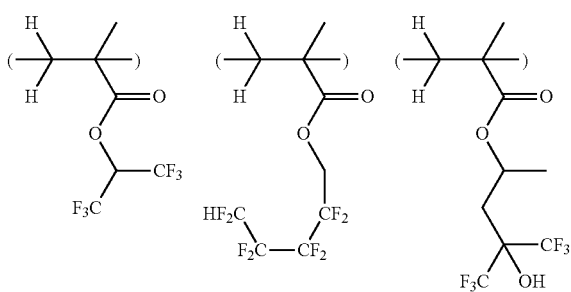
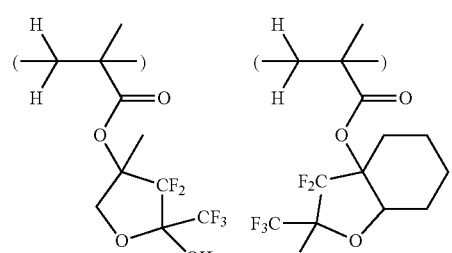
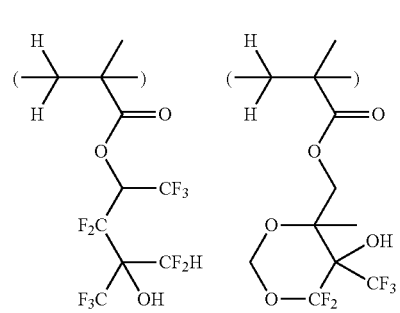
-continued
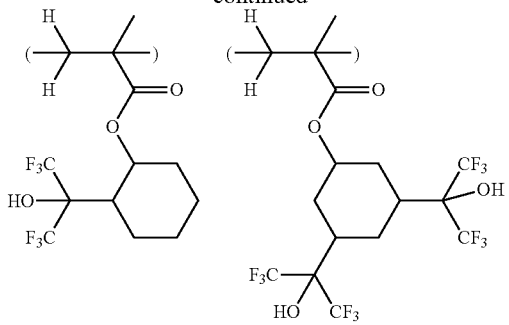
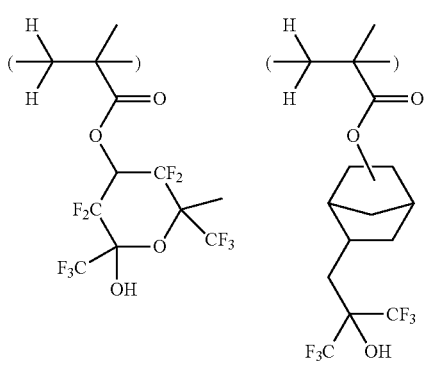
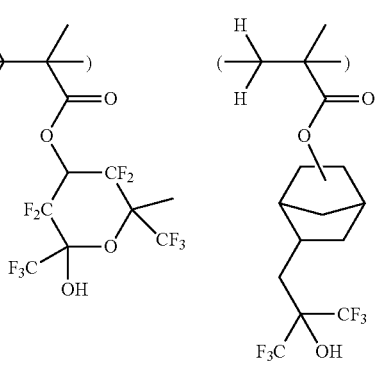
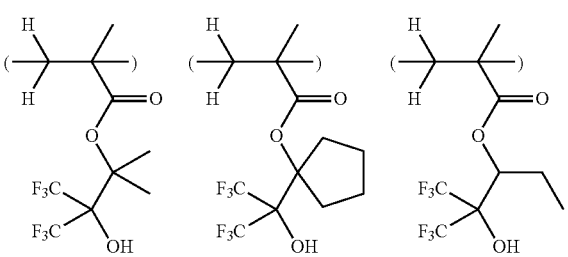
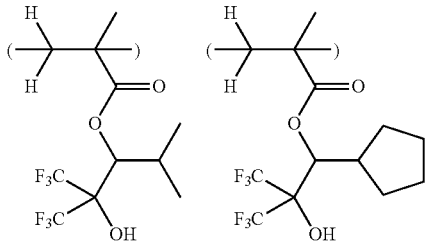
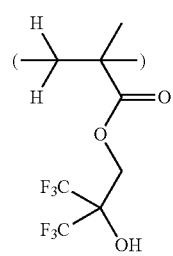
In the polymers of the invention, any of sulfonium salts having the general formulae (d1) to (d3) may be copolymerized.

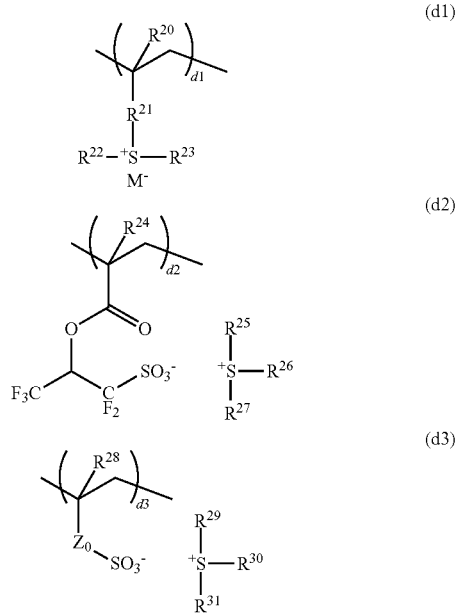

Herein $R^{20}$, $R^{24}$ and $R^{28}$ are hydrogen or methyl. $R^{21}$ is a single bond, phenylene, —O—$R^{33}$—, or —C(=O)—Y—$R^{33}$— wherein Y is oxygen or NH, and $R^{33}$ is a straight, branched or cyclic $C_1$-$C_6$ alkylene group, alkenylene group or phenylene group, which may contain a carbonyl (—CO—), ester (—COO—), ether (—O—), or hydroxyl radical. $R^{22}$, $R^{23}$, $R^{25}$, $R^{26}$, $R^{27}$, $R^{29}$$R^{30}$, and $R^{31}$ are each independently a straight, branched or cyclic $C_1$-$C_{12}$ alkyl group which may contain a carbonyl, ester or ether radical, or a $C_6$-$C_{12}$ aryl group, $C_7$-$C_{20}$ aralkyl group or thiophenyl group. $Z_0$ is a single bond, methylene, ethylene, phenylene, fluorinated phenylene, —O—$R^{32}$—, or —C(=O)—$Z_1$—$R^{32}$— wherein $Z_1$ is oxygen or NH, and $R^{32}$ is a straight, branched or cyclic $C_1$-$C_6$ alkylene group, alkenylene group or phenylene group, which may contain a carbonyl, ester, ether, or hydroxyl radical. $M^-$ is a non-nucleophilic counter ion.

In addition to the foregoing units, the polymers of the invention may further comprise recurring units derived from monomers having a carbon-carbon double bond, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[4.4.0.1$^{2,5}$.1$^{7,10}$] dodecene derivatives, unsaturated acid anhydrides such as itaconic anhydride, and other monomers.

The polymers of the invention generally have a weight average molecular weight (Mw) of 1,000 to 500,000, and preferably 3,000 to 100,000, as measured by GPC versus polystyrene standards using tetrahydrofuran solvent. Outside the range, there may result an extreme drop of etch resistance, and a drop of resolution due to difficulty to gain a dissolution rate difference before and after exposure.

In the inventive polymers, appropriate proportions of the respective recurring units derived from the monomers are given below although the invention is not limited thereto. The inventive polymers may contain:

(I) constituent units of one or more types having formula (2a) derived from monomer of formula (2) in a proportion of more than 0 mol % to 100 mol %, preferably 5 to 70 mol %, and more preferably 10 to 50 mol %, (II) constituent units of one or more types having formulas (2A) to (2D) in a proportion of 0 mol % to less than 100 mol %, preferably 30 to 95 mol %, and more preferably 50 to 90 mol %, and (III) constituent units of one or more types having formulas (d1) to (d3) in a proportion of 0 to 30 mol %, preferably 0 to 20 mol %, and more preferably 0 to 10 mol %, and (IV) constituent units of one or more types derived from other monomers in a proportion of 0 to 80 mol %, preferably 0 to 70 mol %, and more preferably 0 to 50 mol %, based on the total moles of constituent units.

The polymers of the invention are prepared by copolymerization reaction using the compound of formula (2) as a first monomer and polymerizable double bond-bearing compounds as second and subsequent monomers.

The copolymerization reaction to produce the inventive polymers may be performed in various modes, preferably radical polymerization, anionic polymerization or coordination polymerization.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about 0.5 to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about 0.5 to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about 0.5 to about 48 hours. Reaction conditions outside the described range may be employed if desired.

Resist Composition

Since the polymer of the invention is useful as the base resin of a resist composition, the other aspect of the invention provides a resist composition comprising the polymer and specifically a chemically amplified positive resist composition comprising the polymer. Typically, the resist composition contains (A) the inventive polymer as a base resin, (B) an acid generator, (C) an organic solvent, and optionally (D) an organic nitrogen-containing compound and (E) a surfactant. It is understood that the acid generator (B) may be omitted when the polymer contains recurring units of any one of formulae (d1) to (d3).

In addition to the inventive polymer, the base resin (A) may include another polymer having a dissolution rate in alkaline developer that increases under the action of acid, if necessary.

Examples of the other polymer include, but are not limited to, (i) poly(meth)acrylic acid derivatives, (ii) norbornene derivative-maleic anhydride copolymers, (iii) hydrogenated products of ring-opening metathesis polymerization (ROMP) polymers, and (iv) vinyl ether-maleic anhydride-(meth) acrylic acid derivative copolymers.

Of these, the hydrogenated products of ROMP polymers are synthesized by the method illustrated in JP-A 2003-66612. Illustrative examples of such hydrogenated polymers include those polymers having the recurring units shown below, but are not limited thereto.

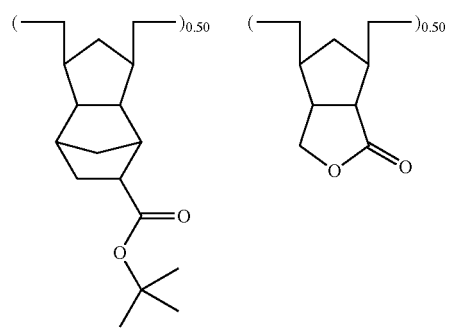

75
-continued
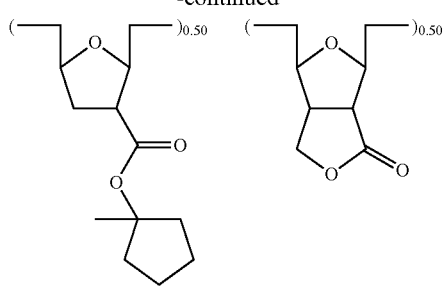
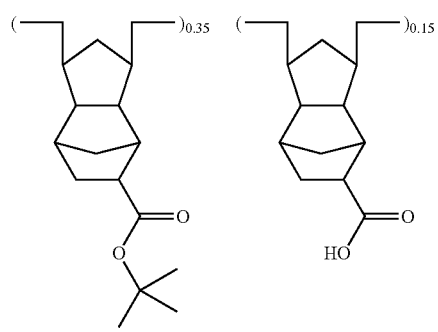
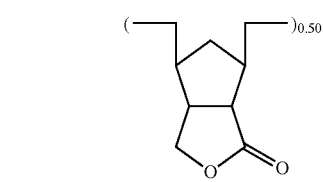
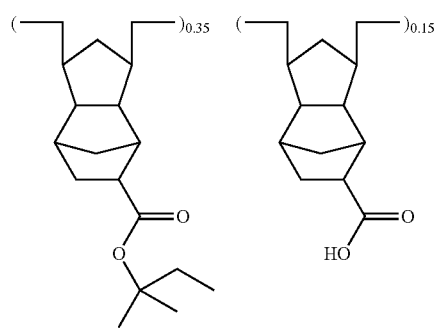
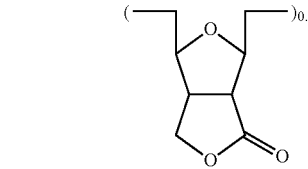
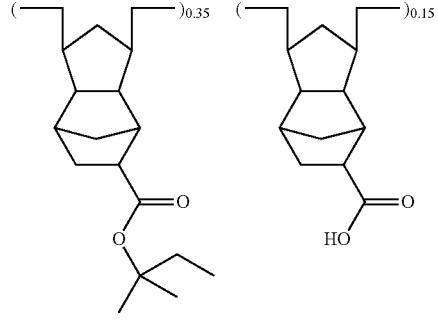
76
-continued
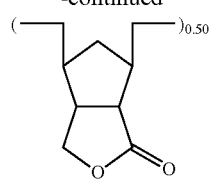
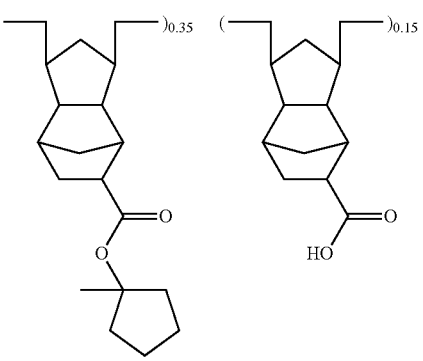
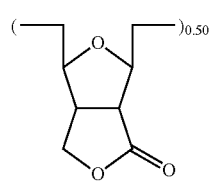
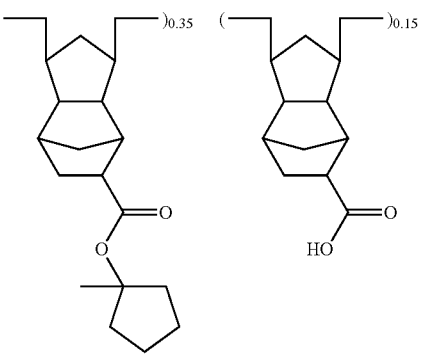
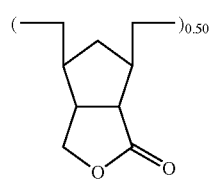
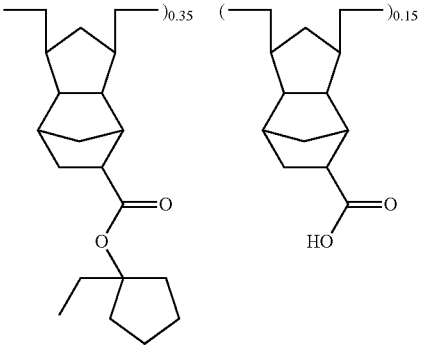

-continued

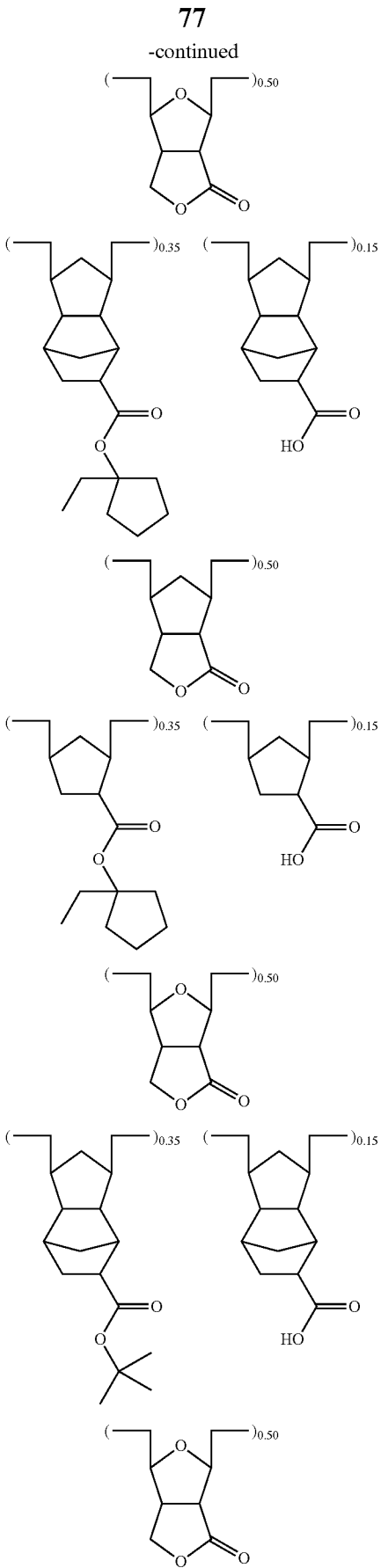

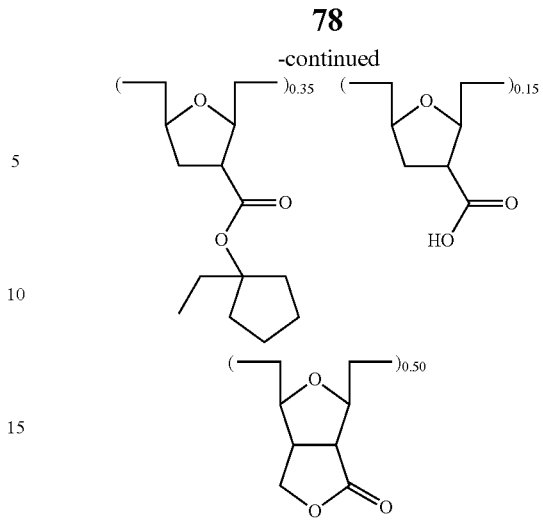

The inventive polymer and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer.

The other polymer is not limited to one type and a mixture of two or more other polymers may be added. The use of plural polymers allows for easy adjustment of resist properties.

Acid Generator

The acid generator (B) used herein may be a photoacid generator (PAG). The PAG may be any compound capable of generating an acid upon exposure of high-energy radiation. Suitable PAGs include sulfonium salt, iodonium salt, sulfonyldiazomethane, N-sulfonyloxyimide, and oxime-O-sulfonate acid generators. Exemplary acid generators are described in JP-A 2009-269953, paragraphs [0151] to [0156] (US 20090274978).

The preferred PAGs are those compounds of the general formula (B)-1.

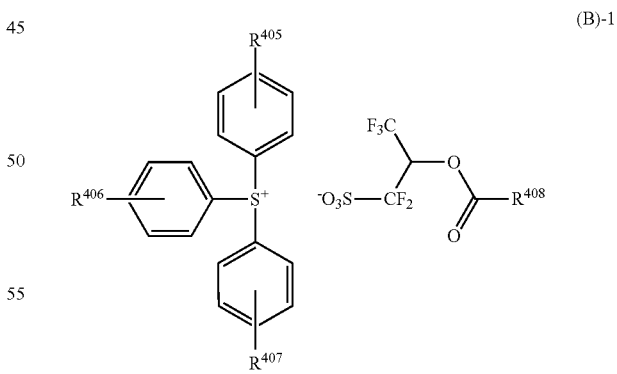

(B)-1

Herein $R^{405}$, $R^{406}$, and $R^{407}$ are each independently hydrogen or a straight, branched or cyclic $C_1$-$C_{20}$ monovalent hydrocarbon group which may contain a heteroatom, typically an alkyl or alkoxy group. $R^{408}$ is a straight, branched or cyclic $C_7$-$C_{30}$ monovalent hydrocarbon group which may contain a heteroatom.

Examples of the hydrocarbon groups optionally containing a heteroatom, represented by $R^{405}$, $R^{406}$, and $R^{407}$, include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, butyladamantyl, and modified forms of the foregoing in which any carbon-carbon bond is separated by a hetero-atomic grouping such as —O—, —S—, —SO—, —SO$_2$—, —NH—, —C(=O)—, —C(=O)O—, or —C(=O)NH—, or any hydrogen atom is replaced by a functional group such as —OH, —NH$_2$, —CHO, or —CO$_2$H. Examples of the straight, branched or cyclic C$_7$-C$_{30}$ monovalent hydrocarbon groups optionally containing a heteroatom, represented by R$^{408}$, are shown below, but not limited thereto.

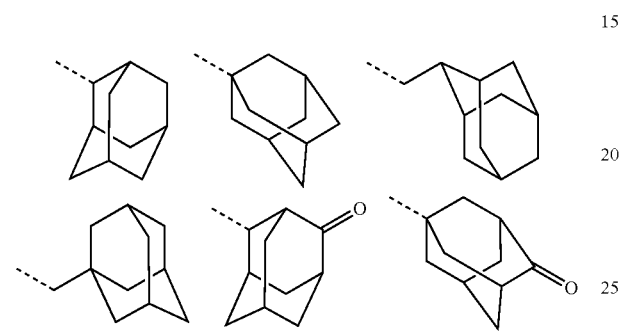

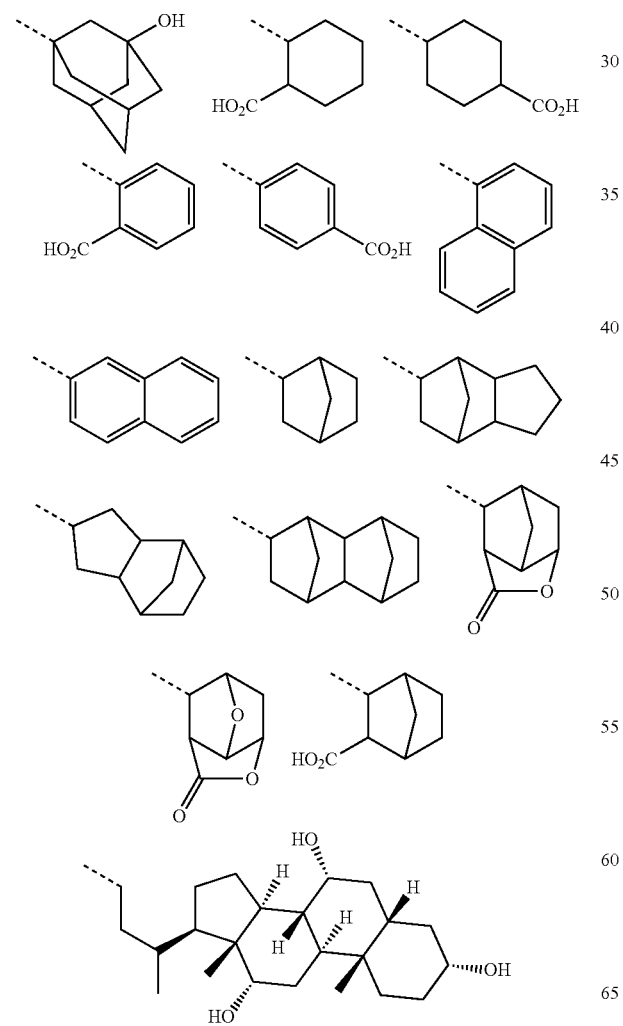

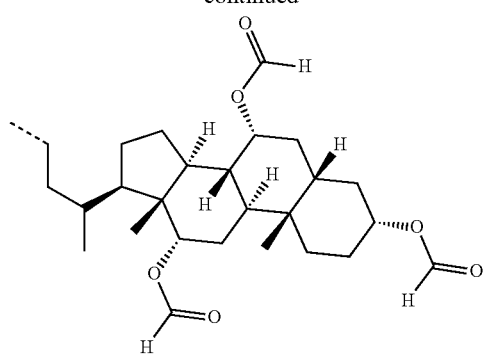

Illustrative examples of acid generators (B)-1 are shown below, but not limited thereto.

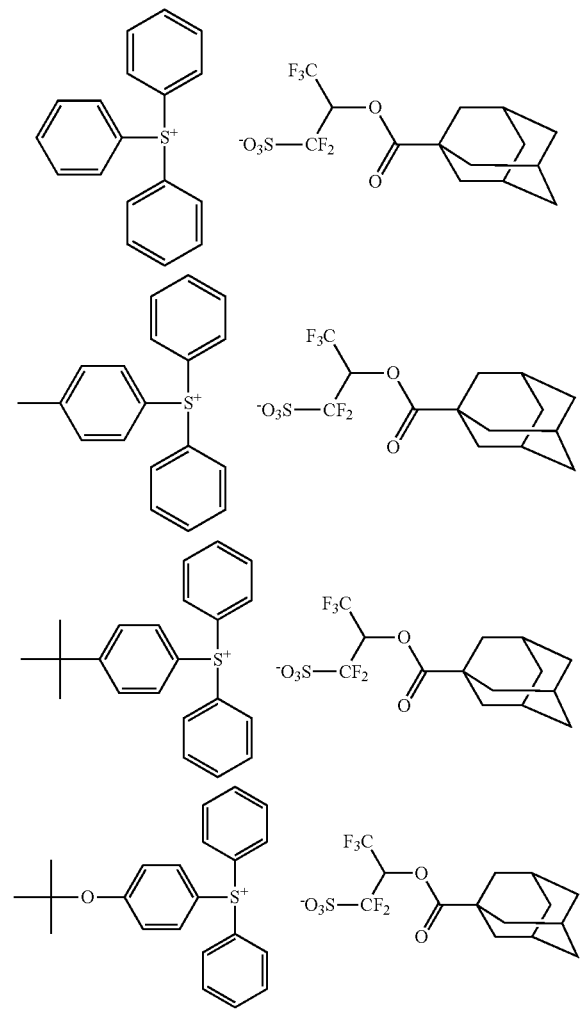

81
-continued
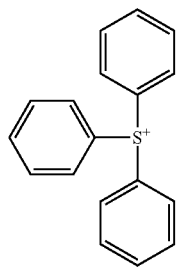 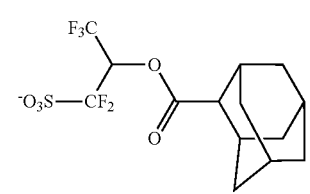
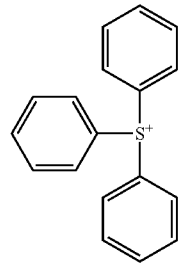 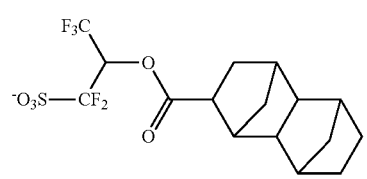
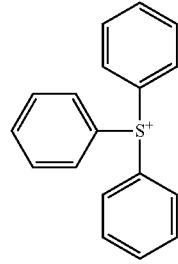 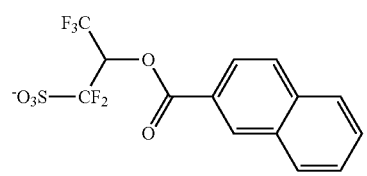
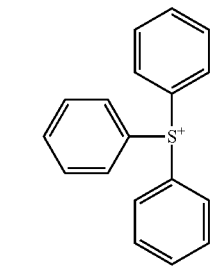 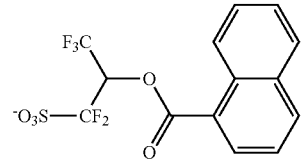
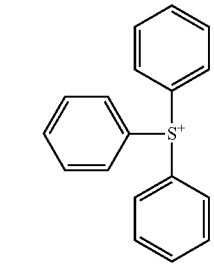 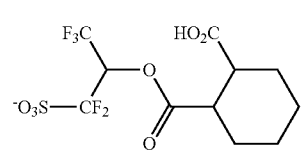
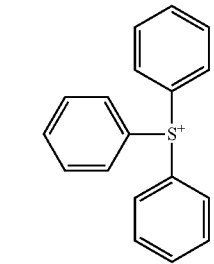 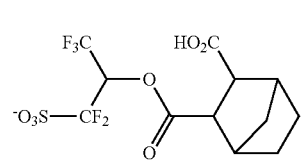
82
-continued
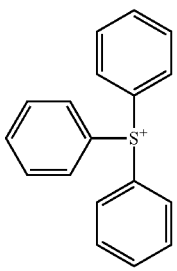 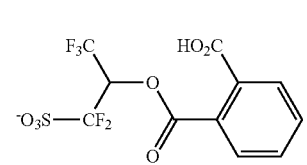
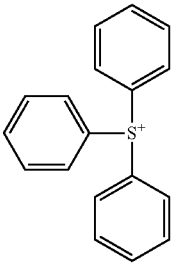 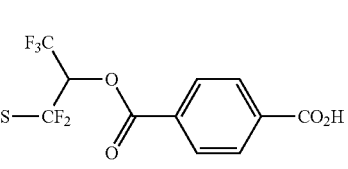
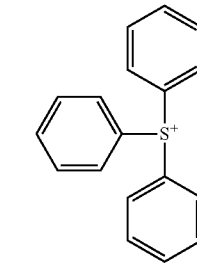 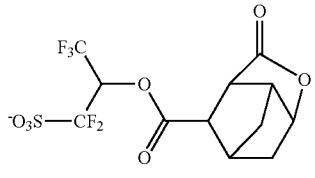
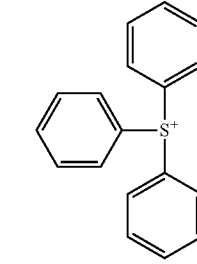 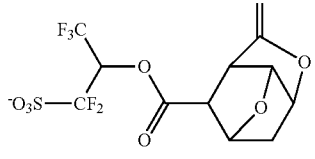
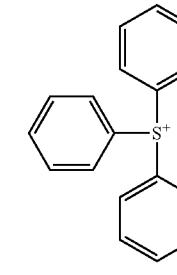 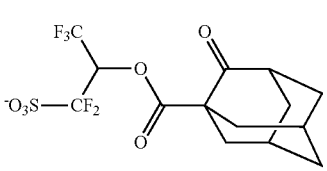
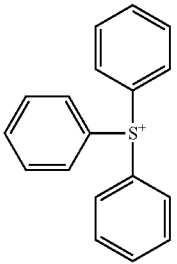 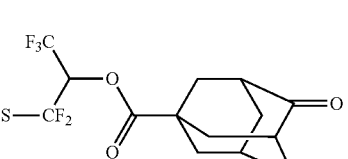

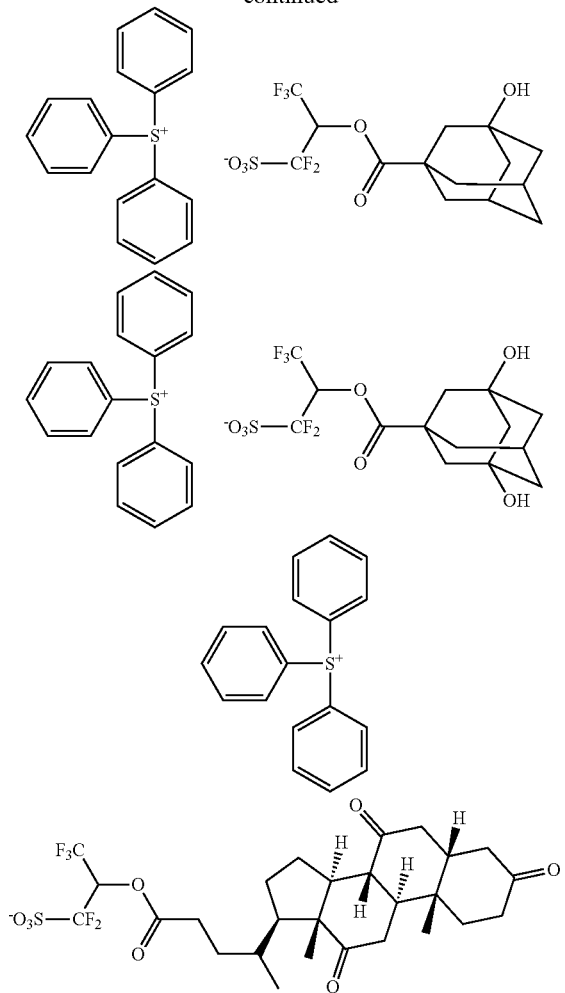

It is noted that an acid diffusion controlling function may be provided when two or more PAGs are used in admixture provided that one PAG is an onium salt capable of generating a weak acid. Specifically, in a system using a mixture of a PAG capable of generating a strong acid (e.g., fluorinated sulfonic acid) and an onium salt capable of generating a weak acid (e.g., non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If the PAG capable of generating a strong acid is also an onium salt, an exchange from the strong acid (generated upon exposure to high-energy radiation) to a weak acid as above can take place, but it never happens that the weak acid (generated upon exposure to high-energy radiation) collides with the unreacted onium salt capable of generating a strong acid to induce a salt exchange. This is because of a likelihood of an onium cation forming an ion pair with a stronger acid anion.

An appropriate amount of PAG added is 0.1 to 40 parts, and more preferably 0.1 to 20 parts by weight per 100 parts by weight of the base resin (A) in the composition. As long as PAG is up to 40 phr, the resulting photoresist film has a fully high transmittance and a minimal likelihood of degraded resolution. The PAG may be used alone or in admixture of two or more. The transmittance of the resist film can be controlled by using a PAG having a low transmittance at the exposure wavelength and adjusting the amount of the PAG added.

In the resist composition, there may be added a compound which is decomposed with an acid to generate an acid, that is, acid-amplifier compound. For these compounds, reference should be made to J. Photopolym. Sci. and Tech., 8, 43-44, 45-46 (1995), and ibid., 9, 29-30 (1996). Examples of the acid-amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior. In the resist composition, an appropriate amount of the acid-amplifier compound is up to 2 parts, and especially up to 1 part by weight per 100 parts by weight of the base resin. Excessive amounts of the acid-amplifier compound make diffusion control difficult, leading to degradation of resolution and pattern profile.

Organic Solvent

The organic solvent (C) used herein may be any organic solvent in which the base resin, acid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, PGMEA, and mixtures thereof because the acid generator is most soluble therein.

An appropriate amount of the organic solvent used is about 200 to 1,000 parts, especially about 400 to 800 parts by weight per 100 parts by weight of the base resin.

Nitrogen-Containing Compound

In the resist composition, an organic nitrogen-containing compound or compounds (D) may be compounded. The organic nitrogen-containing compound used herein is preferably a compound capable of suppressing the rate of diffusion when the acid generated by the acid generator diffuses within the resist film. The inclusion of such a quencher facilitates to adjust the resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile.

Suitable organic nitrogen-containing compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, imide derivatives, and carbamate derivatives. Examples of these nitrogen-containing compounds are described in JP-A 2009-269953, paragraphs [0122] to [0141] (US 20090274978).

The organic nitrogen-containing compound is preferably formulated in an amount of 0.001 to 8 parts, and especially 0.01 to 4 parts by weight, per 100 parts by weight of the base resin. Less than 0.001 phr of the nitrogen-containing compound achieves no or little addition effect whereas more than 8 phr would result in too low a sensitivity. The organic nitrogen-containing compound used herein is preferably a compound capable of suppressing the rate of diffusion when the acid generated by the acid generator diffuses within the resist film. The inclusion of this type of organic nitrogen-containing compound holds down the rate of acid diffusion within the resist film, resulting in better resolution. In addition, it suppresses changes in sensitivity following exposure and reduces substrate and environment dependence, as well as improving the exposure latitude and the pattern profile.

If desired, a surfactant may be used in the resist composition. Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Fluorad FC-430 and FC-431 from Sumitomo 3M, Ltd., Surflon S-141, S-145, KH-10, KH-20, KH-30 and KH-40 from Asahi Glass Co., Ltd., Unidyne DS-401, DS-403 and DS-451 from Daikin Industry Co., Ltd., Megaface F-8151 from DIC Corp., and X-70-092 and X-70-093 from Shin-Etsu Chemical Co., Ltd. Preferred surfactants are Fluorad FC-430 from Sumitomo 3M, Ltd., KH-20 and KH-30 from Asahi Glass Co., Ltd., and X-70-093 from Shin-Etsu Chemical Co., Ltd.

Optionally, a polymer may be added to the resist composition of the invention which will locally segregate at the top of a coating and functions to adjust a hydrophilic/hydrophobic balance at the surface, to enhance water repellency, or to prevent low-molecular-weight components from flowing into or out of the coating when the coating comes in contact with water or similar liquids. The amount of functional polymer added is as used in resist compositions of this type as long as it does not compromise the objects of the invention, and is preferably up to 15 parts, and more preferably up to 10 parts by weight per 100 parts by weight of the base resin.

Preferred examples of the functional polymer which will segregate at the coating top include polymers and copolymers comprising fluorinated units of one or more types, and copolymers comprising fluorinated units and other units. Illustrative examples of suitable fluorinated units and other units are shown below, but not limited thereto.

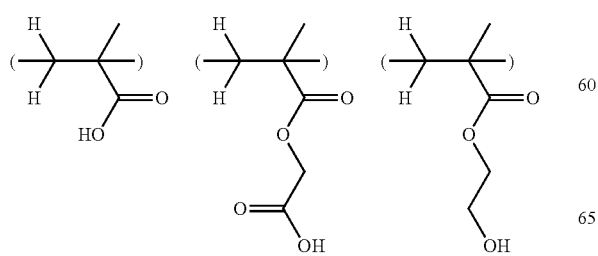

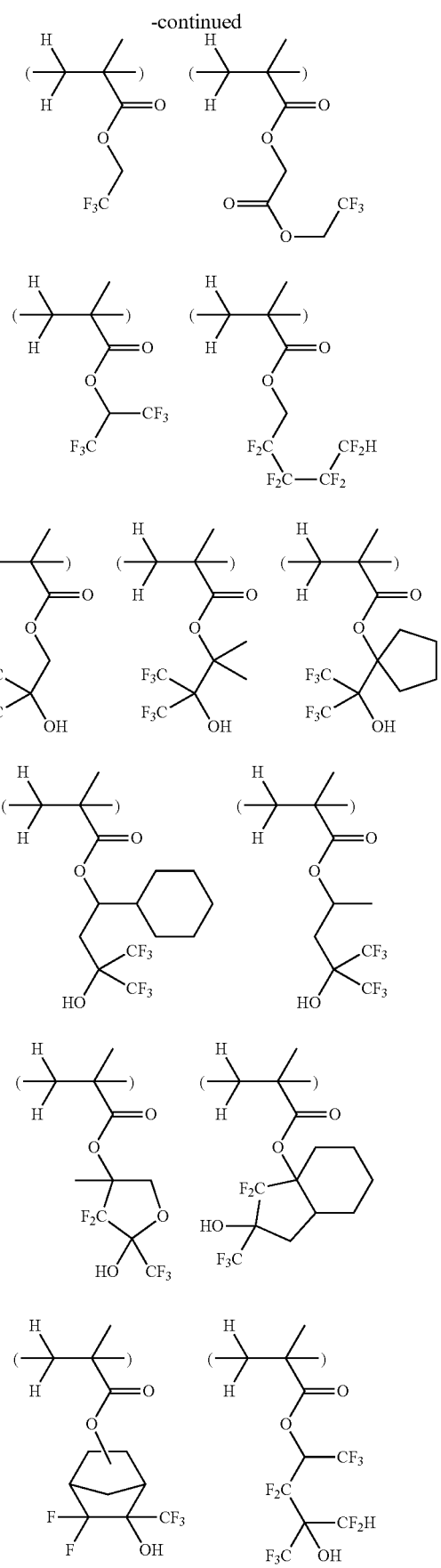

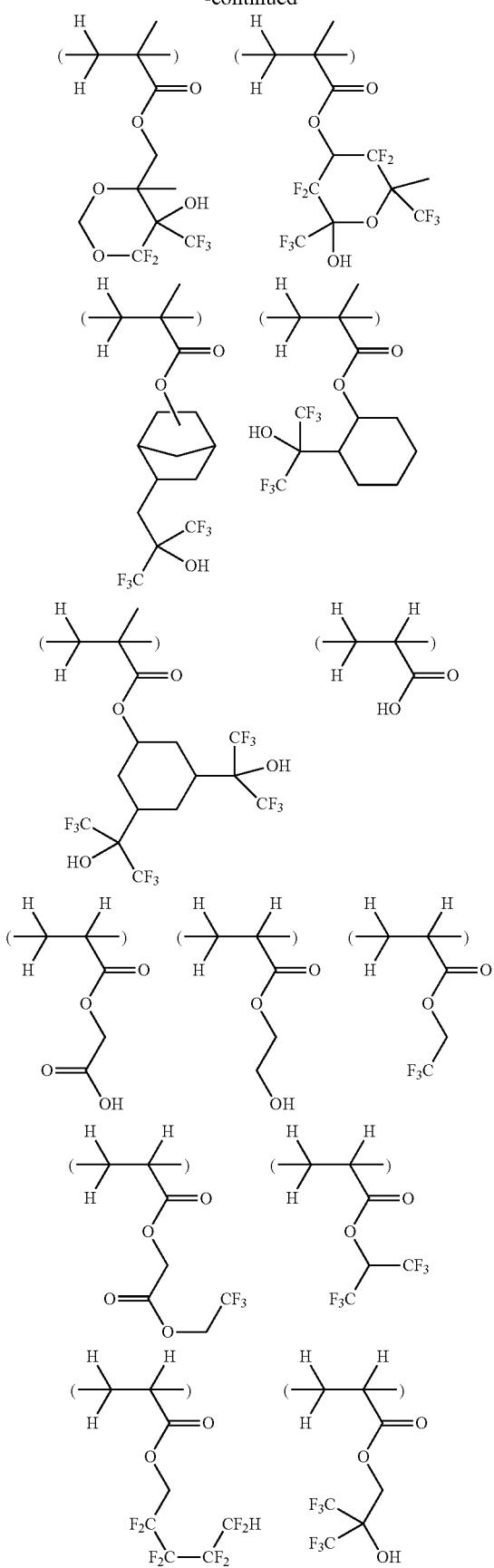
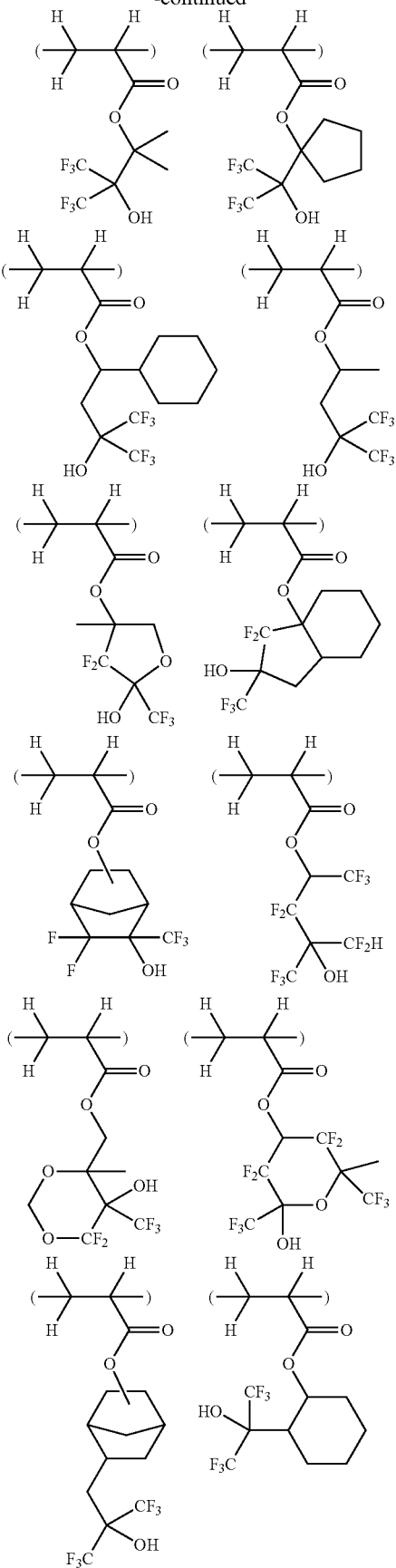

-continued

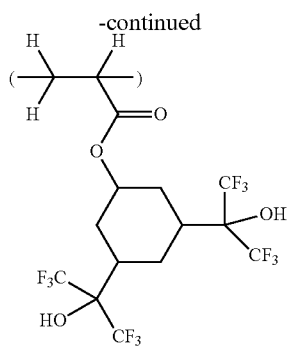

The functional polymer which will segregate at the coating top should preferably have a weight average molecular weight of 1,000 to 50,000, more preferably 2,000 to 20,000, as measured by GPC versus polystyrene standards. Outside the range, the polymer may have insufficient surface-modifying effect or cause development defects.

While the resist composition of the invention typically comprises a polymer, acid generator, organic solvent and organic nitrogen-containing compound as described above, there may be added optional other ingredients such as dissolution inhibitors, acidic compounds, stabilizers, and dyes. Optional ingredients may be added in conventional amounts so long as this does not compromise the objects of the invention.

Process

Pattern formation using the resist composition of the invention may be performed by well-known lithography processes. The process generally involves coating, heat treatment (or prebaking), exposure, heat treatment (post-exposure baking, PEB), and development. If necessary, any additional steps may be added.

For pattern formation, the resist composition is first applied onto a substrate (on which an integrated circuit is to be formed, e.g., Si, $SiO_2$, SiN, SiON, TiN, WSi, BPSG, SOG, organic antireflective coating, Cr, CrO, CrON, MoSi, etc.) by a suitable coating technique such as spin coating, roll coating, flow coating, dip coating, spray coating or doctor coating. The coating is prebaked on a hot plate at a temperature of 60 to 150° C. for about 1 to 10 minutes, preferably 80 to 140° C. for 1 to 5 minutes. The resulting resist film is generally 0.01 to 2.0 µm thick.

A relationship of a reduced thickness of resist film to an etch selectivity ratio between resist film and processable substrate imposes severer limits on the process. Under consideration is the tri-layer process in which a resist layer, a silicon-containing intermediate layer, an undercoat layer having a high carbon density and high etch resistance, and a processable substrate are laminated in sequence from top to bottom. On etching with oxygen gas, hydrogen gas, ammonia gas or the like, a high etch selectivity ratio is available between the silicon-containing intermediate layer and the undercoat layer, which allows for thickness reduction of the silicon-containing intermediate layer. A relatively high etch selectivity ratio is also available between the monolayer resist and the silicon-containing intermediate layer, which allows for thickness reduction of the monolayer resist. The method for forming the undercoat layer in this case includes a coating and baking method and a CVD method. In the case of coating, novolac resins and resins obtained by polymerization of fused ring-containing olefins are used. In the CVD film formation, gases such as butane, ethane, propane, ethylene and acetylene are used. For the silicon-containing intermediate layer, either a coating method or a CVD method may be employed. The coating method uses silsesquioxane, polyhedral oligomeric silsesquioxane (POSS) and the like while the CVD method uses silane gases as the reactant. The silicon-containing intermediate layer may have an antireflection function with a light absorbing ability and have photo-absorptive groups like phenyl groups, or it may be a SiON film. An organic film may be formed between the silicon-containing intermediate layer and the photoresist, and the organic film in this case may be an organic antireflective coating. After the photoresist film is formed, deionized water rinsing (or post-soaking) may be carried out for extracting the photoacid generator and the like from the film surface or washing away particles, or a protective film may be coated.

With a mask having a desired pattern placed above the resist film, the resist film is then exposed to radiation such as UV, deep-UV, electron beams, x-rays, excimer laser light, γ-rays and synchrotron radiation. The exposure dose is preferably about 1 to 200 $mJ/cm^2$, more preferably about 10 to 100 $mJ/cm^2$. The film is further baked (PEB) on a hot plate at 60 to 150° C. for 1 to 5 minutes, preferably 80 to 120° C. for 1 to 3 minutes. Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle or spray techniques. In this way, a desired resist pattern is formed on the substrate. It is appreciated that the resist composition of the invention is suited for micro-patterning using such high-energy radiation as deep UV with a wavelength of 254 to 193 nm, vacuum UV with a wavelength of 157 nm, electron beams, soft x-rays, x-rays, excimer laser light, γ-rays and synchrotron radiation, and best suited for micro-patterning using high-energy radiation in the wavelength range of 180 to 200 nm.

Immersion lithography can be applied to the resist composition of the invention. The ArF immersion lithography uses a liquid having a refractive index of at least 1 and highly transparent at the exposure wavelength such as deionized water or alkanes as the immersion solvent. The immersion lithography involves prebaking a resist film and exposing the resist film to light through a projection lens, with deionized water or similar liquid interposed between the resist film and the projection lens. Since this allows projection lenses to be designed to a numerical aperture (NA) of 1.0 or higher, formation of finer patterns is possible. The immersion lithography is important for the ArF lithography to survive to the 45-nm node, with a further development thereof being accelerated. In the case of immersion lithography, deionized water rinsing (or post-soaking) may be carried out after exposure for removing water droplets left on the resist film, or a protective coating may be applied onto the resist film after pre-baking for preventing any dissolution from the resist and improving water slip on the film surface.

The resist protective coating used in the immersion lithography is preferably formed from a solution of a polymer having 1,1,1,3,3,3-hexafluoro-2-propanol residue which is insoluble in water, but dissolvable in an alkaline developer liquid, in a solvent selected from alcohols of at least 4 carbon atoms, ethers of 8 to 12 carbon atoms, and mixtures thereof.

The technique enabling the ArF lithography to survive to the 32-nm node is a double patterning process. The double patterning process includes a trench process of processing an underlay to a 1:3 trench pattern by a first step of exposure and etching, shifting the position, and forming a 1:3 trench pattern by a second step of exposure for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

EXAMPLE

Examples are given below by way of illustration and not by way of limitation. Mw and Mn are weight and number average molecular weights, respectively, as measured by GPC versus polystyrene standards, and Mw/Mn is a polydispersity index. Me stands for methyl.

Monomer Synthesis

Synthesis Example 1

Fluorinated monomers were synthesized according to the following formulation.

Synthesis Example 1-1

Synthesis of Monomer 1

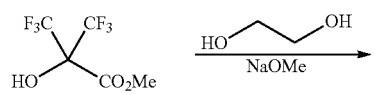

Synthesis Example 1-1-1

Synthesis of Starting Alcohol 1

A flask equipped with a distillation column was charged with 20.0 g of methyl 3,3,3-trifluoro-2-hydroxy-2-(trifluoromethyl)propionate, 16.5 g of ethylene glycol, 50 mL of benzene, and 0.9 g of sodium methoxide (28 wt % methanol solution). In a nitrogen atmosphere, the reaction mixture was heated under reflux for 6 hours while methanol formed during reaction was sequentially distilled off. This was followed by ordinary aqueous work-up, solvent removal by distillation, and purification by distillation, obtaining 17.2 g of the starting Alcohol 1 (yield 76%).

Boiling point: 64° C./170 Pa

Synthesis Example 1-1-2

Synthesis of Monomer 1

To 3.30 g of Starting Alcohol 1 were added 1.92 g of methacrylic anhydride, 10 mL of toluene, and 0.05 g of methanesulfonic acid. In a nitrogen atmosphere, the reaction mixture was heated and stirred at 50° C. for 10 hours. This was followed by ordinary aqueous work-up, solvent removal by distillation, and purification by distillation, obtaining 3.40 g of Monomer 1 (yield 81%).

Boiling point: 51° C./17 Pa

IR (thin film):
ν=3392, 2967, 1766, 1722, 1639, 1456, 1375, 1317, 1299, 1241, 1162, 1056, 1025, 1010, 977 $cm^{-1}$ $^1$H-NMR (600 MHz in DMSO-$d_6$):
δ=1.84 (3H, m), 4.34 (2H, m), 4.62 (2H, m), 5.69 (1H, m), 5.99 (1H, m), 9.23 (1H, s) ppm $^{19}$F-NMR (565 MHz in DMSO-$d_6$): δ=−75.03 (6F, s) ppm Synthesis Example 1-2

Synthesis of Monomer 2

Monomer 2 was synthesized by the same procedure as Synthesis Example 1-1-2 aside from using acrylic anhydride instead of methacrylic anhydride. Two step yield 58%.

Synthesis Example 1-3

Synthesis of Monomer 3

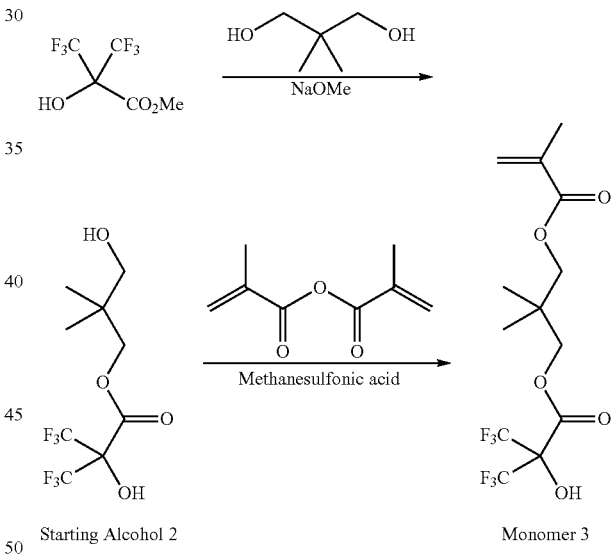

Synthesis Example 1-3-1

Synthesis of Starting Alcohol 2

Starting Alcohol 2 was synthesized by the same procedure as Synthesis Example 1-1-1 aside from using neopentyl glycol instead of ethylene glycol. Yield 72%.

IR (thin film):
ν=3546, 3515, 3164, 2978, 2950, 2889, 1764, 1480, 1379, 1328, 1256, 1225, 1162, 1040, 1014, 998, 978 $cm^{-1}$ $^1$H-NMR (600 MHz in DMSO-$d_6$):
δ=0.84 (6H, s), 3.17 (2H, s), 4.10 (2H, s), 4.70 (1H, s), 9.11 (1H, s) ppm $^{19}$F-NMR (565 MHz in DMSO-$d_6$): δ=−75.06 (6F, s) ppm Synthesis Example 1-3-2

Synthesis of Monomer 3

Monomer 3 was synthesized by the same procedure as Synthesis Example 1-1-2 aside from using Starting Alcohol 2 instead of Starting Alcohol 1. Yield 92%.

Boiling point: 69° C./12 Pa
IR (thin film):
ν=3460, 3385, 2973, 1765, 1716, 1639, 1477, 1457, 1376, 1322, 1241, 1225, 1162, 1012, 977, 946 cm$^{-1}$
$^1$H-NMR (600 MHz in DMSO-$d_6$):
δ=0.95 (6H, s), 1.86 (3H, s), 3.89 (2H, s), 4.19 (2H, s), 5.67 (1H, m), 6.03 (1H, m), 9.21 (1H, s) ppm
$^{19}$F-NMR (565 MHz in DMSO-$d_6$): δ=−75.14 (6F, s) ppm Synthesis Example 1-4

Synthesis of Monomer 4

Monomer 4 was synthesized by the same procedure as Synthesis Example 1-1-2 aside from using Starting Alcohol 2 instead of Starting Alcohol 1 and acrylic anhydride instead of methacrylic anhydride. Two-step yield 59%.

Synthesis Example 1-5

Synthesis of Monomer 5

Monomer 5 was synthesized by the same procedure as Synthesis Examples 1-1-1 and 1-1-2 aside from using Starting Alcohol 2 instead of Starting Alcohol 1 and α-trifluoromethylacrylic anhydride instead of methacrylic anhydride. Two-step yield 48%.

Synthesis Example 1-6

Synthesis of Monomer 6

Monomer 6 was synthesized by the same procedure as Synthesis Examples 1-1-1 and 1-1-2 aside from using 4-methylpentane-1,3-diol instead of ethylene glycol. Two-step yield 38%.

Boiling point: 85-86° C./28 Pa
IR (thin film):
ν=3459, 2972, 1760, 1716, 1638, 1469, 1373, 1324, 1241, 1224, 1009, 977 cm$^{-1}$
$^1$H-NMR (600 MHz in DMSO-$d_6$):
δ=0.87 (6H, t), 1.87 (3H, s), 1.90-2.03 (3H, m), 4.24-4.31 (1H, m), 4.33-4.37 (1H, m), 4.78-4.82 (1H, m), 5.66 (1H, m), 6.03 (1H, m), 9.13 (1H, s) ppm
$^{19}$F-NMR (565 MHz in DMSO-$d_6$): δ=−75.09 (6F, s) ppm Synthesis Example 1-7

Synthesis of Monomer 7

Monomer 7 was synthesized by the same procedure as Synthesis Examples 1-1-1 and 1-1-2 aside from using 3-methylbutane-1,3-diol instead of ethylene glycol. Two-step yield 42%.

Synthesis Example 1-8

Synthesis of Monomer 8

Monomer 8 was synthesized by the same procedure as Synthesis Examples 1-1-1 and 1-1-2 aside from using neopentyl glycol instead of ethylene glycol. Two-step yield 37%.

IR (thin film):
ν=3461, 3334, 2995, 1763, 1711, 1640, 1474, 1317, 1303, 1246, 1220, 1163, 1016, 975 cm$^{-1}$
$^1$H-NMR (600 MHz in DMSO-$d_6$):
δ=1.04 (3H, s), 1.86 (3H, s), 4.02 (2H, s), 4.31 (4H, s), 5.69 (1H, m), 6.06 (1H, m), 9.30 (2H, s) ppm
$^{19}$F-NMR (565 MHz in DMSO-$d_6$): δ=−75.28 (12F, s) ppm Synthesis Example 1-9

Synthesis of Monomer 9

Monomer 9 was synthesized by the same procedure as Synthesis Examples 1-1-1 and 1-1-2 aside from using neopentyl glycol instead of ethylene glycol and acrylic anhydride instead of methacrylic anhydride. Two-step yield 34%.

Synthesis Example 1-10

Synthesis of Monomer 10

Monomer 10 was synthesized by the same procedure as Synthesis Examples 1-1-1 and 1-1-2 aside from using glycerol instead of ethylene glycol. Two-step yield 39%.

Boiling point: 97-98° C./11 Pa
IR (thin film):
ν=3469, 2972, 1766, 1722, 1638, 1455, 1382, 1314, 1227, 1161, 1013, 978 cm$^{-1}$
$^1$H-NMR (600 MHz in DMSO-$d_6$):
δ=1.81 (3H, s), 4.55-4.68 (4H, m), 5.39-5.43 (1H, m), 5.70 (1H, m), 5.97 (1H, m), 9.30 (2H, s) ppm
$^{19}$F-NMR (565 MHz in DMSO-$d_6$): δ=−75.20 (12F, s) ppm Synthesis Example 1-11

Synthesis of Monomer 11

Monomer 11 was synthesized by the same procedure as Synthesis Examples 1-1-1 and 1-1-2 aside from using 2,2-difluoro-4-methylbutane-1,3-diol instead of ethylene glycol. Two-step yield 31%.

Synthesis Example 1-12

Synthesis of Monomer 12

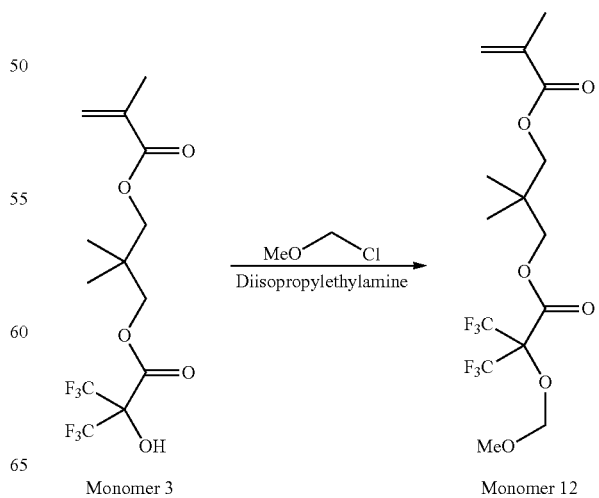

Monomer 3           Monomer 12

At a temperature below 20° C., 9.7 g of chloromethyl methyl ether was added dropwise to a mixture of 36.6 g of Monomer 3, 16.2 g of diisopropylethylamine, and 70.0 g of acetonitrile. The mixture was stirred at the temperature for 3 hours. This was followed by ordinary aqueous work-up, solvent removal by distillation, and purification by distillation, obtaining 39.8 g of Monomer 12 (yield 97%).

Boiling point: 78-79° C./12 Pa

IR (thin film):

ν=2970, 2935, 1766, 1723, 1639, 1477, 1402, 1374, 1296, 1257, 1229, 1161, 1074, 1028, 994, 935 cm$^{-1}$ $^1$H-NMR (600 MHz in DMSO-d$_6$):

δ=0.97 (6H, s), 1.86 (3H, s), 3.38 (3H, s), 3.89 (2H, s), 4.20 (2H, s), 5.04 (2H, s), 5.67 (1H, m), 6.03 (1H, m) ppm $^{19}$F-NMR (565 MHz in DMSO-d$_6$): δ=−72.49 (6F, s) ppm Synthesis Example 1-13

Synthesis of Monomer 13

Monomer 13 was synthesized by the same procedure as Synthesis Example 1-12 aside from using isobutyric acid chloride instead of chloromethyl methyl ether. Yield 96%.

Boiling point: 90-91° C./11 Pa

IR (thin film):

ν=2979, 1773, 1724, 1639, 1472, 1401, 1374, 1260, 1235, 1163, 1117, 1086, 1041, 999, 943 cm$^{-1}$ $^1$H-NMR (600 MHz in DMSO-d$_6$):

δ=0.95 (6H, s), 1.14 (6H, d), 1.86 (3H, s), 2.86 (1H, sept), 3.85 (2H, s), 4.17 (2H, s), 5.67 (1H, m), 6.03 (1H, m) ppm $^{19}$F-NMR (565 MHz in DMSO-d$_6$): δ=−71.57 (6F, s) ppm Synthesis Example 1-14

Synthesis of Monomer 14

Monomer 14 was synthesized by the same procedure as Synthesis Example 1-12 aside from using Monomer 8 instead of Monomer 3. Yield 96%.

Boiling point: 116-117° C./9 Pa

IR (thin film):

ν=2970, 2837, 1769, 1726, 1640, 1474, 1453, 1404, 1380, 1295, 1255, 1229, 1159, 1145, 1074, 1029, 994, 934 cm$^{-1}$ $^1$H-NMR (600 MHz in DMSO-d$_6$):

δ=1.05 (3H, s), 1.87 (3H, s), 3.38 (6H, s), 4.01 (2H, s), 4.31-4.36 (4H, m), 5.05 (4H, s), 5.70 (1H, m), 6.07 (1H, m) ppm $^{19}$F-NMR (565 MHz in DMSO-d$_6$): δ=−72.58 (12F, s) ppm Synthesis Example 1-15

Synthesis of Monomer 15

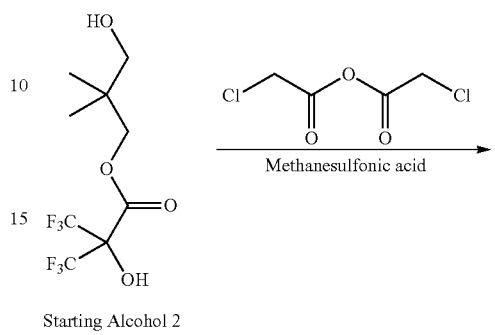

Starting Alcohol 2

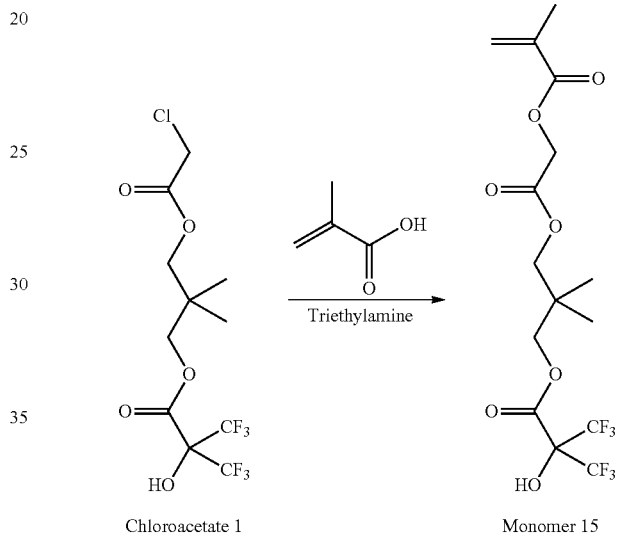

Chloroacetate 1  Monomer 15

Synthesis Example 1-15-1

Synthesis of Chloroacetate 1

Chloroacetate 1 was synthesized by the same procedure as Synthesis Example 1-1-2 aside from using Starting Alcohol 2 instead of Starting Alcohol 1 and chloroacetic anhydride instead of methacrylic anhydride. Yield 88%.

Synthesis Example 1-15-2

Synthesis of Monomer 15

At a temperature below 25° C., a mixture of 137 g of triethylamine and 100 g of dimethylformamide was added dropwise to a mixture of 129 g of methacrylic acid, 139 g of Chloroacetate 1 (Synthesis Example 1-15-1), 22.0 g of sodium iodide and 400 g of dimethylformamide. The mixture was stirred at the temperature for 8 hours. Below 30° C., 300 g of 10% hydrochloric acid was added. This was followed by ordinary work-up and vacuum distillation, obtaining 132 g of the target compound (yield 84%).

Monomers 1 to 15 of Synthesis Examples are identified below by their structural formulae.
Monomer 1
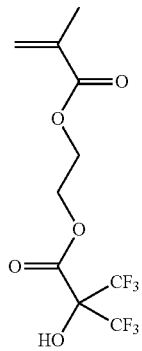
Monomer 2
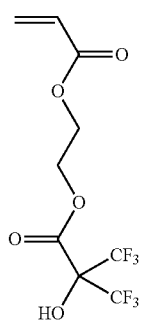
Monomer 3
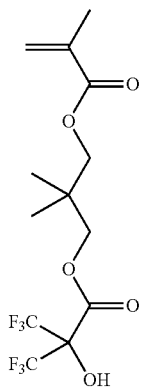
Monomer 4
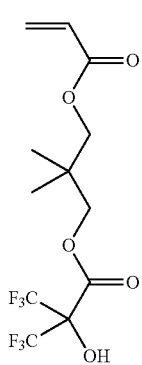
Monomer 5
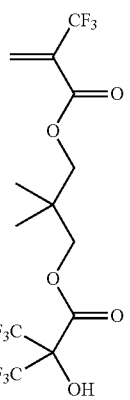
Monomer 6
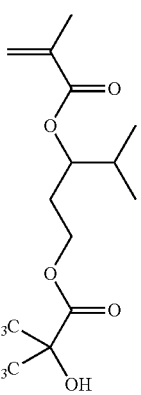
Monomer 7
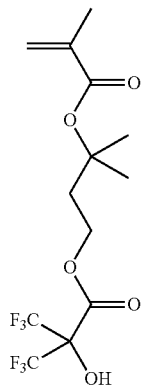
Monomer 8
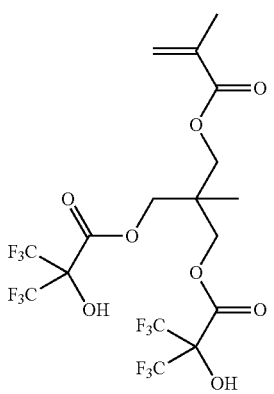

Monomer 9
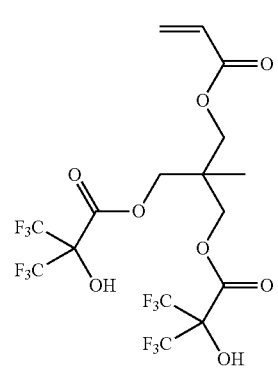
Monomer 10
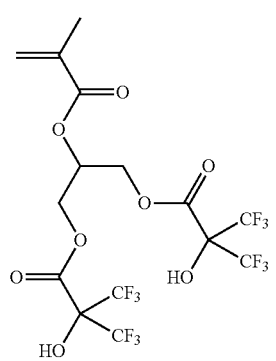
Monomer 11
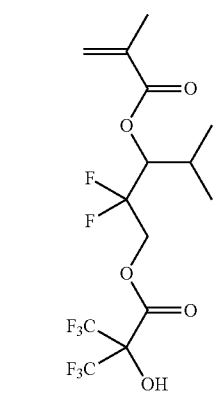
Monomer 12
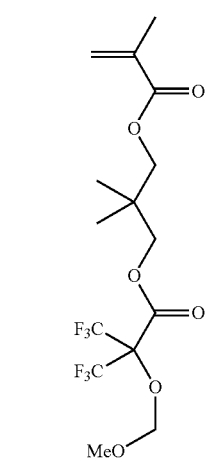
Monomer 13
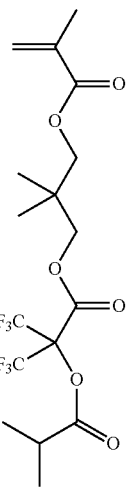
Monomer 14
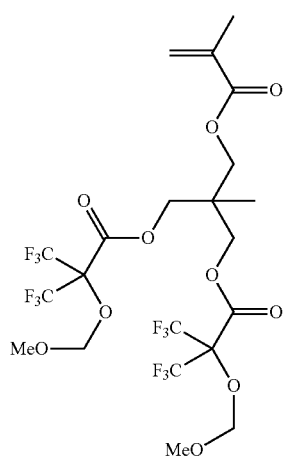
Monomer 15
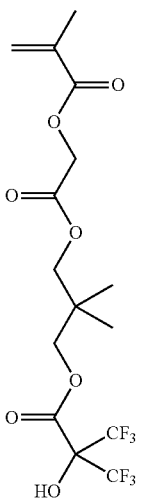
Polymer Synthesis
Synthesis Example 2
Polymers were synthesized according to the following formulation.

Synthesis Example 2-1

Synthesis of Polymer 1

In a nitrogen atmosphere, 29.2 g of PGMEA was stirred at 80° C., and a solution of 27.1 g of Monomer 1, 22.9 g of 3-ethyl-3-exo-tetracyclo[4.4.0.1$^{2,5}$.1$^{7,10}$]dodecanyl methacrylate, 1097 mg of 2,2'-azobisisobutyronitrile, and 196 mg of 2-mercaptoethanol in 87.5 g of PGMEA was added dropwise thereto over 4 hours. Stirring was continued at 80° C. for a further 2 hours. The polymerization solution was cooled to room temperature, and with vigorous stirring, added dropwise to 1,000 mL of n-hexane. The resulting solid was collected by filtration and vacuum dried at 50° C. for 15 hours, yielding a polymer in white powder solid form, designated Polymer 1. Amount 46.5 g, yield 93%.

Polymer 1

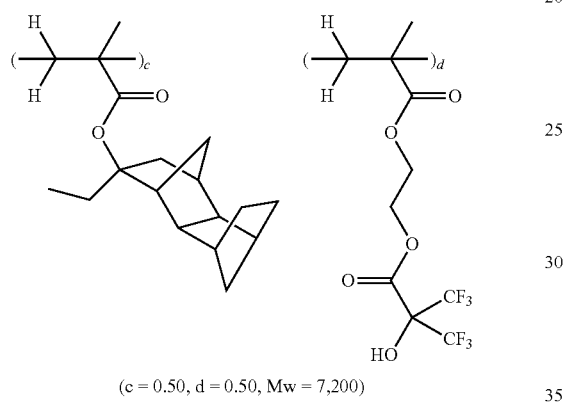

(c = 0.50, d = 0.50, Mw = 7,200)

Synthesis Examples 2-2 to 2-12 and Comparative Synthesis Examples 1-1 to 1-4

Synthesis of Polymers 2 to 12 and Comparative Polymers 1 to 4

Polymers 2 to 12 and Comparative Polymers 1 to 4 were synthesized by the same procedure as Synthesis Example 2-1 except that the type and proportion of monomers were changed. The structure and compositional proportion (molar ratio) of these polymers are shown below.

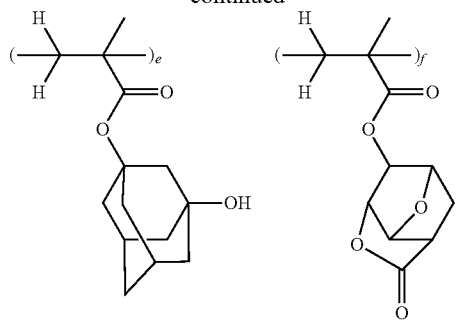

(c = 0.30, d = 0.10, e = 0.15, f = 0.45, Mw = 6,400)

Polymer 3

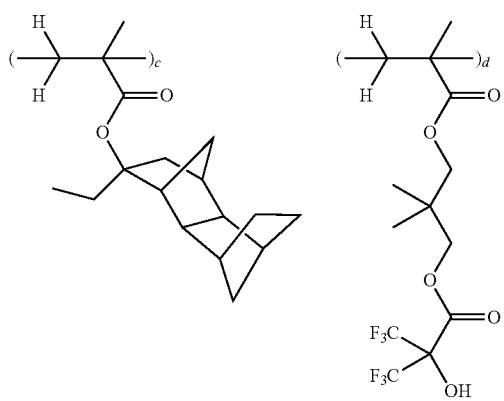

(c = 0.30, d = 0.10, e = 0.15, f = 0.45, Mw = 6,600)

Polymer 2

Polymer 4

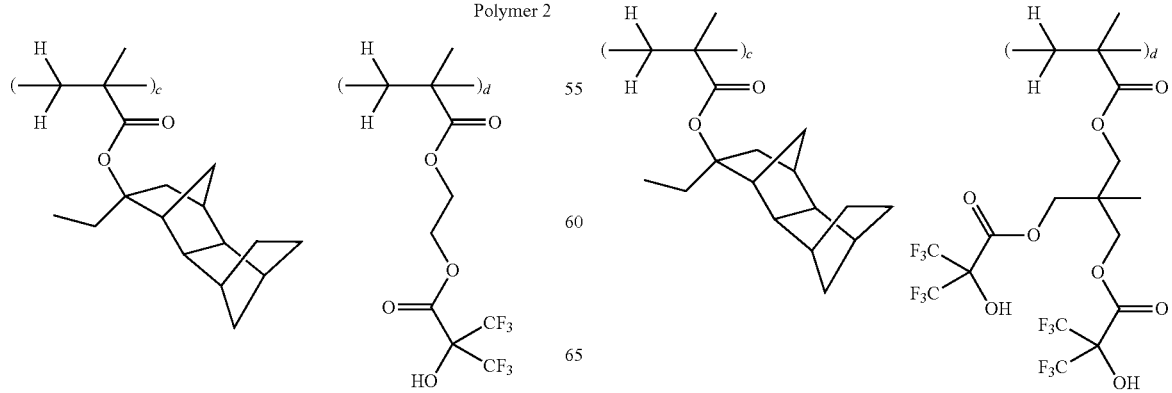

-continued
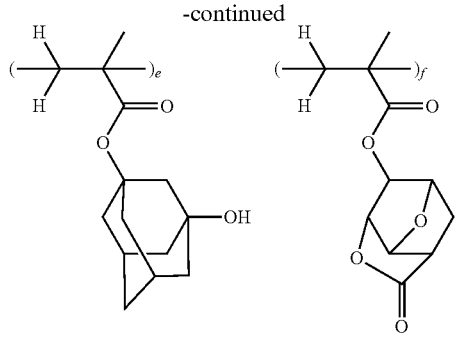
(c = 0.30, d = 0.10, e = 0.15, f = 0.45, Mw = 7,100)
Polymer 5
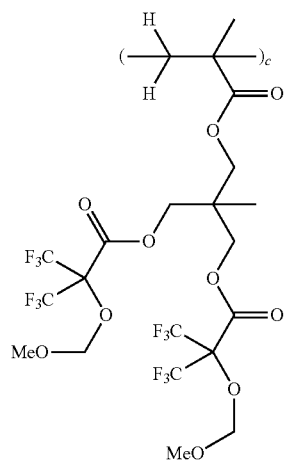
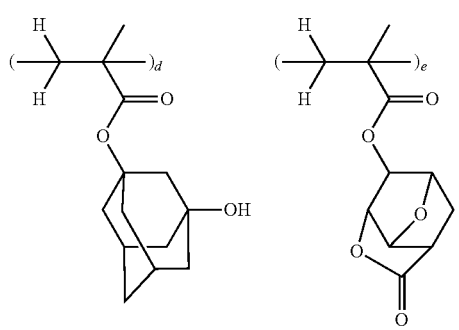
(c = 0.50, d = 0.10, e = 0.40, Mw = 7,300)
Polymer 6
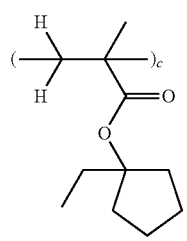
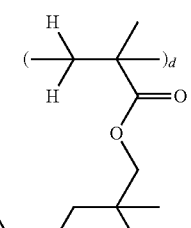
-continued
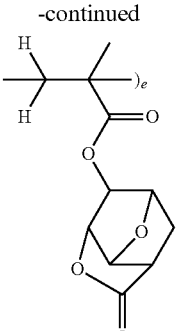
(c = 0.50, d = 0.10, e = 0.40, Mw = 7,000)
Polymer 7
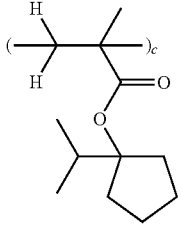
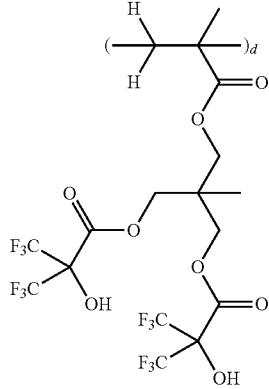
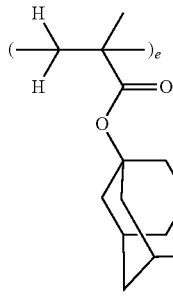
(c = 0.50, d = 0.10, e = 0.10, f = 0.30, Mw = 7,100)
Polymer 8
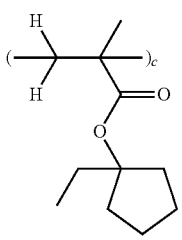
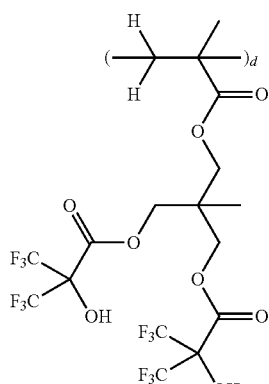

-continued
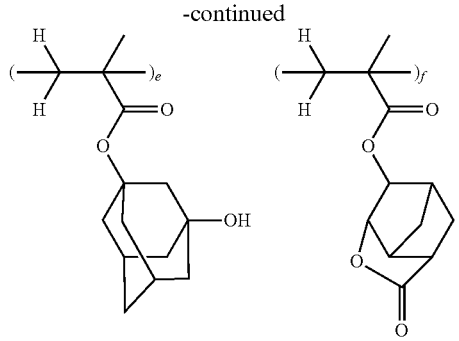
(c = 0.50, d = 0.10, e = 0.10, f = 0.30, Mw = 7,200)
Polymer 9
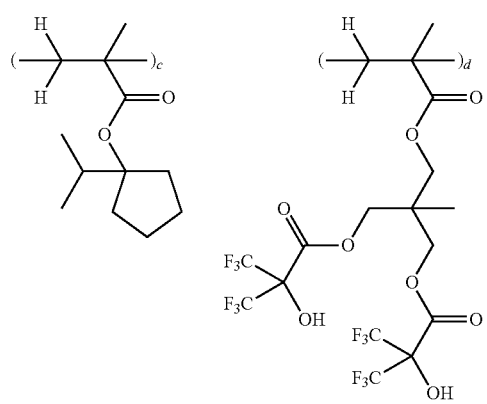
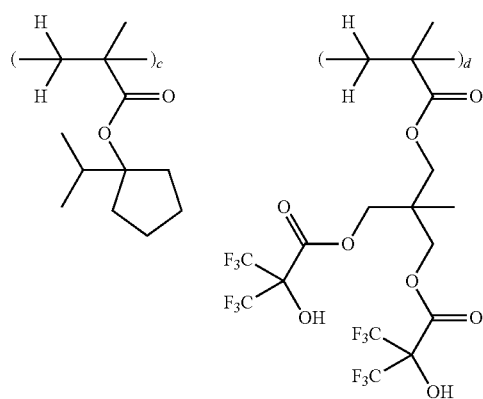
(c = 0.50, d = 0.10, e = 0.10, f = 0.30, Mw = 7,300)
Polymer 10
-continued
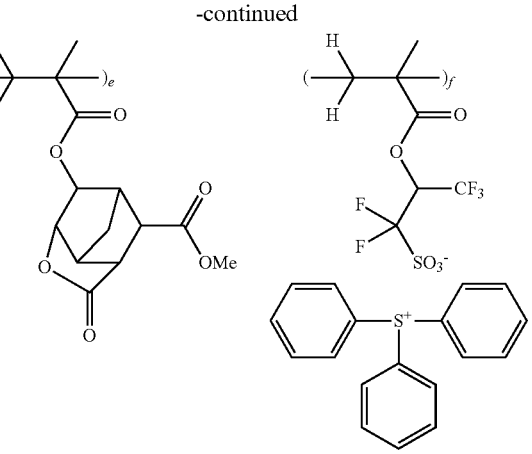
(c = 0.50, d = 0.05, e = 0.40, f = 0.05, Mw = 7,900)
Polymer 11
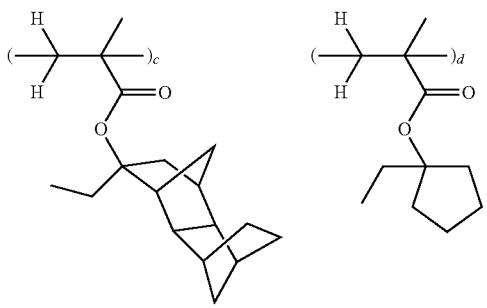
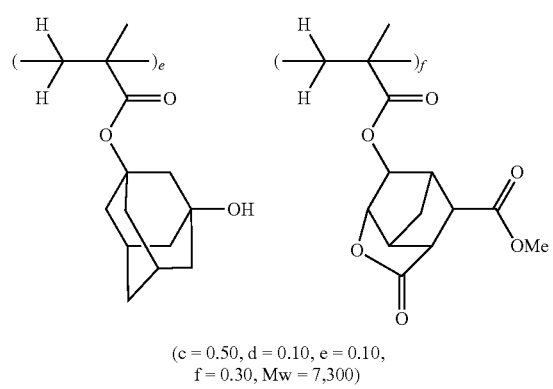
(c = 0.20, d = 0.30, e = 0.10, f = 0.40, Mw = 7,100)
Polymer 12
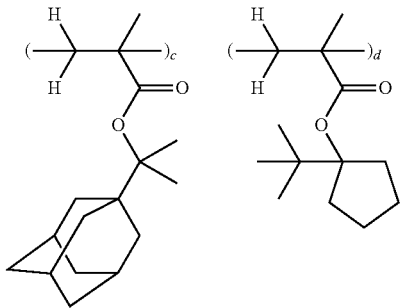

-continued
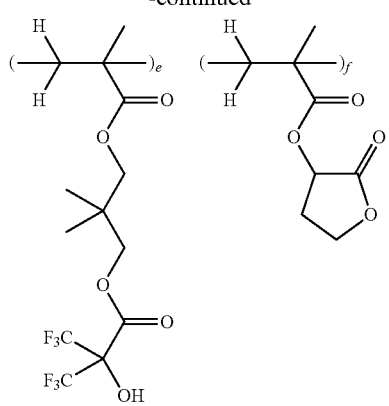
(c = 0.30, d = 0.20, e = 0.10, f = 0.40, Mw = 6,800)
Comparative Polymer 1
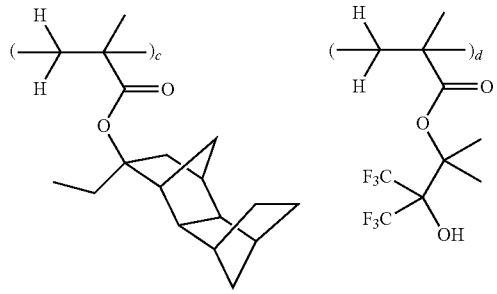
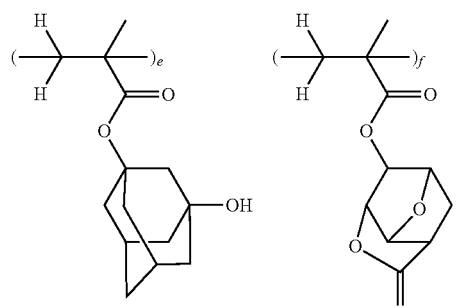
(c = 0.30, d = 0.10, e = 0.15, f = 0.45, Mw = 6,200)
Comparative Polymer 2
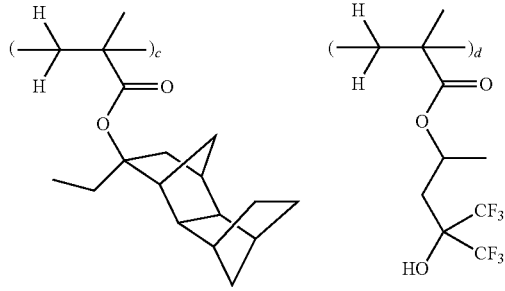
-continued
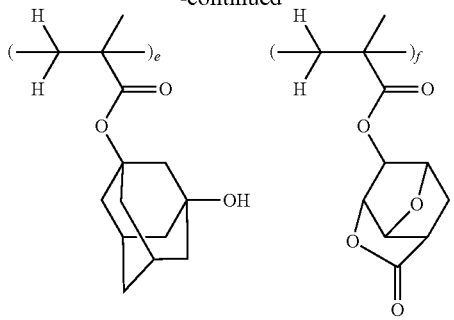
(c = 0.30, d = 0.10, e = 0.15, f = 0.45, Mw = 6,100)
Comparative Polymer 3
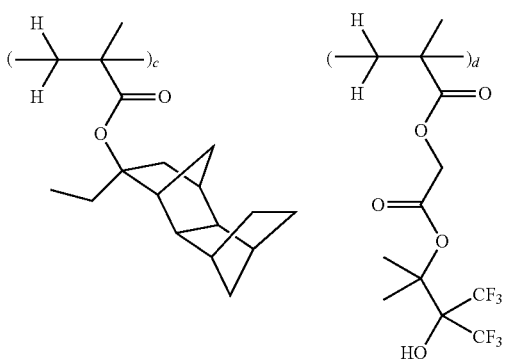
(c = 0.30, d = 0.10, e = 0.15, f = 0.45, Mw = 6,400)
Comparative Polymer 4
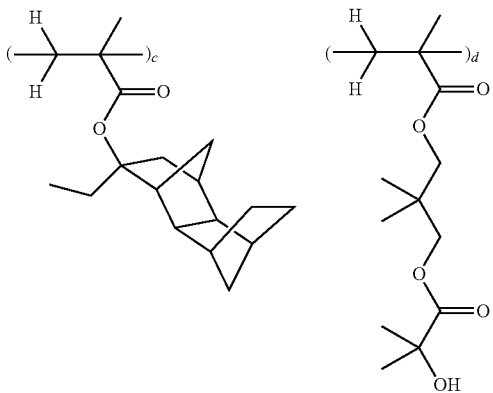

-continued

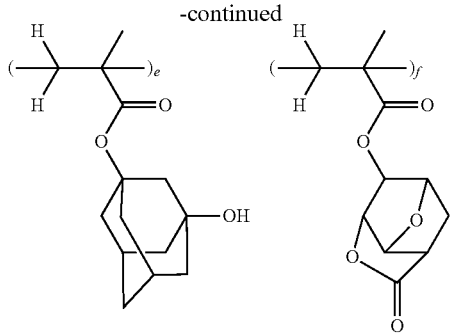

(c = 0.30, d = 0.10, e = 0.15, f = 0.45, Mw = 6,200)

Preparation of Resist Compositions

Examples 1-1 to 1-15 & Comparative Examples 1-1 to 1-4

Resist compositions were prepared by using inventive Polymers 1 to 12 or Comparative Polymers 1 to 4 as the base resin, and dissolving the polymer, an acid generator (PAG), and a basic compound (Base) in a solvent mixture in accordance with the recipe shown in Table 1. These compositions were each filtered through a Teflon® filter having a pore size of 0.2 μm, thereby giving inventive resist solutions R-01 to 15 and comparative resist solutions R-16 to 19. The solvent contained 0.01 wt % of surfactant KH-20 (Asahi Glass Co., Ltd.).

TABLE 1

|  | Resist | Resin (pbw) | PAG (pbw) | Base (pbw) | Solvent 1 (pbw) | Solvent 2 (pbw) |
| --- | --- | --- | --- | --- | --- | --- |
| Example 1-1 | R-01 | Polymer 1 (80) | PAG-1 (15.0) | Base-1 (4.0) | PGMEA (2,700) | CyHO (300) |
| Example 1-2 | R-02 | Polymer 2 (80) | PAG-1 (15.0) | Base-1 (4.0) | PGMEA (2,700) | CyHO (300) |
| Example 1-3 | R-03 | Polymer 3 (80) | PAG-1 (15.0) | Base-1 (4.0) | PGMEA (2,700) | CyHO (300) |
| Example 1-4 | R-04 | Polymer 4 (80) | PAG-1 (15.0) | Base-1 (4.0) | PGMEA (2,700) | CyHO (300) |
| Example 1-5 | R-05 | Polymer 5 (80) | PAG-1 (15.0) | Base-1 (4.0) | PGMEA (2,700) | CyHO (300) |
| Example 1-6 | R-06 | Polymer 6 (80) | PAG-1 (15.0) | Base-1 (4.0) | PGMEA (2,700) | CyHO (300) |
| Example 1-7 | R-07 | Polymer 7 (80) | PAG-1 (15.0) | Base-1 (4.0) | PGMEA (2,700) | CyHO (300) |
| Example 1-8 | R-08 | Polymer 8 (80) | PAG-1 (15.0) | Base-1 (4.0) | PGMEA (2,700) | CyHO (300) |
| Example 1-9 | R-09 | Polymer 9 (80) | PAG-1 (15.0) | Base-1 (4.0) | PGMEA (2,700) | CyHO (300) |
| Example 1-10 | R-10 | Polymer 10 (80) | — | Base-1 (4.0) | PGMEA (2,700) | CyHO (300) |
| Example 1-11 | R-11 | Polymer 11 (80) | PAG-1 (15.0) | Base-1 (4.0) | PGMEA (2,700) | CyHO (300) |
| Example 1-12 | R-12 | Polymer 12 (80) | PAG-1 (15.0) | Base-1 (4.0) | PGMEA (2,700) | CyHO (300) |
| Example 1-13 | R-13 | Polymer 3 (80) | PAG-1 (15.0) | Base-1 (4.0) | PGMEA (2,700) | GBL (300) |
| Example 1-14 | R-14 | Polymer 4 (80) | PAG-1 (15.0) | Base-1 (4.0) | PGMEA (2,700) | GBL (300) |
| Example 1-15 | R-15 | Polymer 10 (80) | — | Base-1 (4.0) | PGMEA (2,700) | GBL (300) |
| Comparative Example 1-1 | R-16 | Comparative Polymer 1 (80) | PAG-1 (15.0) | Base-1 (4.0) | PGMEA (2,700) | CyHO (300) |
| Comparative Example 1-2 | R-17 | Comparative Polymer 2 (80) | PAG-1 (15.0) | Base-1 (4.0) | PGMEA (2,700) | CyHO (300) |
| Comparative Example 1-3 | R-18 | Comparative Polymer 3 (80) | PAG-1 (15.0) | Base-1 (4.0) | PGMEA (2,700) | CyHO (300) |
| Comparative Example 1-4 | R-19 | Comparative Polymer 4 (80) | PAG-1 (15.0) | Base-1 (4.0) | PGMEA (2,700) | CyHO (300) |

* pbw: parts by weight

The acid generator, base and solvent shown in Table 1 have the following meanings.

PAG-1: triphenylsulfonium 2-(adamantane-1-carbonyloxy)-1,1,3,3,3-pentafluoropropanesulfonate
Base-1: tri(2-methoxymethoxyethyl)amine
PGMEA: 1-methoxyisopropyl acetate
CyHO: cyclohexanone
GBL: γ-butyrolactone Evaluation of Immersion Liquid Penetration Preventing Effect Examples 2-1 to 2-5 & Comparative Examples 2-1 and 2-2

A resist composition comprising the inventive polymer as a base resin was evaluated for the effect of preventing immersion liquid (water) from penetrating into a resist film. Specifically, the resist composition (R-01, 03, 05, 12, 13) or comparative resist composition (R-16 and 18) in Table 1 was coated onto a silicon wafer pretreated with hexamethyl disilazane (HMDS) and baked at 100° C. for 60 seconds to form a resist film of 50 nm thick.

An inclination contact angle meter Drip Master 500 by Kyowa Interface Science Co., Ltd. was used. While the resist-coated wafer was kept horizontal, 50 microliters (μl) of deionized water was dripped thereon to form a droplet. While the wafer was gradually inclined, the angle (sliding angle) at which the droplet started sliding down was determined as well as receding contact angle. The results are shown in Table 2.

TABLE 2

| | Resist | Sliding angle (°) | Receding contact angle (°) |
| --- | --- | --- | --- |
| Example 2-1 | R-01 | 13 | 70 |
| Example 2-2 | R-03 | 20 | 66 |
| Example 2-3 | R-05 | 12 | 72 |
| Example 2-4 | R-12 | 19 | 67 |
| Example 2-5 | R-13 | 19 | 66 |
| Comparative Example 2-1 | R-16 | 26 | 55 |
| Comparative Example 2-2 | R-18 | 25 | 54 |

As seen from Table 2, the resist compositions comprising the inventive polymers as the base resin have a smaller sliding angle and a larger receding contact angle, indicating that the resist films are effective for preventing penetration of immersion liquid (water). A smaller sliding angle also indicates an easier flow of water on the film, advantageously allowing for a higher scanning speed during scan exposure. A larger receding contact angle indicates that fewer liquid droplets are left during high-speed scan exposure.

Evaluation of Swell Reducing Effect

Examples 3-1 to 3-8 & Comparative Examples 3-1 to 3-4

A resist composition comprising the inventive polymer as the base resin was evaluated for swell reducing effect. Onto a silicon wafer pre-sprayed with hexamethyl disilazane (HMDS) at 90° C. for 90 seconds, the resist composition (R-01, 02, 04, 06 to 09, 11) or comparative resist composition (R-16 to 19) in Table 1 was spin coated and baked at 110° C. for 60 seconds to form a resist film of 200 nm thick. The wafer was exposed by means of an ArF excimer laser stepper (Nikon Corp., NA 0.68) at eleven (11) spots in different exposure doses. The exposure doses corresponded to 11 sensitivity values which included the center value given by a separately measured sensitivity (Eth, mJ/cm$^2$) and five up/down levels varying from the center value at a pitch of 5%. The wafer was post-exposure baked (PEB) at 110° C. for 90 seconds. At this point, the film thickness at different exposure dose spots was measured as a film thickness (Å) prior to development. Next, the wafer was immersed in a 2.38 wt % tetramethylammonium hydroxide aqueous solution for 200 seconds for development. At this point, the film thickness at different exposure dose spots was measured again as a film thickness (Å) after development. For each exposure spot, the film thickness (Å) prior to development and the film thickness (Å) after development were compared. A positive change of film thickness before and after development indicates that the film is swollen. A maximum change is reported as a swell (Å). The results are shown in Table 3.

TABLE 3

| | Resist composition | Swell (Å) |
| --- | --- | --- |
| Example 3-1 | R-01 | −150 |
| Example 3-2 | R-02 | −80 |
| Example 3-3 | R-04 | −120 |
| Example 3-4 | R-06 | −140 |
| Example 3-5 | R-07 | −130 |
| Example 3-6 | R-08 | −120 |
| Example 3-7 | R-09 | −100 |
| Example 3-8 | R-11 | −70 |
| Comparative Example 3-1 | R-16 | −30 |
| Comparative Example 3-2 | R-17 | −5 |
| Comparative Example 3-3 | R-18 | −20 |
| Comparative Example 3-4 | R-19 | 50 |

It is seen from the data in Table 3 that the resist composition within the scope of the invention exhibits a significant swell reducing effect.

Evaluation of Pattern Collapse of Resist Composition

Examples 4-1 to 4-15 & Comparative Examples 4-1 to 4-4

Each of inventive resist compositions (R-01 to 15) and comparative resist compositions (R-16 to 19) in Table 1 was spin coated on a silicon wafer having an antireflective coating (ARC-29A, Nissan Chemical Co., Ltd.) of 90 nm thick and baked at 100° C. for 60 seconds, forming a resist film of 100 nm thick. On the resist film, a resist protective material (SIOC-3 by Shin-Etsu Chemical Co., Ltd.) was spin coated and heat treated at 90° C. for 60 seconds to form a resist protective film of 50 nm thick. The wafer was exposed by means of an immersion ArF excimer laser stepper (Nikon Corp., NA 1.30) with a 6% halftone phase shift mask for transferring a given pattern on the mask to the resist film, post-exposure baked (PEB) for 60 seconds, and puddle developed with a 2.38 wt % tetramethylammonium hydroxide aqueous solution for 30 seconds, forming a 40 nm 1:1 line-and-space pattern. During the PEB, an optimum temperature for each resist composition was employed. The pattern as developed was observed under a top-down scanning electron microscope (SEM) for examining the dependence of pattern line width on exposure dose. In general, as the exposure dose increases, the line width becomes finer and the pattern is more prone to collapse. For areas of increasing exposure doses, the minimum line width above which the pattern did not collapse was determined and reported as limit collapse size (nm) in Table 4. A smaller size indicates better resistance to pattern collapse.

TABLE 4

| | Resist | PEB temperature | Limit collapse size |
|---|---|---|---|
| Example 4-1 | R-01 | 90° C. | 30 nm |
| Example 4-2 | R-02 | 105° C. | 30 nm |
| Example 4-3 | R-03 | 105° C. | 27 nm |
| Example 4-4 | R-04 | 100° C. | 27 nm |
| Example 4-5 | R-05 | 100° C. | 28 nm |
| Example 4-6 | R-06 | 95° C. | 29 nm |
| Example 4-7 | R-07 | 95° C. | 30 nm |
| Example 4-8 | R-08 | 105° C. | 27 nm |
| Example 4-9 | R-09 | 105° C. | 29 nm |
| Example 4-10 | R-10 | 105° C. | 26 nm |
| Example 4-11 | R-11 | 95° C. | 27 nm |
| Example 4-12 | R-12 | 95° C. | 28 nm |
| Example 4-13 | R-13 | 105° C. | 27 nm |
| Example 4-14 | R-14 | 100° C. | 26 nm |
| Example 4-15 | R-15 | 105° C. | 26 nm |
| Comparative Example 4-1 | R-16 | 105° C. | 33 nm |
| Comparative Example 4-2 | R-17 | 105° C. | 37 nm |
| Comparative Example 4-3 | R-18 | 100° C. | 34 nm |
| Comparative Example 4-4 | R-19 | 100° C. | 38 nm |

It is evident from Table 4 that the resist compositions within the scope of the invention are fully resistant to pattern collapse when processed by the immersion ArF excimer laser lithography. This is because the resist compositions of the invention have improved dissolution properties, i.e., swell reducing effect.

Japanese Patent Application No. 2010-218249 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:
1. A polymer consisting of
recurring units having the general formula (2a):

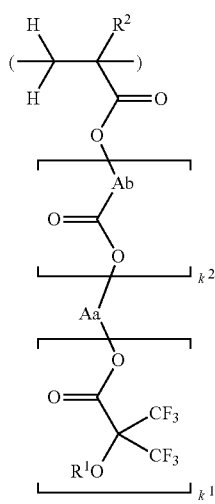

(2a)

wherein $R^1$ is hydrogen or is a straight-chain monovalent $C_1$-$C_{20}$ hydrocarbon group or a branched or cyclic monovalent $C_3$-$C_{20}$ hydrocarbon group in which any constituent —$CH_2$— moiety may be replaced by —O— or —C(=O)—, $R^2$ is hydrogen, fluorine, methyl, or trifluoromethyl, Aa is a branched ($k^1$+1)-valent $C_2$-$C_{20}$ hydrocarbon or fluorinated hydrocarbon group, Ab is a straight-chain divalent $C_1$-$C_6$ hydrocarbon group or a branched divalent $C_2$-$C_6$ hydrocarbon group or a cyclic divalent $C_3$-$C_6$ hydrocarbon group, $k^1$ is 1, and $k^2$ is 0 or 1;

recurring units of at least one type selected from the general formulas (2A) to 2(C):

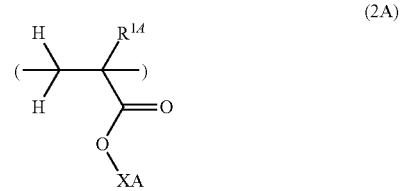

(2A)

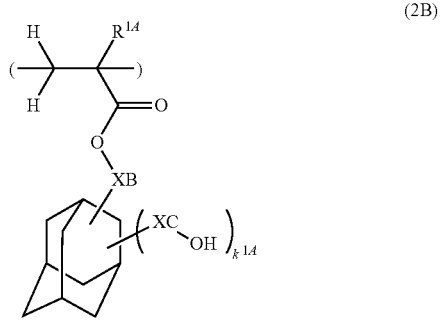

(2B)

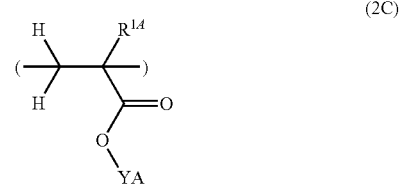

(2C)

wherein $R^{1A}$ is hydrogen, fluorine, methyl, or trifluoromethyl, XA is an acid labile group, XB and XC are each independently a single bond or a straight-chain divalent $C_1$-$C_4$ hydrocarbon group or branched divalent $C_2$-$C_4$ hydrocarbon group, YA is a substituent group having lactone structure, and $k^{1A}$ is an integer of 1 to 3;

recurring units of at least one type selected from the general formulas (d1) to (d3):

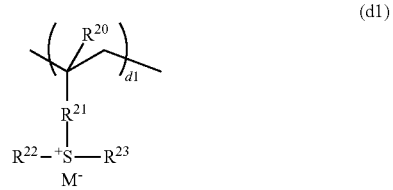

(d1)

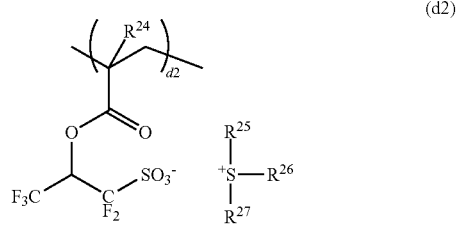

(d2)

(d3)

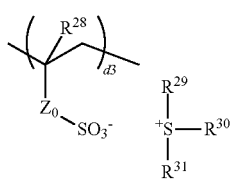

wherein $R^{20}$, $R^{24}$ and $R^{28}$ are hydrogen or methyl, $R^{21}$ is a single bond, phenylene, —O—$R^{33}$—, or —C(=O)—Y—$R^{33}$—, Y is oxygen or NH, $R^{33}$ is a straight-chain $C_1$-$C_6$ alkylene group or a branched $C_2$-$C_6$ alkylene or alkenylene group or a cyclic $C_3$-$C_6$ alkylene or alkenylene group or a phenylene group, which may contain a carbonyl (—CO—), ester (—COO—), ether (—O—), or hydroxyl radical, $R^{22}$, $R^{23}$, $R^{25}$, $R^{26}$, $R^{27}$, $R^{29}$, $R^{30}$, and $R^{31}$ are each independently a straight-chain $C_1$-$C_{12}$ alkyl group which may contain a carbonyl, ester, or ether radical, a branched or cyclic $C_3$-$C_{12}$ alkyl group which may contain a carbonyl, ester, or ether radical, a $C_6$-$C_{12}$ aryl group, a $C_7$-$C_{20}$ aralkyl group, or a thiophenyl group, $Z_0$ is a single bond, methylene, ethylene, phenylene, fluorinated phenylene, —O—$R^{32}$—, or —C(=O)—$Z_1$—$R^{32}$—, $Z_1$ is oxygen or NH, $R^{32}$ is a straight-chain $C_1$-$C_6$ alkylene group or alkenylene group or a branched $C_2$-$C_6$ alkylene group or alkenylene group or a cyclic $C_3$-$C_6$ alkylene group or alkenylene group or a phenylene group, which may contain a carbonyl, ester, ether, or hydroxyl radical, and $M^-$ is a non-nucleophilic counter ion; and recurring units derived from monomers selected from the group consisting of substituted acrylic acid esters, unsaturated carboxylic acids, cyclic olefins, and unsaturated acid anhydrides, wherein, in said polymer, the recurring units having formula (2a) are contained in a portion of 5 to 70 mol %, the recurring units having formulas (2A) to (2C) are contained in a proportion of 30 to 95 mol %, and the recurring units derived from monomers selected from the group consisting of substituted acrylic acid esters, unsaturated carboxylic acids, cyclic olefins, and unsaturated acid anhydrides are contained in a proportion of up to 80 mol %, said mol % amounts being based upon the total moles of recurring units in said polymer.

2. A resist composition comprising the polymer of claim 1 as a base resin, an acid generator, and an organic solvent.

3. A resist composition comprising the polymer of claim 1 as a base resin and an organic solvent.

4. A pattern forming process comprising the steps of applying the resist composition of claim 2 onto a substrate to form a resist coating; heat treating the coating and exposing it to high-energy radiation or electron beam through a photomask; optionally heat treating the exposed coating, and developing it with a developer.

5. A pattern forming process comprising the steps of:
applying the resist composition of claim 2 onto a substrate to form a resist coating;
heat treating the coating and exposing to high-energy radiation or electron beam through a photomask, the exposing step being immersion lithography with a liquid having a high refractive index of at least 1.0 interposed between the resist coating and a projection lens; and
heat treating the exposed coating and developing with a developer.

6. A pattern forming process comprising the steps of:
applying the resist composition of claim 2 onto a substrate to form a resist coating;
heat treating the coating and exposing to high-energy radiation or electron beam through a photomask, the exposing step being immersion lithography with a liquid having a high refractive index of at least 1.0 interposed between the resist coating and a projection lens; and
heat treating the exposed coating and developing with a developer;
the process further comprising the step of applying a protective coating on the resist coating.

7. A fluorinated monomer having the general formula (2):

(2)

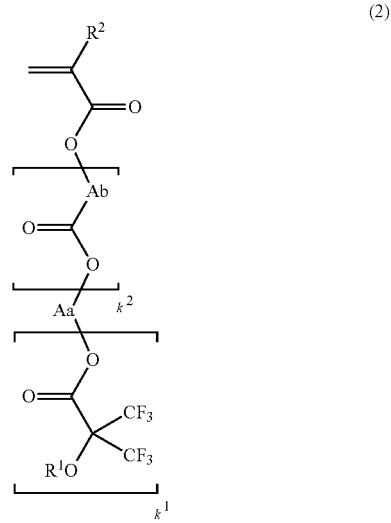

wherein $R^1$ is hydrogen or is a straight-chain monovalent $C_1$-$C_{20}$ hydrocarbon group or a branched or cyclic monovalent $C_3$-$C_{10}$ hydrocarbon group in which any constituent —$CH_2$— moiety may be replaced by —O— or —C(=O)—, $R^2$ is hydrogen, fluorine, methyl, or trifluoromethyl, Aa is a straight-chain ($k^1$+1)-valent $C_1$-$C_{20}$ hydrocarbon or fluorinated hydrocarbon group or a branched ($k^1$+1)-valent $C_2$-$C_{20}$ hydrocarbon or fluorinated hydrocarbon group or a cyclic ($k^1$+1)-valent $C_3$-$C_{20}$ hydrocarbon or fluorinated hydrocarbon group, Ab is a straight-chain divalent $C_1$-$C_6$ hydrocarbon group or a branched divalent $C_2$-$C_6$ hydrocarbon group or a cyclic divalent $C_3$-$C_6$ hydrocarbon group, $k^1$ is an integer of 2 or 3, and $k^2$ is 0 or 1.

8. A polymer comprising recurring units having the general formula (2a):

(2a)

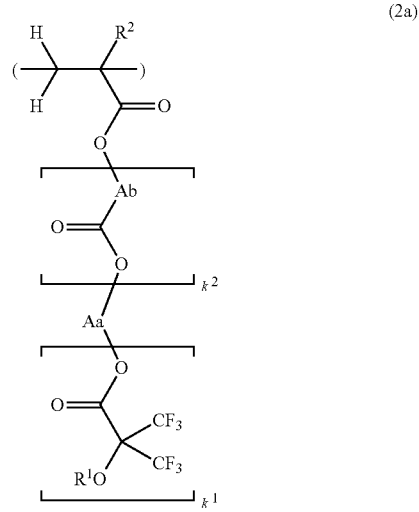

wherein $R^1$ is hydrogen or is a straight-chain monovalent $C_1$-$C_{20}$ hydrocarbon group or a branched or cyclic monovalent $C_3$-$C_{20}$ hydrocarbon group in which any constituent —$CH_2$— moiety may be replaced by —O— or —C(=O)—, $R^2$ is hydrogen, fluorine, methyl or trifluoromethyl, Aa is a straight-chain ($k^1$+1)-valent $C_1$-$C_{20}$ hydrocarbon or fluorinated hydrocarbon group or a branched ($k^1$+1)-valent $C_2$-$C_{20}$ hydrocarbon or fluorinated hydrocarbon group or a cyclic ($k^1$+1)-valent $C_3$-$C_{20}$ hydrocarbon or fluorinated hydrocarbon group, Ab is a straight-chain divalent $C_1$-$C_6$ hydrocarbon group or a branched divalent $C_2$-$C_6$ hydrocarbon group or a cyclic divalent $C_3$-$C_6$ hydrocarbon group, $k^1$ is an integer of 2 or 3, and $k^2$ is 0 or 1.

9. The polymer of claim 8, further comprising recurring units of at least one type selected from the general formulas (2A) to (2D):

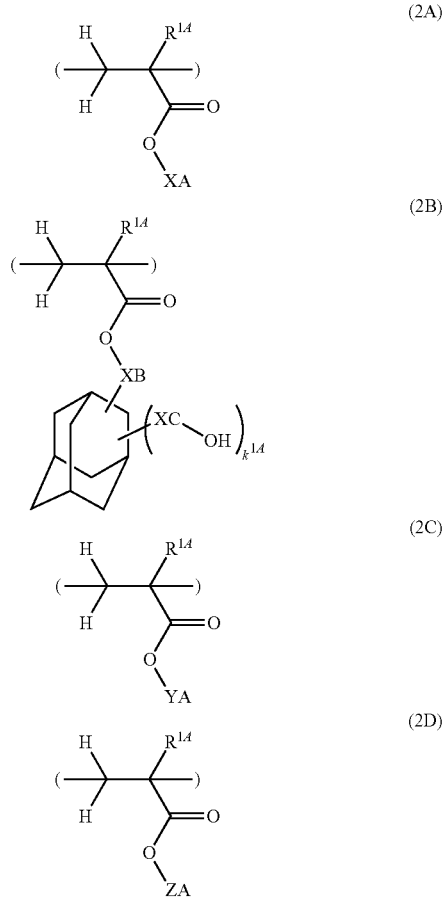

wherein $R^{1A}$ is hydrogen, fluorine, methyl, or trifluoromethyl, XA is an acid labile group, XB and XC are each a single bond or a straight-chain divalent $C_1$-$C_4$ hydrocarbon group or branched divalent $C_2$-$C_4$ hydrocarbon group, YA is a substituent group having lactone structure, ZA is hydrogen, a $C_1$-$C_{15}$ fluoroalkyl group, or a $C_1$-$C_{15}$ fluoroalcohol-containing substituent group, and $k^{1A}$ is an integer of 1 to 3.

10. The polymer of claim 8, further comprising recurring units of at least one type selected from the general formulas (d1) to (d3):

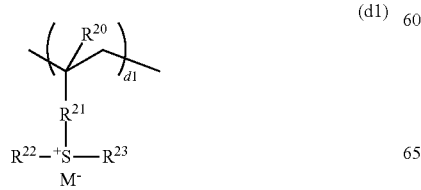

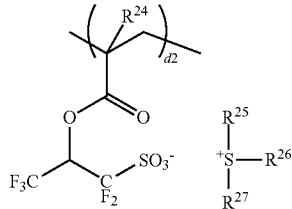

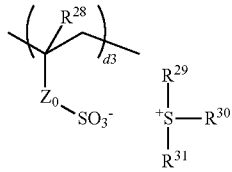

wherein $R^{20}$, $R^{24}$ and $R^{28}$ are hydrogen or methyl, $R^{21}$ is a single bond, phenylene, —O—$R^{33}$—, or —C(=O)—Y—$R^{33}$—, Y is oxygen or NH, $R^{33}$ is a straight-chain $C_1$-$C_6$ alkylene or alkenylene group, or a branched $C_2$-$C_6$ alkylene or alkenylene group, or a branched or cyclic $C_3$-$C_6$ alkylene group or alkenylene group or a phenylene group, which may contain a carbonyl (—CO—), ester (—COO—), ether (—O—), or hydroxyl radical, $R^{22}$, $R^{23}$, $R^{25}$, $R^{26}$, $R^{27}$, $R^{29}$, $R^{30}$, and $R^{31}$ are each independently a straight-chain $C_1$-$C_{12}$ alkyl group or a branched or cyclic $C_3$-$C_{12}$ alkyl group which may contain a carbonyl, ester, or ether radical, or a $C_6$-$C_{12}$ aryl group, a $C_7$-$C_{20}$ aralkyl group, or a thiophenyl group, $Z_0$ is a single bond, methylene, ethylene, phenylene, fluorinated phenylene, —O—$R^{32}$—, or —C(=O)—$Z_1$—$R^{32}$—, $Z_1$ is oxygen or NH, $R^{32}$ is a straight-chain $C_1$-$C_6$ alkylene group or alkenylene group or a branched $C_2$-$C_6$ alkylene group or alkenylene group or a cyclic $C_3$-$C_6$ alkylene group or alkenylene group or a phenylene group, which may contain a carbonyl, ester, ether, or hydroxyl radical, and $M^-$ is a non-nucleophilic counter ion.

11. A resist composition comprising the polymer of claim 8 as a base resin, an acid generator, and an organic solvent.

12. A resist composition comprising the polymer of claim 10 as a base resin and an organic solvent.

13. A pattern forming process comprising the steps of applying the resist composition of claim 11 onto a substrate to form a resist coating; heat treating the coating and exposing it to high-energy radiation or electron beam through a photomask; optionally heat treating the exposed coating, and developing it with a developer.

14. A pattern forming process comprising the steps of
applying the resist composition of claim 11 onto a substrate to form a resist coating;
heat treating the coating and exposing to high-energy radiation or electron beam through a photomask; and
heat treating the exposed coating and developing with a developer,
the exposing step being immersion lithography with a liquid having a high refractive index of at least 1.0 interposed between the resist coating and a projection lens.

15. A pattern forming process comprising the steps of
applying the resist composition of claim 11 onto a substrate to form a resist coating;
heat treating the coating and exposing to high-energy radiation or electron beam through a photomask;
heat treating the exposed coating and developing with a developer; and
applying a protective coating on the resist coating, the exposing step being immersion lithography with a liquid having a high refractive index of at least 1.0 interposed between the protective coating and a projection lens.

\* \* \* \* \*